US006221355B1

(12) United States Patent
Dowdy

(10) Patent No.: US 6,221,355 B1
(45) Date of Patent: Apr. 24, 2001

(54) ANTI-PATHOGEN SYSTEM AND METHODS OF USE THEREOF

(75) Inventor: Steven F. Dowdy, Clayton, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 09/208,966

(22) Filed: Dec. 10, 1998

Related U.S. Application Data

(60) Provisional application No. 60/082,402, filed on Apr. 20, 1998, and provisional application No. 60/069,012, filed on Dec. 10, 1997.

(51) Int. Cl.[7] .......................... A61K 39/00; A61K 39/12; A61K 39/21; C07H 21/04; C12P 21/08

(52) U.S. Cl. ...................................... 424/192.1; 424/204.1; 424/208.1; 536/23.4; 530/387.3; 530/388.3

(58) Field of Search .................. 536/23.4; 530/387.3; 530/388.3; 424/192.1, 204.1, 208.1

(56) References Cited

U.S. PATENT DOCUMENTS

| 5,132,213 | 7/1992 | Bachmair et al. | 435/69.7 |
|---|---|---|---|
| 5,652,122 | 7/1997 | Frankel et al. | 435/69.7 |
| 5,670,617 | 9/1997 | Frankel et al. | 530/300 |
| 5,674,980 | 10/1997 | Frankel et al. | 530/350 |

OTHER PUBLICATIONS

K. A. Barrie, et al. "Natural Variation in HIV–1 Protease, Gag p7 and p6, and Protease Cleavage Sites Within Gag/Pol Polyproteins: Amino Acid Substitutions in the Absence of Protease Inhibitors in Mothers and Children Infected by Human Immunodeficiency Virus Type 1", *Virology* 219:407–416 (1996).

T. Fernandez–Alnemri et al. "CPP32 a Novel Human Apoptotic Protein with Homology to *Caenorhabditis elegans* Cell Death Protein Ced–3 and Mammalian Interleukin–1β–conveting Enzyme", *J. Biol. Chem.* 269: 30761 (1994).

Richard P. Moon, et al. "Expression and Characterisation of Plasmepsin I from *Plasmodium falciparum*", *Eur. J. Biochem.* 244:552 (1997).

C. V. Dang, "Nuclear and Nucleolar Targeting Sequences of c–erb–A, c–myb, N–myc, p53, HSP70, and HIV tat Proteins", *J. Biol. Chem.* 264 (30) : 18019–18023 (1989).

Craig B. Thompson "Apoptosis in the Pathogenesis and Treatment of Disease", *Science* 267: 1456 (1995).

Karyn T. O'Neil et al. "A Thermodynamic Scale for the Helix–Forming Tendencies of the Commonly occurring Amino Acids", *Science* 250: 646 (1990).

Arash Grakoui et al. "Characterization of the Hepatitis C Virus–Encoded Serine Proteinase: Determination of Proteinase–Dependent Polyprotein Cleavage Sites", *J. of Virology* 67: 2832 (1993).

A. A. Kolykhalov et al. "Specificity of the Hepatitis C Virus NS3 Serine Protease: Effects of Substitutions at the 3/4A, 4A/4B, 4B/5A, and 5A/5B Cleavage Sites on Polyprotein Processing", *J. of Virology* 68: 7525 (1994).

(List continued on next page.)

*Primary Examiner*—Hankyel T. Park
(74) *Attorney, Agent, or Firm*—Robert L. Buchanan; Kerri Pollard Schray; Peter F. Corless

(57) ABSTRACT

The present invention provides an anti-pathogen system comprising one or more fusion proteins that includes a transduction domain and a cytotoxic domain. The cytotoxic domain is specifically activated by a pathogen infection. The anti-pathogen system effectively kills or injures cells infected by one or a combination of different pathogens. Further provided are protein transduction domains that provide enhanced transduction efficiency.

21 Claims, 16 Drawing Sheets

OTHER PUBLICATIONS

B. J. Calnan et al. "Analysis of Arginine–Rich Peptides From the HIV tat Protein Reveals Unusual Features of RNA–Protein Recognition", *Genes & Development* 5: 201 (1991).

M. Woo et al. "Essential Contribution of Caspase 3/CPP32 to Apoptosis and Its Associated Nuclear Changes", *Genes & Development* 12: 806 (1998).

G. S. Salvesen et al. "Caspases: Intracellular Signaling By Proteolysis", *Cell* 91: 443 (1997).

G. Elliott et al. "Intercellular Trafficking and Protein Delivery by a Herpesvirus Structural Protein", *Cell* 88: 223 (1997).

N. P. C. Walker et al. "Crystal Structure of the Crysteine Protease Interleukin–1β–Converting Enzyme: A. $(p20/p10)_2$ Homodimer", *Cell* 78: 343 (1994).

B. Elangoven et al "Functional Comparison of the Basic Domains of the Tat Proteins of Human Immunodeficiency Virus Types 1 and 2 in trans Activation", *Journal of Virology*, Apr. 1992, pp. 2031–2036.

A. D. Frankel et al. "Activity of Synthetic Peptides From the Tat Protein of Human Immunodeficiency Virus Type 1", *Proc. Natl. Acad. Sci. USA*, vol. 86, pp. 7397–7401, Oct. 1989 Biochemistry.

A. D. Frankel et al. "Cellular Uptake of the Tat Protein From Human Immunodeficiency Virus", *Cell*, vol. 55, pp. 1189–1193, Dec. 23, 1988.

W. Shen et al. "Conjugation of Poly–L–lysine to Albumin and Horseradish Peroxidase: A Novel Method of Enhancing The Cellular Uptake of Proteins", *Proc. Natl. Acad. Sci. USA*, vol. 75, No. 4, pp. 1872–1876, Apr. 1978, Cell Biology.

L. A. Sternson, "Obstacles to Polypeptide Delivery", *Annals New York Academy of Science*, pp. 19–21.

S. J. Arrigo et al., "Intrinsic Activity of Human Immunodeficiency Virus Type 1 Protease Heterologous Fusion Proteins in Mammalian Cells", *DNA And Cell Biology*, vol. 14, No. 1, (1995), pp. 15–23.

P. Moy et al., "Tat–Mediated Protein Delivery Can Facilitate MHC Class 1 Presentation of Antigens", *Molecular Biotechnology*, vol. 6 (1996), pp. 105–113.

N. A. Lissy et al., "TCR Antigen–Induced Cell Death Occurs from a Late G1 Phase Cell Cycle Check Point", *Immunity*, vol. 8, pp. 57–65, Jan. 1998.

X. Luo et al., "Bid, a Bcl2 Interacting Protein, Mediates Cytochrome c Release from Mitochondria in Response to Acitvation of Cell Surface Death Receptors", *Cell*, vol. 94, pp. 481–490, Aug. 21, 1998.

K. Wang et al., "BID: A Novel BH3 Domain–only Death Agonist", *Genes & Development* 10:2859–2869 (1996).

H. Nagahara, et al., "Transduction Of Full–Length TAT Fusion Proteins Into Mammalian Cells: TAT–$p27^{Kip1}$ Induces Cell Migration", *Nature Medicine*, vol. 4, No. 12, Dec. 1998 pp. 1449–1452.

L. Chen, et al., "Increased Cellular Uptake of the Human Immunodeficiency Virus–1 Tat Protein After Modification With Biotin", *Analytical Biochemistry*, 227, (1995), pp. 168–175.

D. T. Kim, et al., "Introduction Of Soluble Proteins Into The MHC Class I Pathway by Conjugation to an HIV tat Peptide[1]", *The Journal of Immunology*, (1997), pp. 1666–1668.

D. Derossi, et al., "The Third Helix of the Antennapedia Homeodomain Translocates Through biological Membranes", *the Journal of J. Biological Chemistry*, (1994), pp. 10444–10450.

Penetratin 1 "A New Vector For The Internalization Of Molecules Into Eucaryotic Cells", 11 pages.

D. W. Nicholson, et al., "Caspases: Killer Proteases", *TIBS*, Aug. 1997, pp. 299–306.

H. Li, et al., "Cleavage of BID by Caspase 8 Mediates the Mitochondrial Damage In the Fas Pathway of Apoptosis", *Cell*, vol. 94, Aug. 21, 1998, pp. 491–501.

pTAT LINKER:

TAT DOMAIN

```
BamHI HindIII
GGA TCC AAG CTT GGC TAC GGC CGC AAG AAA CGC CGC CAG CGC CGC CGC GGT
 G   S   K   L   G   Y   G   R   K   K   R   R   Q   R   R   R   G BamHI     NcoI       KpnI AgeI    XhoI       SphI         Eco  BstBI HindIII
GGA TCC ACC ATG GCC GGT ACC GGT CTC GAG GTG CAT GCG GTG AAT TCG AAG CTT
 G   S   T   M   A   G   T   G   L   E   V   H   A   V   N   S   K   L
```

-FOLLOWED BY 20 AMINO ACIDS TO TAA Ts TERMINATION codon.

pTAT-HA LINKER:

THE HA TAG, FLANKED BY GLYCINE RESIDUES, WAS INSERTED INTO THE NcoI SITE
OF pTAT. THE N' NcoI SITE HAS BEEN INACTIVATED.

```
ORIGINAL                                                    NEW
NcoI-(inactive)              AatII                          NcoI
CC ATG TCC GGC TAT CCA TAT GAC GTC CCA GAC TAT GCT GGC TCC ATG GGC ...
    M   S   G   Y   P   Y   D   V   P   D   Y   A   G   S   M   G
```

FIG. 2

|   | 1 | 2 |
|---|---|---|
|   | COLUMN 1 | COLUMN 2 |
| 1 | PROTEASE | 92 |
| 2 | C-32 WT | 77 |
| 3 | C-32 MUT | 103 |
| 4 | C-32 WT+PROT | 25 |
| 5 | MUT +PROT | 96 |
| 6 | DRUG | 92 |
| 7 | WT+DRUG+PRO | 72 |
| 8 | MUT+DRUG+PR | 86 |

FIG. 6B

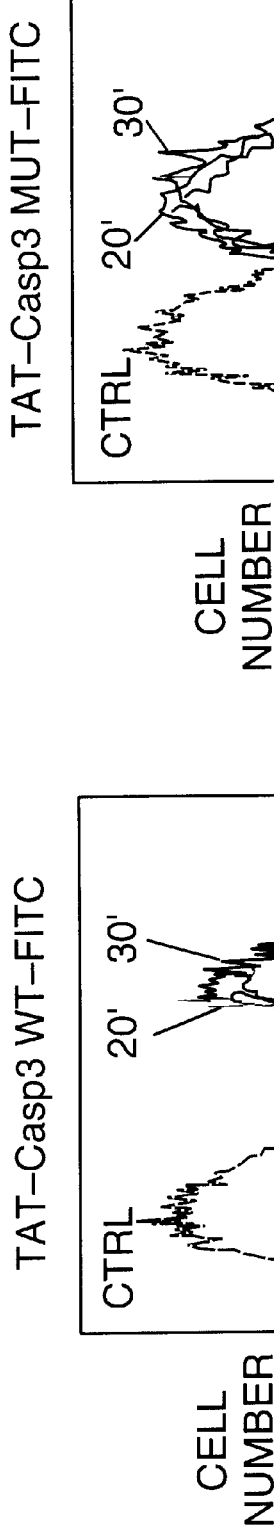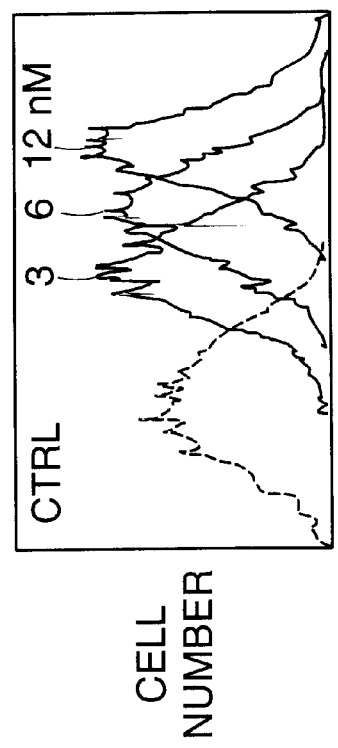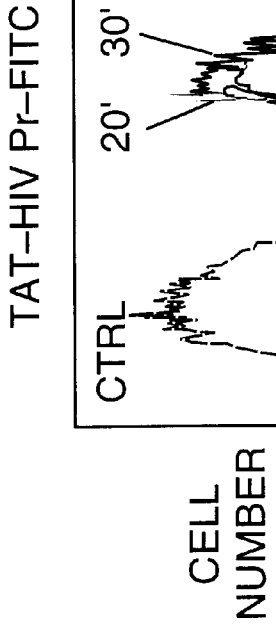
FIG. 9C
FIG. 9E
FIG. 9B
FIG. 9D

SEQUENCE LISTING

<160> NUMBER OF SEQ ID NOS: 57

<210> SEQ ID NO: 1
<211> LENGTH: 16
<212> TYPE: PRT
<213> ORGANISM: human

<400> SEQUENCE: 1

Ala Lys Ile Trp Phe Gln Asn Arg Arg Met Lys Trp Lys Lys Glu Asn
1               5                   10                  15

<210> SEQ ID NO: 2
<211> LENGTH: 11
<212> TYPE: PRT
<213> ORGANISM: human

<400> SEQUENCE: 2

Tyr Gly Arg Lys Lys Arg Arg Gln Arg Arg Arg
1               5                   10

<210> SEQ ID NO: 3
<211> LENGTH: 11
<212> TYPE: PRT
<213> ORGANISM: human

```
<400> SEQUENCE: 3

Tyr Ala Arg Lys Ala Arg Arg Gln Ala Arg Arg
1               5                   10

<210> SEQ ID NO: 4
<211> LENGTH: 11
<212> TYPE: PRT
<213> ORGANISM: human

<400> SEQUENCE: 4

Tyr Ala Arg Ala Ala Ala Arg Gln Ala Arg Ala
1               5                   10

<210> SEQ ID NO: 5
<211> LENGTH: 11
<212> TYPE: PRT
<213> ORGANISM: human

<400> SEQUENCE: 5

Tyr Ala Arg Ala Ala Arg Arg Ala Ala Arg Arg
1               5                   10

<210> SEQ ID NO: 6
<211> LENGTH: 11
<212> TYPE: PRT
<213> ORGANISM: human

<400> SEQUENCE: 6

Tyr Ala Arg Ala Ala Arg Arg Ala Ala Arg Ala
1               5                   10

<210> SEQ ID NO: 7
<211> LENGTH: 11
<212> TYPE: PRT
<213> ORGANISM: human

<400> SEQUENCE: 7

Tyr Ala Arg Arg Arg Arg Arg Arg Arg Arg Arg
1               5                   10

<210> SEQ ID NO: 8
<211> LENGTH: 11
<212> TYPE: PRT
<213> ORGANISM: human

<400> SEQUENCE: 8

Tyr Ala Ala Ala Arg Arg Arg Arg Arg Arg Arg
1               5                   10

<210> SEQ ID NO: 9
<211> LENGTH: 14
<212> TYPE: PRT
<213> ORGANISM: human

<400> SEQUENCE: 9

Ser Gln Val Ser Gln Asn Tyr Pro Ile Val Gln Asn Leu Gln
1               5                   10

<210> SEQ ID NO: 10
<211> LENGTH: 14
<212> TYPE: PRT
<213> ORGANISM: human

<400> SEQUENCE: 10
```

```
Cys Thr Glu Arg Gln Ala Asn Phe Leu Gly Lys Ile Trp Pro
  1               5                  10
```

<210> SEQ ID NO: 11
<211> LENGTH: 14
<212> TYPE: PRT
<213> ORGANISM: human

<400> SEQUENCE: 11

```
Ile Gly Cys Thr Leu Asn Phe Pro Ile Ser Pro Ile Glu Thr
  1               5                  10
```

<210> SEQ ID NO: 12
<211> LENGTH: 105
<212> TYPE: DNA
<213> ORGANISM: human
<220> FEATURE:
<221> NAME/KEY: CDS
<222> LOCATION: (1)..(105)

<400> SEQUENCE: 12

```
gga tcc aag ctt ggc tac ggc cgc aag aaa cgc cgc cag cgc cgc cgc       48
Gly Ser Lys Leu Gly Tyr Gly Arg Lys Lys Arg Arg Gln Arg Arg Arg
  1               5                  10                  15 ggt gca tcc acc atg gcc ggt acc ggt ctc gag gtg cat gcg gtg aat       96
Gly Ala Ser Thr Met Ala Gly Thr Gly Leu Glu Val His Ala Val Asn
                 20                  25                  30 tcg aag ctt                                                          105
Ser Lys Leu
         35
```

<210> SEQ ID NO: 13
<211> LENGTH: 35
<212> TYPE: PRT
<213> ORGANISM: human

<400> SEQUENCE: 13

```
Gly Ser Lys Leu Gly Tyr Gly Arg Lys Lys Arg Arg Gln Arg Arg Arg
  1               5                  10                  15

Gly Ala Ser Thr Met Ala Gly Thr Gly Leu Glu Val His Ala Val Asn
                 20                  25                  30

Ser Lys Leu
         35
```

<210> SEQ ID NO: 14
<211> LENGTH: 50
<212> TYPE: DNA
<213> ORGANISM: human
<220> FEATURE:
<221> NAME/KEY: CDS
<222> LOCATION: (3)..(50)

<400> SEQUENCE: 14

```
cc atg tcc ggc tat cca tat gac gtc cca gac tat gct ggc tcc atg        47
   Met Ser Gly Tyr Pro Tyr Asp Val Pro Asp Tyr Ala Gly Ser Met
     1               5                  10                  15 ggc                                                                   50
Gly
```

<210> SEQ ID NO: 15
<211> LENGTH: 16
<212> TYPE: PRT
<213> ORGANISM: human

<400> SEQUENCE: 15

```
Met Ser Gly Tyr Pro Tyr Asp Val Pro Asp Tyr Ala Gly Ser Met Gly
  1               5                  10                  15
```

<210> SEQ ID NO: 16
<211> LENGTH: 11
<212> TYPE: PRT
<213> ORGANISM: human

<400> SEQUENCE: 16

```
Gly Arg Lys Lys Arg Gln Arg Arg Gly
  1               5                  10
```

<210> SEQ ID NO: 17
<211> LENGTH: 9
<212> TYPE: PRT
<213> ORGANISM: human

<400> SEQUENCE: 17

```
Tyr Pro Tyr Asp Val Pro Asp Tyr Ala
  1               5
```

<210> SEQ ID NO: 18
<211> LENGTH: 57
<212> TYPE: DNA
<213> ORGANISM: human

<400> SEQUENCE: 18

| catgtcaggc tcccaggtgt cacagaacta tccaatcgtg cagaacctgc agggcgc | 57 |
|---|---|

<210> SEQ ID NO: 19
<211> LENGTH: 60
<212> TYPE: DNA
<213> ORGANISM: human

<400> SEQUENCE: 19

| catgcattca ggctgcaccg aacgccaggc taacttcctg ggcaaaatct ggccaggcgc | 60 |
|---|---|

<210> SEQ ID NO: 20
<211> LENGTH: 90
<212> TYPE: DNA
<213> ORGANISM: human

<400> SEQUENCE: 20

| cgcctcgagg gcggctgcac cgaacgccag gctaacttcc tgggcaaaat ctggccaggc | 60 |
|---|---|
| ggaatatccc tggacaacag ttataaaatg | 90 |

<210> SEQ ID NO: 21
<211> LENGTH: 72
<212> TYPE: DNA
<213> ORGANISM: human

<400> SEQUENCE: 21

| ggcggctccc aggtgtcaca gaactatcca atcgtgcaga acctgcaggg cggtgttgat | 60 |
|---|---|
| gatgacatgg cg | 72 |

<210> SEQ ID NO: 22
<211> LENGTH: 75
<212> TYPE: DNA
<213> ORGANISM: human

<400> SEQUENCE: 22

| accgccctgc aggttctgca cgattggata gttctgtgac acctgggagc cgcctgtctc | 60 |
|---|---| aatgccacag tccag                                                        75

<210> SEQ ID NO: 23
<211> LENGTH: 37
<212> TYPE: DNA
<213> ORGANISM: human

<400> SEQUENCE: 23
cgagctacgc gaattcttag tgataaaaat agagttc                                37

<210> SEQ ID NO: 24
<211> LENGTH: 85
<212> TYPE: DNA
<213> ORGANISM: human

<400> SEQUENCE: 24
ccatgcgtgg taccgaactg gactgtggca ttgagacagg cggctcccag gtgtcacaga       60
actatccaat cgtgcagaac ctgca                                             85

<210> SEQ ID NO: 25
<211> LENGTH: 34
<212> TYPE: DNA
<213> ORGANISM: human

<400> SEQUENCE: 25
cgggccggcc ccatggcttc gtacccctgc catc                                   34

<210> SEQ ID NO: 26
<211> LENGTH: 39
<212> TYPE: DNA
<213> ORGANISM: human

<400> SEQUENCE: 26
ggcgggccgg gaattctcag ttagcctccc ccatctccc                              39

<210> SEQ ID NO: 27
<211> LENGTH: 87
<212> TYPE: DNA
<213> ORGANISM: human

<400> SEQUENCE: 27
cgcgccatgg gcggctccca ggtgtcacag aactatccaa tcgtgcagaa cctgcagggc      60
ggcgactctg aggtcagcaa cggttcc                                           87

<210> SEQ ID NO: 28
<211> LENGTH: 52
<212> TYPE: DNA
<213> ORGANISM: human

<400> SEQUENCE: 28
ttcctgggca aaatctggcc aggcggcagc caggccagcc gctccttcaa cc               52

<210> SEQ ID NO: 29
<211> LENGTH: 46
<212> TYPE: DNA
<213> ORGANISM: human

<400> SEQUENCE: 29
gttagcctgg cgttcggtgc agcctgtctg cagctcgtct tcgagg                      46

<210> SEQ ID NO: 30

-continued

```
<211> LENGTH: 88
<212> TYPE: DNA
<213> ORGANISM: human

<400> SEQUENCE: 30
cgcgccatgg gcggctgcac cgaacgccag gctaacttcc tgggcaaaat ctggccaggc    60
ggcagccagg ccagccgctc cttcaacc                                       88

<210> SEQ ID NO: 31
<211> LENGTH: 71
<212> TYPE: DNA
<213> ORGANISM: human

<400> SEQUENCE: 31
cgcgaattct cagtcagcat agtctgggag gtcatatgga tagccgtcca tctcgtttct    60
aaccaagttc c                                                         71

<210> SEQ ID NO: 32
<211> LENGTH: 90
<212> TYPE: DNA
<213> ORGANISM: human

<400> SEQUENCE: 32
cgcctcgagg gcggctgcac cgaacgccag gctaacttcc tgggcaaaat ctggccaggc    60
ggaatatccc tggacaacag ttataaaatg                                     90

<210> SEQ ID NO: 33
<211> LENGTH: 74
<212> TYPE: DNA
<213> ORGANISM: human

<400> SEQUENCE: 33
ccgccctgca ggttctgcac gattggatag ttctgtgaca cctgggagcc gcctgtctca    60
atgccacagt ccag                                                      74

<210> SEQ ID NO: 34
<211> LENGTH: 72
<212> TYPE: DNA
<213> ORGANISM: human

<400> SEQUENCE: 34
ggcggctccc aggtgtcaca gaactatcca atcgtgcaga acctgcaggg cggtgttgat    60
gatgacatgg cg                                                        72

<210> SEQ ID NO: 35
<211> LENGTH: 37
<212> TYPE: DNA
<213> ORGANISM: human

<400> SEQUENCE: 35
cgagctacgc gaattcttag tgataaaaat agagttc                             37

<210> SEQ ID NO: 36
<211> LENGTH: 85
<212> TYPE: DNA
<213> ORGANISM: human

<400> SEQUENCE: 36
ccatgcgtgg taccgaactg gactgtggca ttgagacagg cggctccag gtgtcacaga     60 actatccaat cgtgcagaac ctgca                                          85
```

```
<210> SEQ ID NO: 37
<211> LENGTH: 41
<212> TYPE: DNA
<213> ORGANISM: human

<400> SEQUENCE: 37
cggtccatgg gcggcggccc tcaggtcact ctttggcaac g                           41

<210> SEQ ID NO: 38
<211> LENGTH: 36
<212> TYPE: DNA
<213> ORGANISM: human

<400> SEQUENCE: 38
cgggaattct caaaaattta aagtgcaacc aatctg                                 36

<210> SEQ ID NO: 39
<211> LENGTH: 11
<212> TYPE: PRT
<213> ORGANISM: human

<400> SEQUENCE: 39

Tyr Ala Arg Ala Ala Ala Arg Pro Ala Arg Ala
 1               5                  10

<210> SEQ ID NO: 40
<211> LENGTH: 11
<212> TYPE: PRT
<213> ORGANISM: human

<400> SEQUENCE: 40

Tyr Ala Arg Ala Pro Ala Arg Gln Ala Arg Ala
 1               5                  10

<210> SEQ ID NO: 41
<211> LENGTH: 11
<212> TYPE: PRT
<213> ORGANISM: human

<400> SEQUENCE: 41

Tyr Ala Arg Ala Pro Ala Arg Pro Ala Arg Ala
 1               5                  10

<210> SEQ ID NO: 42
<211> LENGTH: 8
<212> TYPE: PRT
<213> ORGANISM: human
<220> FEATURE:
<223> OTHER INFORMATION: positions 1, 5 & 8 are basic amino acids;
      positions 2, 3, 4, 6 & 7 are alpha-helix enhancing
      amino acids

<400> SEQUENCE: 42

Xaa Xaa Xaa Xaa Xaa Xaa Xaa Xaa
 1               5

<210> SEQ ID NO: 43
<211> LENGTH: 8
<212> TYPE: PRT
<213> ORGANISM: human
<220> FEATURE:
<223> OTHER INFORMATION: positions 1, 4, 5 & 8 are basic amino acids;
      positions 2, 3, 6 & 7 are alpha-helix enhancing
      amino acids
```

```
<400> SEQUENCE: 43

Xaa Xaa Xaa Xaa Xaa Xaa Xaa Xaa
 1               5

<210> SEQ ID NO: 44
<211> LENGTH: 11
<212> TYPE: PRT
<213> ORGANISM: human
<220> FEATURE:
<223> OTHER INFORMATION: positions 7 & 10 are basic amino acids;
      positions 1, 2, 4 & 9 are alpha-helix enhancing
      amino acids; positions 5 & 8 are either proline or
      alpha-helix enhancing amino acids; positions 6 & 11
      either basic or alpha-helix enhancing amino acids;

<400> SEQUENCE: 44

Xaa Xaa Arg Xaa Xaa Xaa Xaa Xaa Xaa Xaa Xaa
 1               5                  10

<210> SEQ ID NO: 45
<211> LENGTH: 10
<212> TYPE: PRT
<213> ORGANISM: human

<400> SEQUENCE: 45

Thr Pro Pro Lys Lys Lys Lys Arg Lys Val
 1               5                  10

<210> SEQ ID NO: 46
<211> LENGTH: 14
<212> TYPE: PRT
<213> ORGANISM: human

<400> SEQUENCE: 46

Gly Thr Val Ser Phe Ser Phe Pro Gln Ile Thr Leu Trp Gln
 1               5                  10

<210> SEQ ID NO: 47
<211> LENGTH: 20
<212> TYPE: PRT
<213> ORGANISM: human

<400> SEQUENCE: 47

Cys Met Ser Ala Asp Leu Glu Val Val Thr Ser Thr Trp Val Leu Val
 1               5                  10                  15

Gly Gly Val Leu
            20

<210> SEQ ID NO: 48
<211> LENGTH: 20
<212> TYPE: PRT
<213> ORGANISM: human

<400> SEQUENCE: 48

Tyr Gln Glu Phe Asp Glu Met Glu Glu Cys Ala Ser His Leu Pro Tyr
 1               5                  10                  15

Ile Glu Gln Gly
            20

<210> SEQ ID NO: 49
<211> LENGTH: 20
<212> TYPE: PRT
<213> ORGANISM: human

<400> SEQUENCE: 49
```

-continued

```
Trp Ile Ser Ser Glu Cys Thr Thr Pro Cys Ser Gly Ser Trp Leu Arg
 1               5                  10                  15
Asp Ile Trp Asp
            20

<210> SEQ ID NO: 50
<211> LENGTH: 20
<212> TYPE: PRT
<213> ORGANISM: human

<400> SEQUENCE: 50

Gly Ala Asp Thr Glu Asp Val Val Cys Cys Ser Met Ser Tyr Thr Trp
 1               5                  10                  15
Thr Gly Ala Leu
            20

<210> SEQ ID NO: 51
<211> LENGTH: 14
<212> TYPE: PRT
<213> ORGANISM: human

<400> SEQUENCE: 51

Trp Ala Leu Glu Arg Met Phe Leu Ser Phe Pro Thr Thr Lys
 1               5                  10

<210> SEQ ID NO: 52
<211> LENGTH: 11
<212> TYPE: PRT
<213> ORGANISM: human

<400> SEQUENCE: 52

Ala Gly Arg Lys Lys Arg Arg Gln Arg Arg Arg
 1               5                  10

<210> SEQ ID NO: 53
<211> LENGTH: 11
<212> TYPE: PRT
<213> ORGANISM: human

<400> SEQUENCE: 53

Tyr Ala Ala Ala Ala Ala Ala Ala Ala Ala Ala
 1               5                  10

<210> SEQ ID NO: 54
<211> LENGTH: 16
<212> TYPE: PRT
<213> ORGANISM: human

<400> SEQUENCE: 54

Arg Gln Ile Lys Ile Trp Phe Gln Asn Arg Arg Met Lys Trp Lys Lys
 1               5                  10                  15

<210> SEQ ID NO: 55
<211> LENGTH: 11
<212> TYPE: PRT
<213> ORGANISM: human

<400> SEQUENCE: 55

Tyr Ala Arg Ala Ala Arg Arg Pro Arg Arg Arg
 1               5                  10

<210> SEQ ID NO: 56
<211> LENGTH: 11
```

-continued

<212> TYPE: PRT
<213> ORGANISM: human

<400> SEQUENCE: 56

Tyr Ala Arg Ala Pro Arg Arg Ala Arg Arg Arg
1 5 10

<210> SEQ ID NO: 57
<211> LENGTH: 11
<212> TYPE: PRT
<213> ORGANISM: human

<400> SEQUENCE: 57

Tyr Ala Arg Ala Pro Arg Arg Pro Arg Arg Arg
1 5 10

ANTI-PATHOGEN SYSTEM AND METHODS OF USE THEREOF

CROSS REFERENCE TO RELATED APPLICATIONS

The present application is a continuation-in-part of co-pending U.S. Provisional Application Serial No. 60/082,402 filed on Apr. 20, 1998, and a continuation-in-part of co-pending U.S. Provisional Application Serial No. 60/069,012, filed on Dec. 10, 1997. The disclosures of both those co-pending provisional applications are incorporated herein by reference in their entirety.

BACKGROUND OF THE INVENTION

1. Field of the Invention

The present invention relates to an anti-pathogen system that kills or injures pathogen-infected cells by introducing into the cells a fusion protein comprising a protein transduction domain and a cytotoxic domain. The cytotoxic domain is capable of being specifically activated in cells infected by the pathogen. Further provided are specified transduction domains that enhance transduction capacity of the fusion protein. The present invention has a variety of uses such as killing or injuring cells infected by one or more pathogenic viruses or plasmodia.

2. Background

A variety of pathogens infect mammals, particularly primates such as humans. For example, certain viruses, bacteria, fungi, yeasts, worms, plasmodia, and protozoa are recognized human pathogens. See e.g., *Harrison's Principles of Internal Medicine*, 12$^{th}$ ed. McGraw-Hill, Inc. (1991).

Pathogens often kill or injure cells by mechanisms that manifest morphological characteristics. For example, pathogen-infected cells undergoing apoptosis or necrosis extLibit readily identifiable cellular changes.

There has been progress toward understanding cell proteins and particularly enzymes, involved in apoptosis. For example, certain cell proteases such as caspases (i.e. cysteinyl aspartate-specific proteases), *C. elegans* ced-3 and granzyme B have been implicated in apoptosi. Nucleic acid sequences encoding several capsases and proteolytic substrates for same are known. For example, caspase-3 (i.e. CPP32) has been particularly well-studied. See e.g., Thompson, C. B. *Science*, 267:1456 (1995); and Walker, N. P. C. et al. *Cell*, 78:343 (1994).

There have been related attempts to identify proteins involved in necrosis. For example, necrosis is thought to follow expression of certain DNA viruses such as herpes viruses.

Pathogens often induce synthesis of certain proteins, particularly enzymes such as proteases. It is likely that nearly all pathogens require one or more specific proteases to complete a productive infection. For example, it is believed that the following exemplary human pathogens require expression of at least one pathogen-specific protease: cytomegalovirus (CMV), herpes simplex virus, e.g., type-1 (HSV-1); hepatitis virus, e.g., tyrpe C (HCV); certain plasmodia, e.g., *P. falciparum*; human immunodeficiency virus type 1 (HIV-1, also referred to as HTLV-III, LAV or HTLV-III/LAV); human immunodeficiency virus type 2 (HIV-2), Kaposi's sarcoma-associated herpes virus (KSHV or human herpes virus 8), yellow fever virus, certain flaviviruses and rhinovirus.

Sometimes the proteases are encoded by the pathogen itself. In this instance, the proteases are often referred to as pathogen-specific proteases. For example, CMV, HCV, HIV-1, HIV-2, KSHV, and *P. falciparum* are representative of pathogens that encode pathogen-specific proteases. These proteases serve a variety of functions and can be nearly indispensable for a productive infection.

There has been some efforts to analyze particular pathogen specific proteases such as serine-type proteinases encoded by HCV, aspartic proteases (i.e. plasmepsins I and II) encoded by *P. falciparum*, and a maturational protease encoded by HSV-1. See e.g., Dilanni, C. L. et al., *J. Biol. Chem.*, 268:2048 (1993); and Francis, S. E. et al., *EMBOJ.*, 13:306 (1994).

In contrast, inducible expression of certain host cell proteases is believed to modulate productive infection by other pathogens. These host cell proteases are sometimes referred to as inducible host cell proteases. For example, bacterial infection of eukaryotes such as certain plants can induce expression of normally quiescent host cell proteases. Induction of the host cell proteases may be an attempt to damage the pathogen, thereby protecting the host cell from infection.

Infection by HIV viruses has attracted substantial attention. There is now almost universal agreement that the human family of these retroviruses are the etiological agent of acquired immune deficiency syndrome (AIDS) and related disorders. Productive infection by nearly all HIV viruses requires expression of certain HIV-specific proteases. See, for example, Barre-Sinoussi et al., *Science*, 220:868–871 (1983); Gallo et al., *Science*, 224:500–503 (1984).

There has been progress toward developing therapeutic agents to target pathogen infections such as HIV infections. One general approach has focussed on interrupting distinct stages of the pathogen infection. In particular, therapeutic agents have been developed to combat certain HIV specific enzymes such as reverse transcriptase (RT) and pathogen-specific proteases.

Other agents such as certain cytokines have been used in attempts to treat CMV and HSV infections.

Other proposed methods for treating pathogen infections relate to what has been referred to as "intracellular immunization". Briefly, the methods involve genetically modifying host cells in an attempt to render them incapable of supporting a productive infection. For example, it has been suggested that certain eukaryotic cells can be made immune to pathogen infection by using the method. See e.g., Baltimore, *Nature*, 335:739:5 (1988); Harrison et al., *Human Gene Therapy*, 3:461 (1992); and U.S. Pat. No. 5,554,528 to Harrison et al.

A more specific form of genetic modification has been reported to involve administering gene constucts that encode cytotoxins. In this instance, the contructs are desigened so that the genes can express cytoxin once inside the cells.

However, the prior methods for treating pathogen infections have several limitations.

For example, methods that use a cytotoxin to kill cells have not always been successful. One explanation may relate to pleiotropic effects reported for many intracellular cytotoxins. Those effects can often complicate analysis of cell killing. Additionally, many gene constructs that encode a cytotoxin can exhibit undesirably high basal activities inside host cells. These problems can produce what is known as "leaky" cytotoxin expression, leading to death of infected and non-infected cells.

Other methods for treating pathogen infection have also had problems. For example, methods relying on use of a drug have not been completely effective. More particularly, subjects infected by aggressive or persistent pathogens often require prolonged therapeutic intervention, sometimes over a period of months or even years. Proliferation of drug resistant pathogens is becoming increasingly problematic. Thus, the long-term value of the methods is controversial.

In particular, current treatment of HIV utilizes small inhibitory molecules that target HIV protease. However, emergence of resistant HIV strains is increasingly problematic. See e.g., Coffin, J. M., et al. *Retroviruses*, Cold Spring Harbor Press, Cold Spring Harbor, N.Y. (1997); Kaplan, A. H. et al. Selection of multiple human immunodeficiency virus type 1 variants that encode viral proteases with decreased sensitivity to an inhibitor of the viral protease. *Proc. Natl. Acad. Sci. USA* 91: 5597 (1994); Condra, J. H. et al. In vivo emergence of HIV-1 variants resistant to multiple protease inhibitors. *Nature* 374: 569 (1995); Gulnik, S. V. et al. Kinetic characterization and cross-resistance patterns of HIV-1 protease mutants selected under drug pressure. *Biochemistry* 34: 9282 (1995); and Tisdale, M. et al. Cross-resistance analysis of human immunodeficiency virus type 1 variants individually selected for resistance to five different protease inhibitors, *Antimicrob. Agents Chemother.* 39:1704 (1995).

There has been recognition that the retroviral TAT protein may find use in certain therapuetic settings. TAT has been reported to transactivate certain HIV genes and it is believed to be essential for productive infection by most human HIV retroviruses. The TAT protein has been used to bring certain types of fusion proteins into cells. This process is generally referred to as transduction. See U.S. Pat. No. 5,652,122 to Frankel et al.; and Chen, L. L. et al., *Anal. Biochem.*, 227:168 (1995).

However, use of TAT to transduce fusion proteins into cells has been associated with significant shortcomings.

For example, it has been difficult to maintain suitable levels of the fusion proteins inside cells. Attempts to overcome this problem have included administering large amounts of the fusion proteins to help maintain adequate intracellular levels. The need to administer large amounts of the fusion proteins may prevent or hinder widespread use of some therapeutic fusion proteins. For example, use of large amounts of some TAT fusion proteins may negatively impact viability of some host cells.

Further, it has been difficult to maintain many of the prior transducing fusion proteins in a therapeutically relevant conformation. As an illustration, it is believed that many prior TAT fusion proteins may partially or completely unfold during transduction. That unfolding has potential to significantly reduce or eliminate transduction in many instances.

Additionally, the need to correctly fold the prior transducing fusion proteins has complicated efforts to purify and store the proteins.

Further drawbacks have been reported to be associated with proteins fused to TAT or certain TAT fragments. These drawbacks relate to how TAT is believed to act inside cells. More specifically, there has been acknowledgement that TAT or the TAT fragments may confer certain biological characteristics to the fusion proteins. Some of these characteristics and particularly nuclear localization and RNA binding may not always be desirable. In particular, there has been concern that many TAT fusion proteins may be difficult to position outside the nucleus or away from RNA. See e.g., Dang et al., *J. Biol. Chem.*, 264:18109 (1989); Calnan, B. J. et al., *Genes Dev.*, 5:201 (1991) for a discussion of TAT-associated properties.

It would be desirable to have an anti-pathogen system that exhibits high transduction efficiency and can specifically deliver a cytotoxin to pathogen infected cells. It would be further desirable to have an anti-pathogen system that can deliver the cytotoxin as an essentially inactive molecule that can be activated by pathogen infected cells.

SUMMARY OF THE INVENTION

The present invention relates to an anti-pathogen system that exhibits high transduction efficiency aid specifically kills or injures cells infected by one or more pathogens. In general, the anti-pathogen system includes a fusion molecule that comprises a transduction domain and a cytotoxic domain genetically and hence covalently linked together as an in-frame fusion molecule. The invention further relates to transduction domains that enhance the transduction efficiency of the fusion molecules. The anti-pathogen system is essentially inactive in uninfected cells but it is specifically activated in cells infected by the pathogen. Further provided are methods of using the anti-pathogen system to treat infection by a pathogen and particularly human pathogens such as certain viruses and plasmodia.

Preferred use of the anti-pathogen system entails that the pathogen infection induce at least one pathogen specific protease. Preferably, that protease is capable of specifically cleaving a target amino acid sequence. The target amino acid sequence is one component of the fusion molecule and it is sometimes referred to herein as a protease recognition or cleavage site. Specific cleavage of the protease recognition site cleaves the fusion molecule, generally at or near the cytotoxin domain, to form a cytotoxin. The cytotoxin so formed is specifically capable of killing or injuring cells infected by the pathogen.

Significantly, the present anti-pathogen system links formation of the cytotoxin to presence of the pathogen-induced protease, thereby providing highly focussed cytotoxic action to infected cells. Formation of the cytotoxin is minimized or eliminated in uninfected cells and in infected cells that keep the pathogen inactive. The anti-pathogen system is therefore capable of effectively and specifically discriminating between productively infected and uninfected cells.

The present anti-pathogen system has a number of important advantages. For example, it can be readily manipulated to respond to changes in pathogen serotype. That is, the anti-pathogen system can be specifically tailored to kill or injure cells infected by one or more pathogen strains. In contrast, prior methods of blocking infection and especially drug-based methods are not usually designed to respond to changes in pathogen serotype. This deficiency often results in uncontrolled growth of drug-resistant pathogen strains. As will become more apparent from the discussion that follows, the anti-pathogen system has capacity to harness production of one or more pathogen-induced protease to kill or injure cells infected by the pathogen serotype. In marked contrast, most prior drug-based methods merely attempt to inhibit pathogenic processes, e.g., by blocking activity of a pathogen gene product. The present anti-pathogen system is more flexible and can be used to reduce or even eliminate emergence of pathogen strains by specifically exposing infected cells to cytotoxin.

As an illustrative example of the flexibility of the present invention, the anti-pathogen system is particularly useful against emergence of HIV serotypes. For example, many patients infected by HIV manifest several viral strains. Conventional drug-based therapies usually attempt to block activity of an HIV enzyme such as RT or an HIV protease.

The clinical outcome of such treatment is often emergence of a spectrum of HIV serotypes. It has been recognized that the HIV serotypes can develop partial or even complete resistance to the therapies. Even so-called "cocktail" therapies employing multiple anti-HIV drugs have been problematic. In contrast, the anti-pathogen system of the present invention is highly flexible and can be adapted to kill or injure cells that produce the HIV serotypes by employing HIV proteases. Significantly, the anti-pathogen system is also formated to meet an increase in the activity of those HIV proteases or an increase in the number of infected cells with enhanced activation of the system.

The flexibility of the present anti-pathogen system arises in part because it can be tailored to kill or injure cells infected by nearly any number of HIV serotypes. Thus it is possible in accord with the present invention to format the anti-pathogen system to combat one or more HIV strains in a particular patient. This feature is highly useful in several respects. For example, it provides a specific method of fighting an HIV infection in a single patient without resorting to administration of potentially harmful or ineffective drugs. Significantly, the anti-pathogen system can be formatted to be effective at nanomoler doses or less. This low level of anti-viral activity is significantly lower than many present drug-based therapies. This feature of the invention positively impacts patient tolerance for the anti-pathogen system.

Further, the present anti-pathogen system is fully compatible with recognized anti-HIV therapies such as those using a "cocktail" format (ie. combination of anti-HIV drugs) to kill or injure infected cells.

In particular embodiments of the present invention, the anti-pathogen system is employed to reduce or eliminate emergence of HIV serotypes by exploiting the HIV protease produced by the virus.

Illustrative fusion proteins that kill HIV-infected cells are provided in Examples 11 and 12 below.

In addition, the present anti-pathogen system is capable of transducing unexpectedly large fusion molecules into cells. In particular, it has been discovered that the anti-pathogen system accommodates misfolded (i.e. partially or completely unfolded) fusion molecules and provides for efficient transduction of those molecules into cells. In particular, it is believed that the anti-pathogen system is compatible with misfolded fusion molecules having a molecular weight in the range of about 1 to about 500 kDa or more. The anti-pathogen system therefore is widely applicable to transducing a large spectrum of fusion molecules into cells.

More specifically, the ability to transduce misfolded fusion molecules has substantial advantages over prior transduction methods. For example, it has been found that misfolded fusion proteins used in accord with this invention significantly enhance transduction efficiency sometimes by as much as about 10 fold or greater. In addition, by misfolding the fusion proteins, it has been found that it is possible to optimize the amount of the fusion molecules inside cells. Preparation and storage of the fusion molecules are also positively impacted by the misfolding.

As discussed, the present anti-pathogen system is flexible. For example, it is not limited to any particular type of pathogen or cell provided that the pathogen is capable of inducing at least one specified protease in that cell. The protease can be a pathogen-induced or host cell induced protease that is specifically induced (i.e. synthesized or activated in response to the infection. However, the specified protease must be capable of cleaving the protease recognition site on the fusion molecule to activate the cytotoxin.

The present anti-pathogen system and methods of using same can be used in vitro or in vivo. Further, the order or number of components of the fusion molecule are not important so long as each component on the molecule is operatively linked and can perform specified functions for which it is intended.

The cytotoxin produced by the anti-pathogen system is preferably selected to kill or injure infected cells in the presence of one or more of cell proteases and usually the pathogen- or host cell induced proteases. Preferably, the cytotoxin can kill at least about 20%, 25%, 50%, 75%, 80%, or 90% of the cells and preferably up to about 95%, 98% or 100% of the cells infected by the pathogen as assayed by standard cell viability tests. A preferred viability test is a standard Trypan Blue exclusion assay although other assays may be used as needed. It is also preferred that the cytotoxin activity be limited to cells in which it is produced.

As noted previously, the present anti-pathogen system includes an in-frame fusion molecule. The fusion can be accomplished by conventional recombinant nucleic acid methods. If desired, the fusion can also be achieved by chemically linking the transducing protein to the cytotoxic domain according to conventional methods described below.

In general, the transduction domain of the fusion molecule can be nearly any synthetic or naturally-occurring amino acid sequence that can transduce or assist in the transduction of the fusion molecule. For example, transduction can be achieved in accord with the invention by use of a protein sequence and particularly an HIV TAT protein or fragment thereof that is covalently linked to the fusion molecule. Alternatively, the transducing protein can be the Antennapedia homeodomain or the HSV VP22 sequence, or suitable transducing fragments thereof such as those known in the field.

The type and size of the transducing amino acid sequence will be guided by several parameters including the extent of transduction desired. Preferred sequences will be capable of transducing at least about 20%, 25%, 50%, 75%, 80% or 90% of the cells of interest, more preferably at least about 95%, 98%% and up to about 100% of the cells. Transduction efficiency, typically expressed as the percentage of transduced cells, can be determined by several conventional methods such as those specific microscopical methods discussed below (e.g., flow cytometric analysis).

Additionally preferred transducing sequences will manifest cell entry and exit rates (sometimes referred to as $k_1$ and $k_2$, respectively) that favor at least picomolar amounts of the fusion molecule in the cell. The entry and exit rates of the amino acid sequence can be readily determined or at least approximated by standard kinetic analysis using detectably-labeled fusion molecules. Typically, the ratio of the entry rate to the exit rate will be in the range of from between about 5 to about 100 up to about 1000.

Particularly are transducing amino acid sequences that include at least a peptide featuring substantial alpha-helicity. It has been discovered that transduction is optimized when the transducing amino acid sequence exhibits significant alpha-helicity. Also preferred are those sequences having basic amino acid residues that are substantially aligned alone at least one face of the peptide. Typically such preferred transduction sequences are synthetic protein or peptide sequences.

More preferred transducing amino acid sequences are referred to as class I transducing domains or like term and include a strong alpha helical structure with a trace of arginine (Arg) residues down the helical cylinder.

In one embodiment, the class I transducing domain is a peptide is represented by the following general formula: B1-X$_1$-X$_2$-X$_3$-B$_2$-X$_4$-X$_5$-B$_3$ (SEQ ID NO: 42); wherein B$_1$, B$_2$ and B$_3$ are each independently a basic amino acid, the same or different; and X$_1$, X$_2$, X$_3$, X$_4$ and X$_5$ are each independently an alpha-helix enhancing amino acid the same or different.

In another embodiment, the class I transducing peptide is represented by the following general formula: B$_1$-X$_1$-X$_2$-B$_2$-B$_3$-X$_3$-X$_4$-B$_4$ (SEQ ID NO: 43); wherein B$_1$, B$_2$, B$_3$, and B$_4$ are each independently a basic amino acid, the same or different; and X$_1$, X$_2$, X$_3$, and X$_4$ are each independently an alpha-helix enhancing amino acid the same or different.

Additionally preferred transducing peptides are often referred to herein as "class II" domains or like terms. These domains generally require basic residues, e.g., lysine (Lys) or arginine (Arg), preferably arginine (Arg), and further including at least one proline (Pro) residue sufficient to introduce "kinks" into the domain.

In one embodiment, the class II domain is a peptide represented by the following sequence: X-X-R-X-(P/X)-(B/X)-B-(P/X)-X-B-(B/X) (SEQ ID NO: 44), wherein X is any alpha helical promoting residue, preferably alanine; P/X is either proline or X as previously defined; B is a basic amino acid residue, e.g., arginine (Arg) or lysine (Lys), preferably arginine (Arg); R is arginine (Arg) and B/X is either B or X as defined above.

Additional transducing sequences in accord with this invention include a TAT fragment that comprises at least amino acids 49 to 56 of TAT up to about the full-length TAT sequence. A preferred TAT fragment includes one or more amino acid changes sufficient to increase the alpha-helicity of that fragment. In most instances, the amino acid changes introduced will involve adding a recognized alpha-helix enhancing amino acid. Alternatively, the amino acid changes will involve removing one or more amino acids from the TAT fragment the impede alpha helix formation or stability. In more specific embodiment, the TAT fragment will include at least one amino acid substitution with an alpha-helix enhancing amino acid. Preferably the TAT fragment will be made by standard peptide synthesis techniques although recombinant DNA approaches may be preferred in some cases.

Additional transduction proteins of this invention include the TAT fragment in which the TAT 49–56 sequence has been modified so that at least two basic amino acids in the sequence are substantially aligned along at least one face of the TAT fragment and preferably the TAT 49–56 sequence. In one embodiment, that alignment is achieved by making at least one specified amino acid addition or substitution to the TAT 49–56 sequence. Illustrative TAT fragments include at least one specified amino acid substitution in at least amino acids 49–56 of TAT which substitution aligns the basic amino acid residues of the 49–56 sequence along at least one face of the segment and preferably the TAT 49–56 sequence.

Additional transduction proteins in accord with this invention include the TAT fragment in which the TAT 49–56 sequence includes at least one substitution with an alpha-helix enhancing amino acid. In one embodiment, the substitution is selected so that at least two basic amino acid residues in the TAT fragment are substantially aligned along at least one face of that TAT fragment. In a more specific embodiment, the substitution is chosen so that at least two basic amino acid residues in the TAT 49–56 sequence are substantially aligned along at least one face of that sequence.

Additionally provided are chimeric transducing proteins that include parts of at least two different transducing proteins. For example, chimeric transducing proteins can be formed by fusing two different TAT fragments, e.g., one from HIV-1 and the other from HIV-2. Alternatively, other transducing proteins can be formed by fusing a desired transducing protein to heterologous amino acid sequences such as 6XHis, (sometimes referred to as "HIS"), EE, HA or Myc.

As noted above, the fusion molecule of the present invention also includes a fused cytotoxic domain. In general, the cytotoxic domain includes a potentially toxic molecule and one or more specified protease cleavage sites. By the term "potentially toxic" is meant that the molecule is not significantly cytotoxic to infected or non-infected cells (preferably less than about 30%, 20%, 10%, 5%, 3%, or 2% cell mortality as assayed by standard cell viability tests. More preferred is 1% or less cell mortality) when present as part of the cytotoxic domain. As noted above, the protease cleavage sites are capable of being specifically cleaved by one or more than one of the proteases induced by the pathogen infection.

In particular, the protease cleavage sites are selected to remain essentially uncleaved in uninfected cells, thereby maintaining the cytotoxic domain in an inactive state. These protease cleavage sites may also be selected to remain essentially uncleaved in cells in which the pathogen is inactive. However, in the presence of a specified pathogen-induced or host cell induced protease, the protease cleavage sites are specifically cleaved to produce a cytotoxin from the potentially toxic molecule. That is, cleavage of the protease sites releases the cytotoxic domain from the fusion molecule, thereby forming an active cytotoxin. The one or more protease cleavage sites are generally positioned in the cytotoxic domain to optimize release of all or part of the domain from the fusion protein and to enhance formation of the cytotoxin.

More preferred protease cleavage sites are selected so as not to be cleaved by a protease normally associated with an uninfected cell. These proteases have been generically referred to as "housekeeping" proteases and are well known.

Protease cleavage sites are sometimes referred to herein as "pathogen-specific" cleavage sites to denote capacity to be specifically cleaved by one or more proteases induced by the pathogen infection. The protease cleavage sites are "responsive" to a pathogen (or more than one pathogen) insofar as cleavage of those sites releases the cytotoxin domain from the fusion molecule, thereby activating the cytotoxin.

The cytotoxic domain can include one or more of a variety of potentially toxic molecules provided that it can be released from the fusion molecule as discussed. An illustrative cytotoxic domain for use in the fusion molecules includes an immature enzyme. These immature enzyme is sometimes referred to as zymogen, proenzyme, preproenzyme or simply as "pre-" "pre-pro" or "pro-" forms of more mature enzyme. Preferred zymogens can be specifically activated to a cytotoxin (ie. a cytotoxic enzyme) by site-specific proteolysis at one or more naturally-occuring protease cleavage sites on the zymogen. The zymogens can be further processed in some instances by self-proteolysis.

Particularly, a cytotoxic domain that includes a preferred zymogen will include one or more specified protease cleavage sites that have been added within and/or around the zymogen. The cleavage sites are optionally positioned to facilitate release and processing of the zymogen to a mature or more mature cytotoxic enzyme.

In particular, the addition of the protease cleavage sites to the zymogens can be supplative with respect to the naturally-occurring protease cleavage sites in that zymogen. However it is preferred that the cleavage sites be substituted for one or more of the naturally-occurring cleavage sites. In this embodiment, the substituted protease cleavage sites in the zymogen are capable of being specifically cleaved by one or more pathogen-specific proteases. It has been found that by partially or completely substituting the naturally-occurring protease cleavage sites of the zymogen with one or more pathogen responsive cleavage sites, maturation of the zymogen into a cytotoxin is brought under substantial or complete control by the pathogen infection.

A variety of specific zymogens are suitable for inclusion in the cytotoxic domain as discussed below. Active forms of those zymogens generally include bacterial toxins and particularly exotoxins, plant toxins, and invertebrate toxins including conotoxins, snake and spider toxins.

Further contemplated cytotoxic domains include known proteins with potential to exert genetically dominant characteristics. That is, the proteins can be specifically cleaved from the fusion protein and can subsequently override one or more cell functions such as cell replication. In this embodiment, the potentially dominant protein must not manifest the dominant characteristic (sometimes known as a dominant phenotype) until that protein is released from the fusion protein. Examples of potentially dominant proteins in accord with the invention include proteins that inhibit cell replication such as the retinoblastoma protein (Rb), p16 and p53.

Further contemplated cytotoxic domains include essentially inactive enzymes that have capacity to convert certain nucleosides or analogs thereof into a cytotoxin. In this embodiment, the cytotoxic domain will include one or more specified protease cleavage sites, that is preferably positioned to release the inactive enzyme from the fusion protein. Following the release, the enzyme converts the nucleoside or analog thereof into a cytotoxin. Examples of such enzymes include viral thymidine kinase and nucleoside deaminases such as cytosine deaminase. Also contemplated are cytotoxic domains comprising catalytically active fragments of the enzymes such as those generally known in the field.

The present anti-pathogen system provides a number of additional important advantages. For example, the anti-pathogen system unexpectedly accommodates misfolded fusion proteins. As will become more apparent from the discussion and examples which follow, that feature has been found to substantially boost levels of the fusion protein inside cells. Typically, a corresponding increase in the amount of administered fusion protein is not required. Without wishing to be bound to theory, it is believed that transduction of misfolded fusion molecules requires modest numbers of molecules and only a few of those need be refolded to manifest an effective cytotoxic effect. For example, it is believed that with certain preferred fusion proteins such as those described below in Examples 5–6, only about 10 to 100 correctly refolded fusion proteins are needed to kill or injure infected cells. Thus, the present invention can decrease or even eliminate the need to concentrate large number of cytotoxic molecules inside cells to achieve significant anti-pathogen activity.

In addition, it has been found that activity of the present anti-pathogen system is enhanced in many cases by mass action. More particularly, it has been found that specific cleavage of the cytotoxic domain can draw additional fusion molecules into infected cells. This feature can be particularly advantageous for those fusion proteins that include cytotoxic domains which are preferably administered in sub-optimal doses. In such instances, the fusion protein is specifically concentrated in infected cells, thereby increasing levels of the cytotoxin to lethal or near lethal levels. Importantly, the cytotoxin remains at sub-optimal levels in uninfected cells.

Still further advantages are provided with respect to particular fusion proteins of the invention that include the TAT fragment described above. For example, the cytotoxic domain of a protein fused to the TAT fragment need not be directed to the cell nucleus or to RNA. More specifically, the present fusion molecules are formatted to separate the cytotoxic domain from the TAT fragment inside infected cells, thereby avoiding unnecessary concentration of the protein in the nucleus or with RNA. It is recognized that in uninfected cells, such fusion proteins may be directed to the nucleus or to RNA. Thus, differential localization of the fusion protein in infected and non-infected cells can provide means of distinguishing such cells from one another, e.g., by inspection.

The anti-pathogen system of the invention can also positively impact certain drug-based anti-pathogen therapies. More specifically, cells infected by retroviruses and particularly HIV can harbor infectious particles for long periods of time, sometimes months or even years. Over this time, retroviruses can develop substantial resistance to most drugs, sometimes by changing one or only a few genomic sequences. It has been recognized that once the retroviruses become resistant to one class of drugs, such viruses can be become resistant to a spectrum of drugs. Thus, therapies using drug-based approaches are generally inflexible and do not readily adapt to presence of resistant viruses. Related concerns have been raised with respect to development of other resistant pathogen strains such as certain plasmodia.

In contrast, the present anti-pathogen systems kills or injures cells infected by pathogens regardless of pathogen capacity to acquire drug resistance. It is believed that development of drug resistant pathogens and particularly drug resistant HIV strains, is nearly impossible with the present anti-pathogen system due to the large number of protease cleavage sites that the system can accommodate. As an illustrative example, HIV virus has been reported to have about 8 to 10 such cleavage sites. In order to develop substantial resistance against the anti-pathogen system, which system could include one or more of these sites, that virus would have to modify those cleavage sites as well as the corresponding viral protease.

Accordingly, use of the present anti-pathogen system is expected to significantly reduce or even eliminate the presence of many pathogen resistant strains and particularly certain drug resistant HIV strains.

Additionally, the anti-pathogen system of the invention is compatible with a variety of drug-based therapies. Thus, the anti-pathogen system can be used as a sole active agent or in combination with one or more therapeutic drugs, e.g. to minimize or eliminate pathogens and particularly drug resistant pathogen strains.

Further provided are substantially pure fusion molecules of the invention.

The invention also provides nucleic acid sequences encoding the fusion proteins, particularly extrachromosomal DNA sequences organized as an autonomously replicating DNA vector.

The invention also provides methods for suppressing or eliminating infection by one or more pathogens in a mammal, particularly a primate such as a human. The methods more specifically include administering a therapeutically effective amount of the present anti-pathogen system. The methods further include treatment of a mammal that suffers from or is susceptible to infection by one or pathogens.

Preferred methods according to the invention for suppressing or eliminating infection by the one or more pathogens include providing the anti-pathogen system as an aerosol and administering same, e.g., through nasal or oral routes. Particularly contemplated are modes of administration which are specifically designed to administer the anti-pathogen system to lung tissue so as to facilitate contact with lung epithelia and enhance transfer into the bloodstream.

Also provided are methods of inducing apoptosis in a pre-determined population of cells in which the method comprises administering to the mammal such as a primate and particularly a human a therapeutically sufficient amount of the anti-pathogen system in the presence of one more pathogens.

The cell infected by one or more pathogens may be a cell maintained in culture, e.g., an immortalized cell line or primary culture of cells or tissue; or the cell can be part of a tissue or organ in vivo (e.g., lung). Thus, the present anti-pathogen system can be used in vitro and in vivo as needed.

The invention also provides substantially pure fusion molecules and particularly fusion proteins that in addition to the aforementioned transduction and cytotoxic domains may also include other components as needed. These components can be covalently or non-covalently linked thereto and may particularly include one or more polypeptide sequences. An added polypeptide sequence will sometimes be referred to herein as protein identification or purification "tag". Exemplary of such tags are EE, 6Xhis, HA and MYC.

As discussed, it is preferred that the fusion proteins described herein by provided in misfolded form although in some instances it may be desirable to use properly folded fusion proteins. The misfolded fusion proteins are typically purified by chromatographic approaches that can be tailored if needed to purify a desired fusion molecule from cell components which naturally accompany it. Typically, the approaches involve isolation of inclusion bodies from suitable host cells, denaturation of misfolded fusion proteins, and use of conventional chromatographic methods to purify the fusion molecules. Expression of the misfolded fusion proteins in the inclusion bodies has several advantages including protecting the misfolded fusion protein from degradation by host cell proteases. In addition, by providing the fusion proteins in misfolded form, time-consuming and costly protein refolding techniques are avoided.

Further provided by the present invention are methods of making substantial quantities of the fusion molecules. Generally stated, the methods include expressing desired fusion molecules in suitable host cells, culturing the cells, and purifying the fusion molecules therefrom to obtain substantially pure fusion molecules. The methods can be used to express and purify a desired fusion protein on a large-scale (i.e. in at least milligram quantities) from a variety of implementations including roller bottles, spinner flasks, tissue culture plates, bioreactor, or a fermentor.

The present methods for isolating and purifying the fusion proteins of the invention are highly useful. For example, for a fusion protein exhibiting a desired killing or injuring activity, it is very useful to have methods for expressing and purifying the fusion proteins. It is particularly useful to have methods that can produce at the fusion proteins in large quantities, so that the fusion molecule can be made as one component of a kit suitable for medical, research, home or commercial use. Further, it is useful to have large-scale quantities of the fusion proteins available to simplify structural analyisis, as well as for further purification and/or testing if desired.

The invention also features in vitro and in vivo screens to detect compounds with therapeutic capacity to modulate and preferably inhibit, proteins and especially proteases induced by a pathogen infection. For example, one method generally comprises infecting a desired cell with a pathogen, contacting the cell with a fusion protein of the invention, transducing the fusion protein, adding the compound to the cells and detecting cells killed or injured by the fusion protein. Efficacy of a particular compound can be readily evaluated by determining the extent of cell killing or injury as a function of concentration of the added compound.

Further provided are methods of suppressing a pathogen infection in a mammal, particularly a primate such as a human, comprising administering to the mammal a therapeutically effective amount of the anti-pathogen system. In one embodiment, the fusion protein includes a covalently linked protein transduction domain and a cytotoxic domain. The method includes transducing the fusion protein into cells of the mammal, cleaving the fusion protein sufficient to release the cytotoxic domain from the fusion protein, concentrating the cytotoxic domain in the cells; and producing a cytotoxin sufficient to suppress the pathogen infection in the mammal. Exemplary pathogens include but are not limited to retroviruses, herpesviruses, viruses capable of causing influenza or hepatitis; and plasmodia capable of causing malaria. Preferred cytotoxic domains and cytotoxins are described in more detail below.

In another embodiment of the method for suppressing the pathogen infection in the mammal, a prodrug is administered (e.g., a suitable nucleoside or analog thereof) and a cytotoxin is produced by contacting the prodrug with the concentrated cytotoxic domain.

Further provided by the present invention are fusion proteins that include covalently linked in sequence: 1) A TAT segment and particularly a protein transducing fragment thereof, and 2) a pathogen induced or host cell induced protease, e.g., HIV protease; or a catalytically active fragment thereof.

Additionally provided by the invention is an anti-pathogen system, wherein the fusion protein comprises covalently linked in sequence: 1) a transduction domain, 2) a first zymogen subunit, 3) a protease cleavage site, and 4) a second zymogen subunit. Also provided is an anti-pathogen system, wherein the transduction domain is TAT, the first zymogen subunit is p5 Bid, the protease cleavage site is an HIV protease cleavage site and the second zymogen subunit is p15 Bid.

The invention also provides an anti-pathogen system, wherein the fusion protein comprises covalently linked in sequence: 1) a transduction domain, 2) a first protease cleavage site, 3) first zymogen subunit, 3) a second protease cleavage site, and 4) a second zymogen subunit. Also provided is an anti-pathogen system, wherein the transduction domain is TAT, the first protease cleavage site is an HIV p7-p1 protease cleavage site, the first zymogen subunit is p17 caspase-3, the second protease cleavage site is an HIV p17-p24 protease cleavage site, and the second zymogen subunit is p12 caspase-3.

The present invention also provides a method of killing an HIV-infected cell. In one embodiment, the method includes contacting the cell with an effective dose of a fusion protein, wherein the fusion protein comprises covalently linked in sequence: 1) a transduction domain, 2) a first zymogen subunit, 3) a protease cleavage site, and 4) a second zymogen subunit; or 1) a transduction domain, 2) a first protease cleavage site, 3) first zymogen subunit, 3) a second protease cleavage site, and 4) a second zymogen subunit. The fusion protein can be administered in vitro or in vivo as needed. For example, the fusion protein can be administered in vivo to a mammal in need of such treatment, e.g., a primate and particularly a human patient infected by the HIV virus.

Other aspects of the invention are disclosed infra.

BRIEF DESCRIPTION OF THE DRAWINGS

FIG. 2 shows nucleotide (SEQ ID NO: 14) and amino acid (SEQ ID NO: 15) sequences of pTAT linker and pTAT HA linker. A minimal TAT domain is in bold. Underlined sequence designates the minimal TAT domain flanked by glycine residues.

FIG. 6B is a table showing percentages of viable cells (under column 2) used in the bar graph of FIG. 6A.

FIG. 8A is a diagram of the Bid protein highlighting the p5 and p15 domains. The casapase cleavage site at $Arg^{59}$ is shown.

FIG. 8B outlines the cloning of the TAT-p5-HIV-p15 fusion protein.

FIG. 8C shows the TAT-HIV-p15 fusion protein. See text for a description of primer designations. Hatched box= overhang between primers 2R and 2F representing HIV cleavages.

FIGS. 9A–E are drawings showing generation and transduction of TAT fusion proteins.

FIG. 9A shows the caspase 3 (Casp3) protein and various TAT/HIV fusion proteins made using the Casp3 p17 and p12 domains.

FIGS. 9B–E are graphs showing FACS analysis of various fluorescein (FITC) labeled TAT fusion proteins.

FIG. 11A shows cell viability following transduction with various TAT fusion proteins along with the HIV protease inhibitor Ritonavir (Rit).

FIG. 11B illustrates cell viability following transduction with various TAT fusion proteins.

FIG. 12A shows results of TUNEL positive cells (apoptotic end-marker) using a TAT fusion protein.

FIG. 12B shows results of a caspase-3 enzyme assay using a TAT fusion protein.

DETAILED DESCRIPTION OF THE INVENTION

Figure 1:
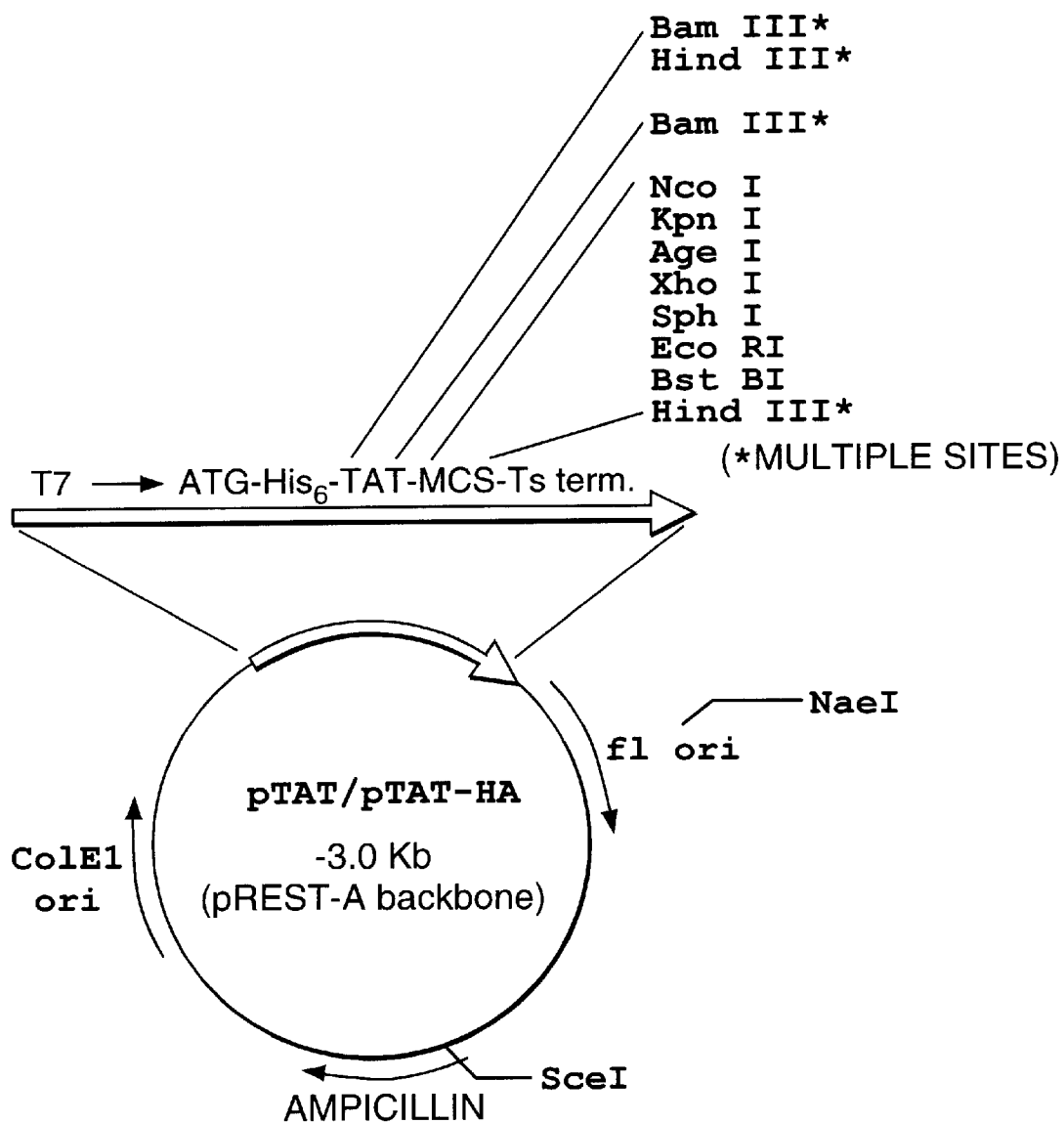
FIG. 1 is a plasmid map of pTAT/pTAT-HA (SEQ ID NOS: 12–13).

As noted above, the present invention features an anti-pathogen system that exhibits high transduction efficiency and specifically kills or injures cells infected by one or more pathogens. The anti-pathogen system generally includes a fusion protein that includes a transduction domain fused to a cytotoxic domain as a genetic in-frame fusion protein. Preferred fusion proteins exhibit enhanced transduction efficiency as determined, e.g., by assays which follow. The transduction domain transduces the fusion protein into cells and once inside the cells, the cytotoxic domain is released from the fusion protein and forms a cytotoxin in the infected cells. In preferred embodiments, function of the fusion protein has been specifically enhanced, e.g., by optimizing transduction domain struture and by misfolding the fusion molecule.

Preferred fusion proteins are capable of killing at least about 25%, 40%, 50%, 60%, or 70%, preferably 80%, 90%, and more preferably at least 95% up to 100% of the cells infected by the pathogen as assayed by standard cell viability tests discussed below.

An "anti-pathogen system" according to the invention includes one or more of the fusion molecules described herein as well as any additional components which may be added thereto such as those which may facilitate solublization, stability and/or activity including transduction efficiency. Examples include but are not limited to a serum protein such as bovine serum albumin, a buffer such as phosphate buffered saline, or a pharmaceutically acceptable vehicle or stabilizer. See generally *Reminington's Pharmaceutical Sciences*, infra, for a discussion of pharmaceutically acceptable vehicles, stabilizers, ect. A preferred anti-pathogen system includes from between about 1 to 3 and are preferably 1 fusion protein dissolved in a pharmaceutically acceptable carrier such as water or buffered saline. Preferably, the anti-pathogen system is provided sterile.

As will be discussed in more detail below, the anti-pathogen system can be administered as a sole active agent or in combination with one or more medicaments such as those specifically provided below.

By the term "fusion molecule" as it is used herein is meant a transducing molecule and usually a protein or peptide sequence covalently linked (i.e. fused) to a cytotoxic domain by recombinant, chemical or other suitable method. If desired, the fusion molecule can be fused at one or several sites through a peptide linker sequence. That peptide sequence can include one or more sites for cleavage by a pathogen induced or host cell induced protease. Alternatively, the peptide linker may be used to assist in construction of the fusion molecule. The cytotoxic domain will usually include one potentially toxic molecule such a zymogen sometimes from between about 2 up to about 5 to 10 of such molecules. Specifically preferred fusion molecules are fusion proteins.

As noted, components of the fusion proteins disclosed herein, e.g., transducing amino acid sequence, cytotoxin domain, protease cleavage site(s) and any peptide linkers, can be organized in nearly any fashion provided that the fusion protein has the function for which it was intended. In particular, each component of the fusion protein can be spaced from another component by at least one suitable peptide linker sequence if desired. Additionally, the fusion proteins may include tags, e.g., to facilitate identification anchor purification of the fusion protein. More specific fusion proteins are described below.

Preferred peptide linker sequences typically comprise up to about 20 or 30 amino acids, more preferably up to about 10 or 15 amino acids, and still more preferably from about 1 to 5 amino acids. The linker sequence is generally flexible so as not to hold the fusion molecule in a single rigid conformation. The linker sequence can be used, e.g., to space the DNA binding protein from the fused molecule. Specifically, the peptide linker sequence can be positioned between the protein transduction domain and the cytotoxic domain, e.g., to chemically cross-link same and to provide molecular flexibility.

The term "misfolded" as it relates to the fusion proteins is meant a protein that is partially or completely unfolded (i.e. denatured). A fusion protein can be partially or completely misfolded by contact with one or more chaotropic agents as discussed below. More generally, misfolded fusion proteins disclosed herein are representative of a high Gibbs free energy ($\Delta G$) form of the corresponding native protein. Preferred are misfolded fusion proteins that are fully soluble in aqueous solution. In contrast, a native fusion protein is usually correctly folded, it is fully soluble in aqueous solution, and it has a relatively low $\Delta G$. Accordingly, that native fusion protein is stable in most instances.

It is possible to detect fusion protein misfolding by one or a combination of conventional strategies. For example, the misfolding can be detected by a variety of conventional biophysical techniques including optical rotation measurements using native (control) and misfolded molecules. As noted, preferred administration of the anti-pathogen system involves transduction of misfolded fusion proteins in vitro and in vivo. Without wishing to be bound to theory, it is believed that after transduction of the fusion protein into cells, misfolded fusion proteins are significantly refolded, e.g., by chaperonens, sufficient to produce a fusion protein than can be activated in response to pathogen infection.

By the term "fully soluble" or similar term is meant that the fusion molecule and particularly a fusion protein that is not readily sedimented under low G-force centrifugation (e.g. less than about 30,000 revolutions per minute in a standard centrifuge) from an aqueous buffer, e.g., cell media. Further, the fusion molecule is soluble if the it remains in aqueous solution at a temperature greater than about 5–37° C. and at or near neutral pH in the presence of low or no concentration of an anionic or non-ionic detergent. Under these conditions, a soluble protein will often have a low sedimentation value e.g., less than about 10 to 50 svedberg units.

Aqueous solutions referenced herein typically have a buffering compound to establish pH, typically within a pH range of about 5–9, and an ionic strength range between about 2 mM and 500 mM. Sometimes a protease inhibitor or mild non-ionic detergent is added. Additionally, a carrier protein may be added if desired such as bovine serum albumin (BSA) to a few mg/ml. Exemplary aqueous buffers include standard phosphate buffered saline, tris-buffered saline, or other well known buffers and cell media formulations.

A "polypeptide" refers to any polymer preferably consisting essentially of any of the 20 natural amino acids regardless of its size. Although the term "protein" is often used in reference to relatively large proteins, and "peptide" is often used in reference to small polypeptides, use of these terms in the field often overlaps. The term "polypeptide" refers generally to proteins, polypeptides, and peptides unless otherwise noted.

By the term "potentially toxic molecule" is meant an amino acid sequence such as a protein, polypeptide or peptide; a sugar or polysaccharide; a lipid or a glycolipid, glycoprotein, or lipoprotein that can produce the desired toxic effects as discussed herein. Also contemplated are potentially toxic nucleic acids encoding a toxic or potentially toxic protein, polypeptide, or peptide. Thus, suitable molecules include regulatory factors, erzymes, antibodies, or drugs as well as DNA, RNA, and oligonucleotides. The potentially toxic molecule can be naturally-occurring or it can be synthesized from known components, e.g., by recombinant or chemical synthesis and can include heterologous components. A potentially toxic molecule is generally between about 0.1 to 100 KD or greater up to about 1000 KD, preferably between about 0.1, 0.2, 0.5, 1, 2, 5, 10, 20, 30 and 50 KD as judged by standard molecule sizing techniques such as centrifugation or SDS-polyacrylamide gel electropheresis.

As used herein, the term "cell" is intended to include any primary cell or immortalized cell line, any group of such cells as in, a tissue or an organ. Preferably the cells are of mammalian and particularly of human origin, and can be infected by one or more pathogens. A "host cell" in accord with the invention can be an infected cell or it can be a cell such as *E. coli* that can be used to propagate a nucleic acid described herein.

The present anti-pathogen system is suitable for in vitro or in vivo use with a variety of cells that are infected or that may become infected by one or more pathogens.

As an illustration of the use of the anti-pathogen system, a cultured cell can be infected by a pathogen of a single serotype. The infected cell is then contacted by a specified fusion protein in vitro. As discussed previously, the fusion protein is configured so that the cytotoxic domain is activated in the presence of one or more proteases induced by the pathogen infection. After providing for transduction into the cell (generally less than about 30 minutes), the cells are allowed to cleave the fusion protein for a time period of about up to about 2 to 24 hours, typically about 18 hours. After this time, the cells are washed in a suitable buffer or cell medium and then evaluated for viability. The time allotted for cell killing or injury by the fusion protein will vary with the particular cytotoxic domain chosen. However viability can often be assessed after about 2 to 6 hours up to about 24 hours. As will be explained in more detail below, cell viability can be readily measured and quantified by monitoring uptake of certain well-known dyes (e.g., trypan blue) or fluors.

As noted above, the anti-pathogen system is flexible and can be provided in formats that are tailored for a specific use. For example, the system can be provided with two fusion proteins in which the first fusion protein includes a transduction domain and a cytotoxic domain, and the second fusion protein includes a transducing domain and a pathogen-induced or host cell induced protease.

Cells transduced by the fusion molecules of the present invention can be assayed for viability by standard methods. In one approach, cell viability can be readily assayed by measuring DNA replication following or during transduction. For example, a preferred assay involves cell uptake of one or more detectably-labeled nucleosides such as radio-labelled thymidine. The uptake can be conveniently measured by several conventional approaches including trichloroacetic acid (TCA) precipitation followed by scintillation counting. Other cell viability methods include well know trypan blue exclusion techniques.

As noted, fusion molecules of the present invention are efficiently transduced into target cells or groups of such cells. Transduction efficiency can be monitored and quantified if desired by one or a combination of different strategies.

For example, one approach involves an in vitro assay that measures uptake of the fusion protein by the cell. The assay includes detectably-labeling the fusion protein with, e.g., a radioactive atom, fluorescent, phosphorescent, or luminescent tag (e.g., fluorescein, rhodamine or FITC) and then measuring uptake of the labeled fusion protein. Alternatively, the fusion protein can be labeled with an enzyme capable of forming a detectable label such as horseradish peroxidase, β-galactosidase, chloramphenicol acetyl transferase or luciferase. In a preferred approach, it is possible to genetically fuse a desired fusion protein to the well-known green fluorescent protein (GFP) and then assaying the fusion protein. Uptake can be measured by several conventional methods such as by quantifying labeled cells in a standard cell sorter (e.g., FACS), by fluorescence microscopy or by autoradiography. See generally Sambrook et al. and Ausubel et al. infra for disclosure relating to the assays.

Preferred fusion proteins of the invention are capable of transducing at least about 20%, to 80%, and more preferably at least about 90%, 95%, 99% up to 100% of the total number of target cells as determined by any conventional methods for monitoring protein uptake by cells and particularly the FACS or related microscopical techniques. The total number of target cells can be estimated by standard techniques.

As noted, the present invention pertains to fusion proteins and nucleic acids (e.g., DNA) encoding the fusion proteins. When the cytotoxic domain is a polypeptide sequence, the term fusion protein is intended to describe at least two polypeptides, typically from different sources, which are operatively linked. With regard to the polypeptides, the term "operatively linked" is intended to mean that the two polypeptides are connected in manner such that each polypeptide can serve its intended function. Typically, the two polypeptides are covalently attached through peptide bonds. As discussed, the two polypeptides may be separated by a peptide linker if desired.

The fusion proteins described herein are preferably produced by standard recombinant DNA techniques. For example, a DNA molecule encoding the first polypeptide can be ligated to another DNA molecule encoding the second polypeptide. In this instance, the resultant hybrid DNA molecule can be expressed in a suitable host cell to produce the fusion protein. The DNA molecules are ligated to each other in a 5' to 3' orientation such that, after ligation, the translational frame of the encoded polypeptides is not altered (i.e., the DNA molecules are ligated to each other in-frame). The resulting DNA molecules encode an in-frame fusion protein.

The components of the fusion protein can be organized in nearly any order provided each is capable of performing its intended function. For example, in one embodiment, the protein transduction domain is adjacent to a pathogen-specific protease cleavage site included within the cytotoxic domain. Additionally, the cytotoxic domain can be flanked by pathogen-specific protease cleavage sites, one or both of which can also be adjacent to the protein transduction domain. The present invention also contemplates circular fusion proteins.

Preferred cytotoxic domains including the pathogen-specific cleavage sites will have sizes conducive to the function for which those domains are intended. In particular, preferred cytotoxlic domains can be at least about 0.1, 0.2, 0.5, 0.75, 1, 5, 10, 25, 30, 50, 100, 200, 500 kD, up to about 1000 kD or more. It should be apparent that the size of the cytotoxic domain usually dominates the size of the fusion protein. Preferred pathogen-specific cleavage sites will be between about 4 to about 30 or 40, preferably about 8 to about 2.0 and more preferably about 14 amino acids in length. See Table I, below. The pathogenic-specific protease cleavage sites can be made and fused to the cytotoxic domain by a variety of methods including well-known chemical cross-linking methods. See e.g., Means, G. E. and Feeney, R. E. (1974) in *Chemical Modification of Proteins*, Holden-Day. See also, S. S. Wong (1991) in *Chemistry of Protein Conjugation and Cross-Linking*, CRC Press. However it is generally preferred to use recombinant manipulations to make the in-frame fusion protein.

As noted, a fusion molecule in accord with the invention can be organized in several ways. In an exemplary configuration, the C-terminus of the transduction domain is operatively linked to the N-terminus of the cytotoxic domain. That linkage can be achieved by recombinant methods if desired. However, in another configuration, the N-terminits of the transduction domain is linked to the C-terminus of the cytotoxic domain. Within the cytotoxic domain, the N-terminus of a first pathogen-specific protease cleavage site can be operatively linked to the C-terminus of the transduction domain and the C-terminus of the protease cleavage site can be operatively linked to the N-terminus of a potentially toxic molecule. In yet another configuration, the C-termints of the cytotoxic domain can be linked to the N-terminus of a second pathogen-specific protease cleavage site the same or different from the first pathogen-specific site. Preferably, the first and second pathogen-cleavage sites will be specifically cleaved by the same protease induced by the pathogen infection.

Alternatively, or in addition, one or more additional protease cleavage sites can be inserted into the potentially toxic molecule as needed.

Preferred fusion proteins in accord with the present invention typically include operatively linked in sequence (N to C terminus): 1) a transduction domain/one or more pathogen-specific protease cleavage sites/and a potentially toxic molecule; 2) a transduction domain/a pathogen specific protease cleavage site/and a zymogen; and 3) a transduction domain/a first pathogen specific protease cleavage site/a first zymogen subunit/a second pathogen specific protease cleavage site/ and a second zymogen subunit. In addition, one or more protein tags such as EE, HA, Myc, and polyhistidine, particularly 6Xhis, can be fused to the N-terminus of the transduction domains as desired, e.g., to improve solubility or the facilitate isolation and identification of the fusion protein. See Examples below.

Although generally not preferred, it is possible to operatively link a polypeptide sequence to the fusion proteins to promote transport to a cell nucleus. Amino acid sequences which, when included in a protein, function to promote transport of the protein to the nucleus are known in the art and are termed nuclear localization signals (NLS). Nuclear localization signals typically are composed of a stretch of basic amino acids. When attached to a heterologous protein (e.g., a fusion protein of the invention), the nuclear localization signal promotes transport of the protein to a cell nucleus. The nuclear localization signal is attached to a heterologous protein such that it is exposed on the protein surface and does not interfere with the function of the protein. Preferably, the NLS is attached to one end of the protein, e.g. the N-terminus. The SV40 nuclear localization signal is a non-limiting example of an NLS that can be included in a fusion protein of the invention. The SV40 nuclear localization signal has the following amino acid sequence: Thr-Pro-Pro-Lys-Lys-Lys-Lys-Arg-Lys-Val (SEQ ID NO: 45). Preferably, a nucleic acid encoding the nuclear localization signal is spliced by standard recombinant DNA techniques in-frame to the nucleic acid encoding the fusion protein (e.g., at the 5' end).

As noted above, a fusion protein of the invention is composed, in part, of a first polypeptide, sometimes. referred to herein as a protein transduction domain, transduction domain, transducing protein, or "PTD", which provides for entry of the fusion protein into the cell. Peptides having the ability to provide entry of a coupled peptide into a cell are known and include those mentioned previously such as TAT, Antennapedia homeodomain, referred to as "Penetratin" Ala-Lys-Ile-Trp-Phe-Gln-Asn-Arg-Arg-Met-Lys-Trp-Lys-Lys-Glu-Asn (SEQ ID. NO: 1) (Derossi et al., *J. Bio. Chem.*, 269:10444 (1994)) and HSV VP22 (Elliot and O'Hare, *Cell*, 88:223 (1997)).

Illustrative of a transducing protein is a TAT fragment that includes at least the TAT basic region (amino acids 49–57 of naturally-occurring TAT protein). TAT fragments can be between about 9, 10, 12, 15, 20, 25, 30, or 50 amino acids in length up to about 86 amino acids in length. The TAT fragments preferably are deficient in the TAT cysteine-rich region (amino acids 22–36 of naturally-occurring TAT protein) and the TAT exon 2 encoded by a carboxy-terminal domain (amino acids 73–86 of naturally-occurring TAT protein). A TAT transduction domain has the following amino acid sequence: YGRKKRRQRRR (SEQ ID. NO: 2). That amino acid sequence will sometimes be referenced herein as a "minimal TAT sequence". See U.S. Pat. No. 5,674,980 and references cited therein for disclosure relating to TAT structure. See also Green, M. and Lowenstein, P. M. (1988) for the TAT sequence.

Various transduction enhancing modifications of the TAT fragment are contemplated as discussed above and in the Examples which follow. For example, the protein transduction domain of the fragment can be flanked by glycine residues to allow for free rotation. See e.g., FIG. 2 of the drawings. Alternatively, other amino acid sequences and particularly neutral and/or hydrophilic residues may be added to the TAT fragment as desired. Protein tags may be added to a TAT fragment such as those known in the field. Examples of such protein tags include 6XHis, HA, EE and Myc. In general, the size of the modified TAT fragment will be at least 10, 12, 15, 20, 25, 30, 50, 100, 200, to about 500 amino acids in length.

The transduction domain of the fusion protein can be obtained from any protein or portion thereof that can assist in the entry of the fusion protein into the cell. As noted, preferred proteins include, for example TAT, Antennapedia homeodomain and HSV VP22 as well as non-naturally-occurring sequences. The suitably of a synthetic protein transduction domain can be readily assessed, e.g., by simply testing a fusion protein to determine if the synthetic protein transduction domain enables entry of the fusion protein into cells as desired.

By the term "synthetic protein" or like term a non-naturally occurring amino acid sequence which is made be recombinant methods or methods involving chemical peptide synthesis.

Numerous variants of transducing TAT proteins have been described in the field. These variants can be used in accord with the present invention. See e.g., U.S. Pat. No. 5,652,122 which reports methods of making and using transducing TAT proteins, the disclosure of which is incorporated by reference.

Additional transduction domains and particularly transducing proteins can be readily identified by conventional techniques. For example, in one approach, a candidate transduction domain such as a desired TAT fragment is fused to a desired cytotoxic domain using standard recombinant manipulations to form the in-frame fusion protein. The fusion protein is subsequently detectably-labeled with, e.g., a radioactive atom or fluorescent label such as FITC. The detectably-labeled fusion protein is then added to cells as described above and the levels of the fusion protein are measured. A preferred transduction domain will be capable of achieving an intracellular concentration of the fusion protein of between about 1 picomolar to about 100 micromolar, preferably about 50 picomolar to about 75 micromolar, and more preferably about 1 to about 100 nanomolar.

Particularly contemplated transducing proteins are those obtained by targeted mutagenesis of known transducing proteins or fragments, e.g., TAT, VP22 or the Antennapedia homeodomain sequences mentioned above. Typically, the mutagenized transducing protein will exhibit at least about 2, 3, 4, 5, 10, 20, 30, 40 or 50 fold better transduction of a desired fusion protein when compared to that same fusion protein comprising a corresponding full-length transducing protein sequence.

Preferred transduction proteins in accord with this invention are Class I amino acid sequences, preferably peptide sequences, that include at least a peptide represented by the following, general formula: $B_1$-$X_1$-$X_2$-$X_3$-$B_2$-$X_4$-$X_5$-$B_3$ (SEQ ID NO: 42); wherein $B_1$, $B_2$, and $B_3$ are each independently a basic amino acid, the same or different; and $X_1$, $X_2$, $X_3$, $X_4$ and $X_5$ are each independently an alpha-helix enhancing amino acid the same or different. Typically these sequences are synthetic.

The term "basic amino acid" or like term as used herein refers to an amino acid having a basic residue such is a primary, secondary or tertiary amine, or a cyclic group containing nitrogen ring member. Preferred basic amino acids are lysine (Lys) and arginine (Arg), with arginine being particularly preferred. Histidine (His) also can be a suitable basic amino acid.

The term "alpha-helix enhancing" amino acid or like term is meant an amino acid which has a recognized tendency to form or stabilize an alpha-helix as measured by assays well-known in the, field. See generally O'Neil, K. T. and DeGrado, W. F. (1990) *Science* 250: 646 and references cited therein for such an assay. Preferred alpha-helix enhancing amino acids include alanine (Ala), arginine (Arg), lysine (Lys), leucine (Leu), and methionine (Met). A particularly preferred alpha-helix enhancing amino acid is alanine. By the term "substantial alpha-helicity" is meant that a particular peptide has a recognizable alpha-helical structure as determined, e.g., by a helical wheel diagram or other conventional means.

In one embodiment, the peptide is represented by the formula $B_1-X_1-X_2-X_3-B_2-X_4-X_5-B_3$ (SEQ ID NO: 42); wherein at least one of $B_1$, $B_2$, or $B_3$ is arginine, preferably all of $B_1$, $B_2$ and $B_3$ is arginine; and $X_1$, $X_2$, $X_3$, $X_4$ and $X_5$ are each independently an alpha-helix enhancing amino acid the same or different. Preferably at least one of $X_1$, $X_2$, $X_3$, $X_4$ or $X_5$ is an alanine, more preferably all of $X_1$, $X_2$, $X_3$, $X_4$ and $X_5$ are alanine. In another embodiment, the peptide is represented by the formula $B_1-X_1-X_2-X_3-B_2-X_4-X_5-B_3$ (SEQ ID NO: 42); wherein $B_1$, $B_2$, and $B_3$ are each independently a basic amino acid, the same or different; and at least one of $X_1$, $X_2$, $X_3$, $X_4$ or $X_5$ is alanine, preferably all of $X_1$, $X_2$, $X_3$, $X_4$ and $X_5$ each is alanine. In these embodiments, basic amino acid residues such as arginine are substantially aligned along at least one face of the peptide, typically along one face.

Additionally preferred transduction proteins in accord with this invention are synthetic amino acid sequences, preferably peptide sequences, that include at least a peptide represented by the following general formula: $B_1-X_1-X_2-B_2-B_3-X_3-X_4-B_4$ (SEQ ID NO: 43); wherein $B_1$, $B_2$, $B_3$, and $B_4$ are each independently a basic amino acid, the same or different; and $X_1$, $X_2$, $X_3$, and $X_4$ are each independently an alpha-helix enhancing amino acid the same or different. In a one embodiment, at least one of $B_1$, $B_2$, $B_3$, or $B_4$ is arginine, preferably all of $B_1$, $B_2$, $B_3$, and $B_4$ are arginine; and the $X_1$, $X_2$, $X_3$, and $X_4$ are each independently an alpha-helix enhancing amino acid the same or different. In another embodiment, each of the $B_1$, $B_2$, $B_3$, and $B_4$ are independently a basic amino acid, the same or different; and at least one of $X_1$, $X_2$, $X_3$, or $X_4$ is an alanine, preferably all of $X_1$, $X_2$, $X_3$, and $X_4$ are alanine residues. In these embodiments, basic amino acid residues such as arginine are substantially aligned along at least one face of the peptide, typically along one face.

By the term "substantial alignment" of a basic amino acid residue or like term is meant that the basic amino acid residue is positioned with respect to at least one other basic amino acid residue so that each residue is spaced from the other on a conceptualized alpha-helix by between about 3 to about 4 Angstroms, preferably about 3.6 Angstroms. Alignment can be performed by several conventional methods including inspection of standard helical wheel diagrams such as those shown below in FIG. 7. Preferred transduction domains exhibit between about 2, 3, 4, 5, 6, or about 7 up to about 10 substantially aligned basic amino acid residues.

More preferred transduction proteins of this invention include at least a peptide represented by the following specific peptide sequences: YARKARRQARR (SEQ ID NO. 3), YARAAARQARA (SEQ ID NO. 4), YARAARAARR (SEQ ID NO. 5), YARAARRAARA (SEQ ID NO. 6), YARRRRRRRRR (SEQ ID NO. 7), and YAAARRRRRRR (SEQ ID NO. 8). Particularly preferred are transducing peptide sequences consisting), of the following peptide sequences: YARKARRQARR (SEQ ID NO. 3), YARAAARQARA (SEQ ID NO. 4), YARAARRAARR (SEQ ID NO. 5), YARAARRAARA (SEQ ID NO. 6), YARRRRRRRRR (SEQ ID NO. 7), and YAAARRRRRRR (SEQ ID NO. 8).

Additional transduction proteins of this invention are amino acid sequences, preferably synthetic sequences, that include at least one amino acid modification in at least amino acids 49 to 56 of TAT. For example, in one embodiment, the synthetic peptide sequences include at least amino acids 47 to 56, 48 to 56, 47 to 57, 48 to 57, or 49 to 57 of TAT which TAT sequence has been modified to increase the alpha-helicity of that TAT sequence relative to a suitable TAT control sequence. Preferably, the TAT sequence includes at least one amino acid substitution with an alpha-helix enhancing amino acid such as alanine.

Additional transducion proteins are amino acid sequences, preferably synthetic peptide sequences that include at least amino acids 47 to 56, 48 to 56, 47 to 57, 48 to 57, or 49 to 57 of TAT which TAT sequence has been modified so that two or more basic amino acids such as arginine are substantially aligned along at least one face of that TAT sequence. The alignment can be facilitated by a variety of approaches including visualizing the TAT sequence as an alpha-helix on a helical wheel. See FIG. 7 which follows.

Further transduction proteins of this invention are peptide sequences that include at least amino acid; 49 to 56 of TAT, preferably 47 to 56, 48 to 56, 49 to 56, 47 to 57, 48 to 57, or 49 to 57 of TAT, in which the TAT sequence includes at least one amino acid substitution with an alpha-helix enhancing amino acid. In this embodiment, the amino acid substitution is selected to align substantially two or more arginine residues along at least one face of that TAT sequence, preferably alone one face of the TAT sequence. In one embodiment, preferably about 2, 3, 4, or 5 arginine residues are substantially aligned along at least one face of the helix, more specifically along one face of the helix For example, about 1, 2, 3, 4, or 5 amino acid residues up to about 6 amino acids residues in the TAT sequence can be substituted with an alanine residue to enhance alpha-helicity and to align the arginine residues on at least one face of the helix.

Additional transduction proteins in accord with this invention include amino acid sequences that comprise at least a transducing portion of the Antp sequence (SEQ ID NO 10; see Table 2 below), preferably the Antp sequence which has been modified along lines described above for specified TAT sequences. In particular, the modifications can include at least one suitable amino acid substitution, deletion or addition that has been selected to enhance the alpha-helicity of the transduction protein, to align basic amino acid residues (e.g., Arginine) along at least one face of the Antp sequence, or both. Illustrative are transduction proteins that include the Antp sequence (SEQ ID NO. 10) in which the Antp sequence has been modified to include at least one amino acid modification sufficient to increase transduction efficiency of the protein by between about 2, 5 or 10 up to 100 or more fold compared to a suitable control peptide, e.g., the Antp sequence (SEQ ID NO. 10).

Additionally preferred are class II transducing amino acid sequence as described above. In one embodiment, the class II sequence is a peptide represented by the following formula: $X_1-X_2-R$ $X_3-(P/X_4)-(B/X_5)-B-(P/X_6)-X_4-B-(B/X_7)$ (SEQ ID NO: 44), wherein each of $X_1,X_2,X_3,X_4,X_5,X_6,X_7$ is an alpha helical promoting residue the same or different;

each of (P/X$_4$) and (P/X$_6$) are independently proline or an alpha helical promoting residue; B is a basic amino acid residue; (B/X$_5$) (B/X$_7$) are each independently B or an alpha helical promoting residue; and R is arginine (Arg). A preferred alpha helical promoting residue is alanine (Ala). Preferred basic amino acid residues are arginine (Arg), lysine (Lys), especially Arg. Particularly preferred class II transducing amino acid sequences include at least one proline residue, usually between from about one to three residues.

More specifically preferred class II peptide sequences are provided in Example 13 below (SEQ ID Nos. 36–41).

Molecular weights of the transduction domains described herein will vary according to parameters such as intended use and transduction efficiency desired. Generally, the transduction domain will exhibit a molecular weight of between from about 1, 2, 3, 5, 10, 20 to about 50 kDa as judged by SDS-PAGE gel electrophoresis or other suitable assay. Specifically preferred transduction domains are described more fully below and in the examples which follow.

As noted, preferred transduction domains in accord with the present invention will exhibit enhanced transduction efficiency. That increase can be evaluated by one or a variety of standard techniques such as those specifically described below. In one general approach sometimes referred to herein as a transduction efficiency assay or similar term, the transduction efficiency is determined by reference to a control assay in which one or more suitable control molecules are transduced into cells in parallel with a desired transduction protein. Preferably, transduction rate and intracellular amounts of a specified transduction domain are measured and compared to the control molecule. Illustrative control molecules suitable include amino acids 47 to 57 of TAT (SEQ ID NO: 1), amino acids 49 to 57 of TAT, and the Antp sequence (SEQ ID NO: 10).

Two or more protein transduction domains of this invention, e.g., about 2, 3, 4, 5, 6, up to about 10 or more protein transduction domains, can be covalently linked to a desired molecule to be transduced. In this embodiment, the protein transduction domains can be linked in tandem or can be separated by at least one suitable peptide linker as desired.

Preferred transduction proteins of this invention exhibit an increase in transduction efficiency of between about 5 to 10 up to 100 or more fold when compared to a suitable control sequence, e.g., the minimal TAT sequence or other suitable control molecule. Examples of preferred transduction assays are described below in Example 7.

The transduction proteins of the present invention can be made by a variety of conventional methods. For example, DNA coding for a desired transduction protein can be obtained by isolating DNA from natural sources or by known synthetic methods, e.g. the phosphate triester method. See, e.g., *Oligonucleotide Synthesis*, IRL Press (M. Gait, ed., 1984). Synthetic oligonucleotides also may be prepared using commercially available automated oligonucleotide synthesizers. The synthetic oligonucleotide encoding the transducing protein may be inserted into a variety of suitable vectors (e.g., pTAT Vector) and expressed in an appropriate host cell. See generally Ausubel et al. and Sambrook et al. infra.

As discussed, components of the fusion proteins can be linked in several ways. In one embodiment, the transduction domain of the fusion protein is operatively linked to a cytotoxic domain (sometimes referred to herein as "CD"). As also discussed, the function of the cytotoxic domain in this example is to produce a cytotoxin that can kill or injure infected cells under specified conditions. The cytotoxic domain is transduced into the cell as part of the fusion molecule, and it is specifically intended to be released from that fusion molecule in the presence of one or more specified proteases induced by the pathogen infection. In some instances, release of the cytotoxin will be accompanied by further processing or maturation by the hosting cell. A preferred method of operatively linking the transduction domain and the cytotoxic domain is to use a nucleic acid sequence which encodes same ligated together to form an in-frame genetic fusion protein.

As noted previously, the present invention is compatible with a variety of cytotoxic domains. Preferred cytotoxic domains include potentially toxic molecules such as known zymogens. In general, most zymogens exhibit insignificant catalytic activity. However, once activated by protein modification and particularly proteolysis at one or more protease cleavage sites, the zymogens are converted into mature enzymes. In instances where the conversion (maturation) includes proteolysis, the cleavage occurs at site specific locations in the zymogen. Sometimes fragments released from the zymoger, are themselves catalytically active and upon release, further process the immature enzyme to a less immature or fully mature form. Zymogens including such fragments are often referred to as autocatalytic enzymes. In other cases however, the fragments are devoid of significant catalytic activity and must be cleaved to form the mature enzyme. A particular catalytic fragment can be naturally-associated with the zymogen or it can be recombinantly added to zymogen in accord with standard techniques to form a heterologous zymogen. Naturally-occuring protease cleavage, sites in the zymogen usually serve to demarcate subunits within the zymogen. These can be replaced or added to in accordance with methods discussed herein.

Particular zymogens for use in accord with this invention include those associated with apoptosis, particularly cysteinyl aspartate-specific proteinases (caspases) and particularly caspase-3 (CPP32, apopain, Yama), caspases-5 (ICE$_{rel}$-III, TY), caspase-4(ICE$_{rel}$-II TX, ICH-2), caspase-1 (ICE), caspase-7 (Mch3, ICE-LAP3, CMH-1), caspase-6 (Mch2), caspase-8 (MACH, FLICE, Mch5), caspase-10 (Mch4), caspase-2 (ICH-1), caspase-9 (ICH-LAP6, Mch6) and catalytically active fragments thereof that are relatively inert zymogen fragments.

In particular, activation of Caspase-3 (Casp3) has previously been shown to be a rubicon of apoptosis by cleavage of the inhibitor of caspase-activated DNAse (ICAD) resulting in the activation of CAD and ultimately cell death. See e.g., Salvesen, G. S., et al., Caspases: intracellular signaling by proteolysis. *Cell* 91:443 (1997); Henkart, P. A., ICE family proteases: mediators of all apoptotic cell death? *Immunity* 4: 195 (1996); Cohen, G. M., Caspases: the executioners of apoptosis. *J. Biochem.* 326: 1 (1997); Woo, M. et al., Essential contribution of caspase 3/Casp3 to apoptosis and its associated nuclear changes, *Genes & Dev.* 12: 806 (1998); Enari, M., et al., A caspase-activated DNase that degrades DNA during apoptosis, and its inhibitor ICAD. *Nature* 391: 43 (1998); Liu, X., et al., DFF40 induces DNA fragmentation and chromatin condensation during apoptosis. *Proc. Natl. Acad. Sci. USA* 15:8461 (1998). In addition, activated Casp3 can catalyze the activation of inactive Casp3, thereby further amplifying the apoptotic signal.

Figure 9A:
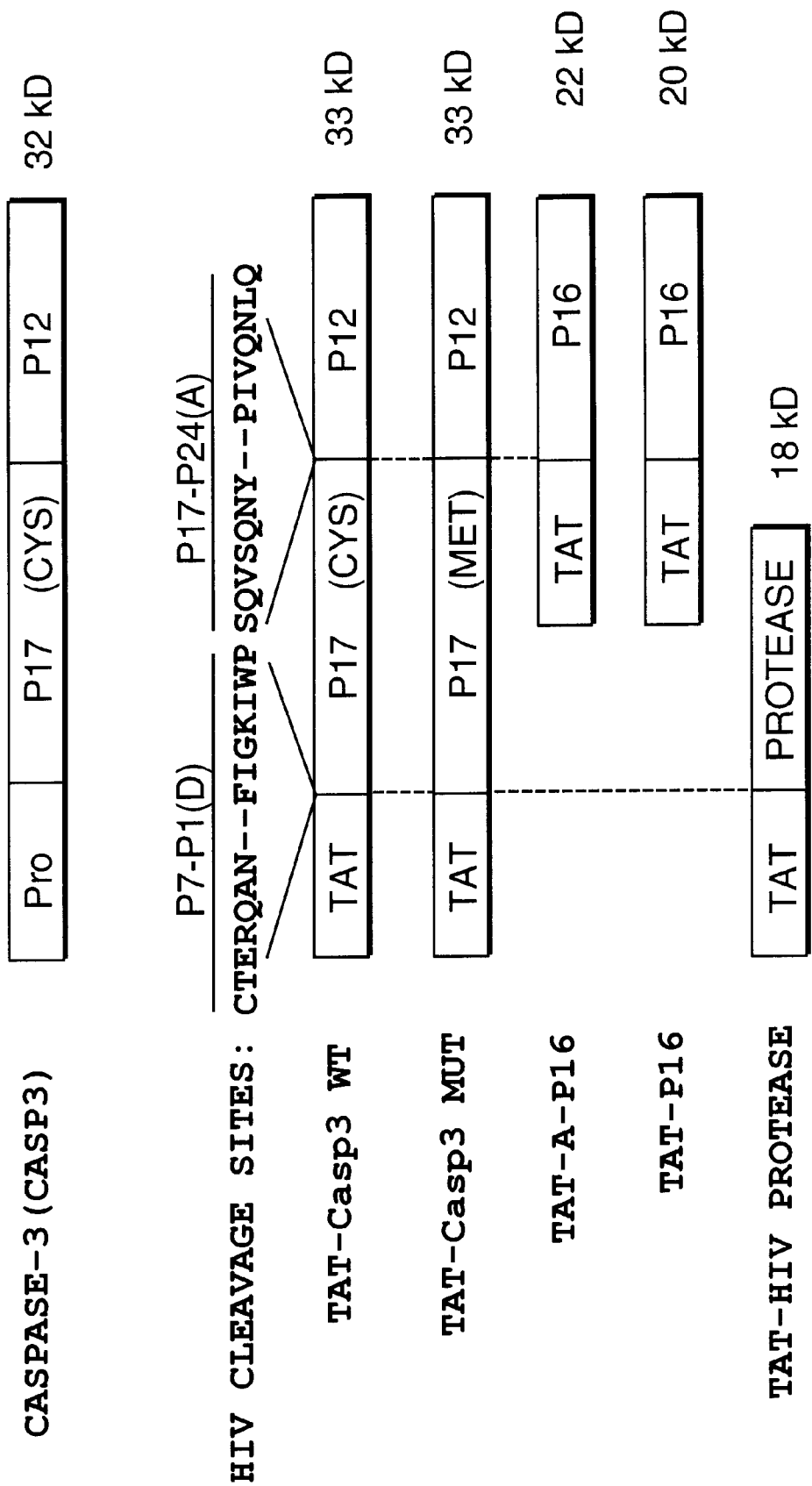

The structure of the Casp3 zymogen is known to include a N' terminal Pro domain, followed by a caspase cleavage recognition site, then the p 17 domain that contains the catalytic Cys residue, a second caspase cleavage site and finally the p12 domain (see FIG. 9A). The zymogen form of Casp3 remains inactive; however, during apoptotic signaling, it is cleaved by upstream caspases, such as Caspase-8 in T cells, resulting in loss of the Pro domain and an active p17:p12 heterotetramer. See Woo, M. et al., (supra).

Example 12 below illustrates a specific inactivation of the HIV viral replication machinery to treat HIV infected cells. The strategy exploits the HIV Protease to kill the infected cell while leaving uninfected cells unharmed. As will be more fully described in Example 12, a modified Caspase 3 protein, TAT-Casp3, was made. This fusion protein transduces into ~100% of infected and uninfected cells. However, due to substitution of endogenous cleavage sites for HIV proteolytic cleavage sites, TAT-Casp3 Lis only specifically activated by HIV Protease in infected cells, resulting in apoptosis, whereas in uninfected cells it remains in the inactive zymogen form. See Ratner, L. et al., Complete nucleotide sequence of the AIDS virus, HTLV-III. *Nature* 313: 277 (1985). By substitution of proteolytic cleavage sites, this strategy could be applied to other pathogens encoding specific proteases, such as Hepatitis C virus, cytomegalovirus and malaria. See Rice, C. M.,Flaviviridae: The viruses and their replication, in *Fields Virology* (eds Fields, B. N., Knipe, D. M., & Howley, P. M.) 931–960 (Lippincott-Raven Publishers, Philadelphia, 1996); Welch, A. R. et al., Herpesvirus maturational protease, assemblin: identification of its gene, putative active site domain, and cleavage site. *Proc. Natl. Acad. Sci. USA* 88: 10792 (1991); Francis, S E, et al., Hemoglobin metabolism in the malaria parasite Plasmodium falciparum. *Ann. Rev. Microbiol.* 51: 97 (1997).

See also Ratner, L. et al. (1985), supra for disclosure of the complete nucleotide sequence of the AIDS virus. See also, Wong, J. K (1997) *Science* 278: 1291 and Finzi, D. et al. (1997) *Science* 278: 1295; for disclosure relating to treatment of HIV infections.

See the following references for more specific information relating to the structure and function of the HIV virus: Wu, X. et al. *EMBO J.* (1997) 16: 5113; Lillehoj, E. P. et al. (1998); Kohl, N. E. et al. (1988) *PNAS (USA)* 85: 4686; Gottlinger, H. G., et al. (1989), *PNAS (USA)* 86: 5781.

In particular, Example 12 shows production of a transducible, modified apoptotic promoting caspase-3 protein (ie. TAT-Casp3), that substitutes HIV proteolytic cleavage sites for endogenous sites. Further, the fusion molecule efficiently transduces into ~100% of cells, but remains inactive in uninfected cells. In HIV infected cells, TAT-(Casp3 becomes processed into an active form by HIV protease resulting in apoptosis of the infected cell. As will be apparent from the accompanying examples and discussion, this specific strategy is generally applicable and could be used to combat other pathogens encoding specific proteases, such as Hepatitis C virus, cytomegalovirus and malaria.

An additionally preferred zymogen is granzyme B.

An additionally preferred zymogen is Bid. The Bid protein has been reported to be a 20 kDa protein related to the Bcl2/Bax family of apoptotic regulatory proteins. See Luo et al. (1998) *Cell* 94: 481; Li et al. (1998) *Cell* 94: 491; Wang et al. (1996) *Genes & Dev.* (1996) 10: 2859. The murine Bid sequence can be found in GenBank, accession number: U75506; NID: g1669513. See Example 11.

As noted previously, it has been found that mass action enhances the activity of certain embodiments of the anti-pathogen system. More particularly, it is believed that it is possible to administer the anti-pathogen system in many instances at extremely low doses (i.e., nanomoler levels). This feature can be particularly advantageous as it can enhance cell (and patient) tolerance for the anti-pathogen system.

More specifically, cleavage of the cytotoxic domain appears to draw additional fusion molecules into infected cells, thereby resulting in specific concentration of the cytotoxic domain and the cytotoxin in those infected cells. That concentration can be particularly significant with some cytotoxins, particularly those that require concentration to exhibit optimal effect. Illustrative examples of such cytotoxins include those obtained from zymogens of blood coagulation proteases such as thrombin and fibrin; trypsin, chymotrypsin, diphtheria toxin, ricin, shiga toxin, abrin, cholera toxin, saporin, pseudomonas exotoxin (PE), pokeweed antiviral protein, and gelonin. Additional examples include biologically active fragments of diphtheria toxin A chain and the ricin A chain.

Additionally preferred are cytotoxic domains which include proteins and particularly enzymes such as certain kinases and nucleoside deaminases associated with necrosis. Such enzymes include viral thymidine kinases, e.g., HSV thymidine kinase, and cytosine deaminase, respectively, as well as catalytically active fragments thereof.

Additionally preferred zymogens include those active at the surface of pathogen-infected cells such as a phospholipase enzyme, particularly phospholipase C.

Preferred zymogens and enzymes are generally capable of killing cells as determined by a suitable cell viability assay, e.g., Trypan blue exclusion. More preferred zymogens and enzymes have a molecular weights of between about 5, 10, 20, 30, 40, 50 kD up to about 100 to 500 kD or more as assayed by standard methods. The molecular weight can be determined by a number of conventional techniques such as SDS-PAGE gel electrophoresis, sedimentation centrifugation, and column chromatography.

A particularly preferred zymogen is caspase-3 (CPP32, apopain, Yama) or a catalytically active fragment thereof. See Examples 5–6 below.

Another particularly preferred enzyme is HSV-1 thymidine kinase or a catalytically active fragment thereof. See Example 8 below.

In general, preparation of the fusion molecules of the invention includes conventional recombinant steps involving, e.g., polymerase chain amplification reactions (PCR), preparation of plasmid DNA, cleavage of DNA with restriction enzymes, preparation of oligonucleotides, ligation of DNA, isolation of mRNA, introduction of the DNA into a suitable cell, and culturing of the cell. Additionally, the fusion molecules can be isolated and purified using chaotropic agents and well known electrophoretic, centrifugation and chromatographic methods. See generally, Sambrook et al., *Molecular Cloning: A Laboratory Manual* (2nd ed. (1989); and Ausubel et al., *Current Protocols in Molecular Biology*, John Wiley & Sons, New York (1989) for disclosure relating to these methods.

The following Table I provides examples of pathogen-specific proteases and protease cleavage sites for a number of known pathogens. The listed protease cleavage sites are illustrative of those which can be used in accord with the present invention.

TABLE I

| PATHOGEN | PROTEIN | SEQUENCE |
|---|---|---|
| HIV-1: | [1]GAG PROTEINS: | |
| | p17–p24 | SQVSQNY---PIVQNLQ (SEQ ID NO: 9) |
| | p7–p1 | CTERQAN---FLGKIWP (SEQ ID NO: 10) |
| | POL PROTEINS | |
| | P6'-Protease | GTVSFSF---PQITLWQ (SEQ ID NO: 46) |
| | Protease-RT | IGCTLNF---PISPIET (SEQ ID NO: 11) |
| Hepatitis C Virus (HCV): | [2]NS3-NS4A | CMSADLEVVF--STWVLVGGVL (SEQ ID NO: 47) |
| | NS4A-NS4B | YQEFDEMEEC---ASHLPYIEQG SEQ ID NO: 48) |
| | NS4B-NS5A | WISSECTTPC---SGSWLRDIWD (SEQ ID NO: 49) |
| | NS5A-NS5B | GADTEDVVCC--SMSYTWTGAL (SEQ ID NO: 50) |
| Malaria parasite: Plasmodium falciparum | [3]hemoglobinase | [4]WALERMF---LSFPTTK (SEQ ID NO: 51) |

[1,2]sites are listed as between cleaved proteins from larger polyproteins
[3]Recognizes a specific sequence in alpha hemoglobin.
[4]cut is between residues 33F–34L See also Gluzman, I. Y. et al., *J. Clin. Invest.*, 94:1602 (1994); Grakoui, A. et al., *J. of Virol.*, 67:2832 (1993); Kolykholov, A A. et al., *J. of Virol.*, 68:7525 (1994); and Barrie, K. A. et al., *Virology*, 219:407 (1996), the disclosures of which are incorporated by reference.

Additional pathogen-specific proteases and specified cleavage sites have been described and can be used in accord with the present anti-pathogen system.

For example, an HSV-1 maturational protease and protease cleavage site has been described. See e.g. Hall, M. R. T. and W. Gibson, *Virology*, 227:160 (1997); the disclosure of which is incorporated by reference.

Further, two aspartic proteinases referenced as plasmepsins I and II have been found in the digestive vacuole of *P. falciparum*. The corresponding proteinase cleavage sites have also been disclosed. See e.g., Moon, R. P., *Eur. J. Biochem.*, 244:552 (1997).

It will be appreciated that any of the above-referenced protease cleavage sites can be modified as desired (e.g., by site-specific mutagenesis) so long as the sites are specifically cleaved by the pathogen-specific protease for which they are intended. In some cases, it may be useful to determine the minimal sequence necessary for specific proteolytic cleavage, e.g., to optimize size and spatial considerations relating to the fusion protein. Such minimal sequences have been reported for many pathogen-specific protease cleavage sites. Alternatively, the minimal sequence for a desired proteolytic cleavage site can be readily obtained by mutagenesis, particularly deletion analysis and site specific multagenesis (e.g., alanine scanning mutagenesis). The modified cleavage site can be readily assayed in a standard protease cleavage assay as described below.

By the term "specifically cleaved" is meant that peptide bonds in a specified protease cleavage site are specifically broken (i.e. hydrolyzed) by one or more proteases induced by a pathogen infection. That is, the protease cleavage sites are not broken by proteases which naturally occur in an infected or uninfected cell such as those proteases referred to as housekeeping proteases. Specific cleavage of those protease cleavage sites can be monitored by a variety of techniques including SDS-polyacrylamide gel electrophoretic methods.

Preferred pathogen-specific protease cleavage sites include the HSV-1 protease cleavage sites p17-p24 (SQVSQNY—PIVQNLQ; SEQ ID NO. 9), p7-p1 (CTERQAN—FLGKIWP; SEQ ID NO. 10), and pr-RT (IGCTLNF—PISPIET; SEQ ID NO. 11). See Table I above and the Examples below.

Particularly preferred fusion proteins include operatively linked in sequence (N to C terminus): 1) TAT or a suitable transducing fragment thereof such as the minimal TAT sequence/the p17-p24 or protease-RT cleavage site/HSV TK; 2) TAT or a suitable transducing fragment thereof such as the minimal TAT sequence/the protease-RT cleavage site/the large domain of CPP32/the p17–24 cleavage site/and the small subunit of CPP32; 3) TAT or a suitable transducing fragment thereof such as the minimal TAT sequence/the p17-p24 or protease-RT cleavage site/and p16 wild-type or mutant form thereof and 4) TAT or a suitable transducing fragment thereof such as the minimal TAT sequence/(p7-p1) protease change site/HIV protease.

As mentioned above, it has been found that use of the present anti-pathogen system is facilitated by provding the fusion proteins in a misfolded form. For example, it has been found that native fusion proteins, when used in accord with the present anti-pathogen system, transduce much less efficiently than corresponding misfolded sequences. Thus, it is generally preferred that present fusion proteins be fully or partially denatured prior to use in the present anti-pathogen system. Methods for fully or partially denaturing proteins are well known and include treatment with recognized chaotropic agents such as urea, particularly about 6–8M urea, β-mercaptoethanol, DTT, SDS or other detergents, particularly ionic detergents. Further contemplated are physical treatments capable of denaturing proteins and polypeptides such as heating or sonication. Also envisioned are methods including one or more chaotropic agents and physical treatments.

In preferred methods of the invention, the fusion protein is introduced into the cell as a misfolded fusion protein. As mentioned previously, it has been found that the rate and quantity of fusion protein uptake into the cell is significantly enhanced when compared to the same fusion protein introduced into the same cells in a low energy and essentially native conformation.

The invention further provides nucleic acid sequences and particularly DNA sequences that encode the present fusion proteins. Preferably, the DNA sequence is carried by a vector suited for extrachromosomal replication such as a phage, virus, plasmid, phagemid, cosmid, YAC, or episome. In particular, a DNA vector that encodes a desired fusion protein can be used to facilitate preparative methods described herein and to obtain significant quantities of the fusion protein. The DNA sequence can be inserted into an appropriate expression vector, i.e., a vector which contains the necessary elements for the transcription and translation of the inserted protein-coding sequence. A variety of host-vector systems may be utilized to express the protein-coding sequence. These include mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA or cosmid DNA. Depending on the host-vector system utilized, any one of a number of suitable transcription and translation elements may be used. See generally Sambrook et al., supra and Ausubel et al. supra.

In general, a preferred DNA vector according to the invention comprises a nucleotide sequence linked by phosphodiester bonds comprising, in a 5' to 3' direction a first cloning site for introduction of a first nucleotide sequence encoding a protein transduction domain, operatively linked to a sequence encoding a cytotoxic domain. Preferably, the encoded cytctoxic domain includes additional cloning sites for an encoded potentially toxic molecule such as a zymogen. It is further preferred that the cytotoxic domain include additional cloning sites for encoded protease cleavage sites.

Figure 3A:
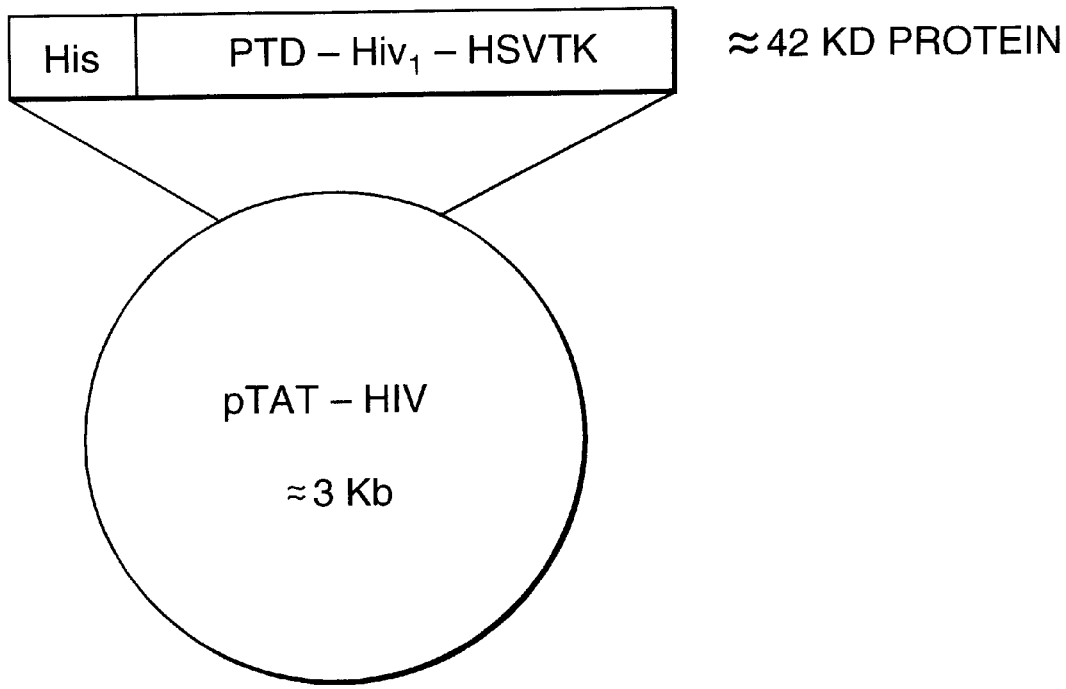
FIGS. 3A–D are drawings depicting illustrative DNA vectors according to the invention based on the pTAT/pTAT-HA plasmid. (3A) TAT-HSV TK fusion protein vector, (3B) TAT-Caspase-3 fusion protein vector, (3C) TAT-p16 fusion protein vector, and (3D) PTD-p16 fusion vector. Boxes designated HIS denotes optional addition of a 6XHIS tag; protein transduction domain (PTD); HIV protease-RT cleavage site ($HIV_1$), herpes simplex virus thymidine kinase (HSV TK); large caspase-3 domain (Lg); small caspase-3 domain (Sm); HIV p17-p24 protease cleavage site ($HIV_2$); p16 (mutant or wild-type p16 protein). Approximate molecular weights of the vectors are noted.
Figure 3B:
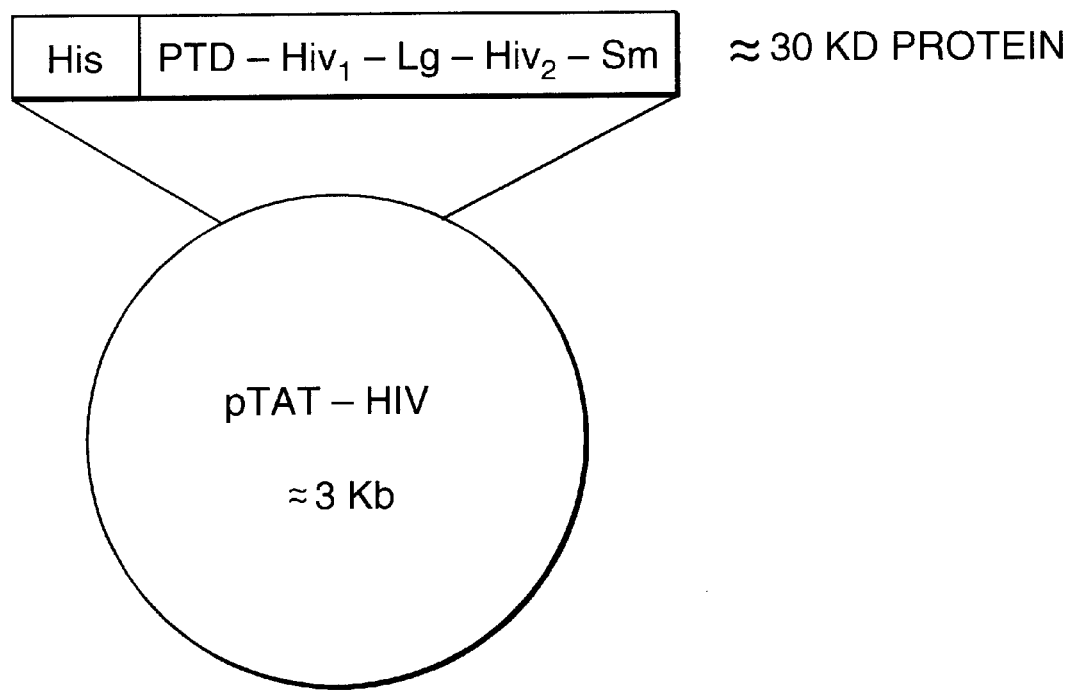
Figure 3C:
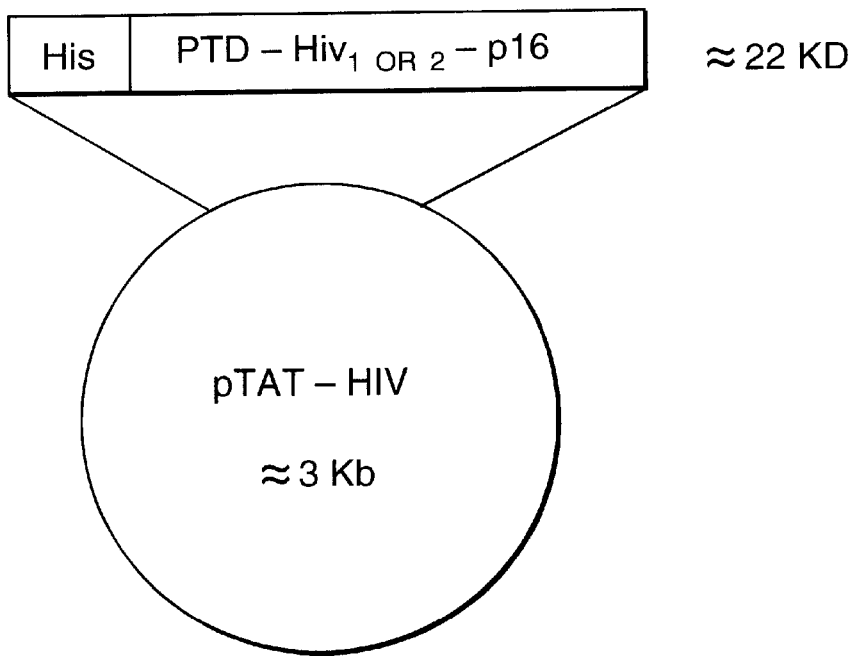

FIGS. 3A–C depict particularly preferred DNA vectors of the invention. The DNA vectors are derived from the pTAT/pTAT-HA vector illustrated in FIG. 1. Preferred nucleic acid linker sequences for use with the pTAT/pTAT-HA vector are shown in FIG. 2.

In most instances, it will be preferred that each of the fusion protein components encoded by the DNA vector be provided in a "cassette" format. By the term "cassette" is meant that each component can be readily substituted for another component by standard recombinant methods. In particular, a DNA vector configured in a cassette format is particularly desirable when the encoded fusion protein is to be used against pathogens that may have or have capacity to develop serotypes.

More specifically, it is envisioned that in some cases, certain pathogen serotypes may be associated with individual protease cleavage sites specific for that serotype. In this case, one or more existing protease cleavage sites in a DNA vector formatted as a cassette can be replaced with other pre-determined protease cleavage sites as needed. Particular protease cleavage sites can be selected in accord with presence of the pathogen in individual patients.

More generally, DNA vectors according to the invention formatted as a cassette minimize or eliminate occurrence of pathogen serotypes during treatment of a mammal and particularly a human by providing means to add or replace fusion protein components as needed.

In particular, with respect to pathogenic viruses such as HIV, the DNA vectors are specifically formatted to adapt to specific strains of the virus and future mutation of the virus by providing means to substitute new HIV proteolytic cleavage sites into the fusion protein. These sites can be readily determined in a patient by polymerase chain reaction (PCR) amplification of the DNA obtained from patient and DNA sequencing across the viral cleavage sites using standard oligonucleotide primers. For example, a variety of suitable oligonucleotide primers could be selected for the amplification in accord with published sequences. The new/altered cleavage site can then be inserted into a fusion protein, e.g., the pTAT-CPP32 bacterial expression vector described in the examples below, protein purified and misfolded and then administered to the patient in a relatively short time frame (about 3–4 weeks).

Significantly, the present anti-pathogen system can thus serve as an effective "warning system" that can register changes in pathogen serotype in vitro or in vivo. In particular, development of pathogen serotypes will be evidenced by decreased killing or injuring by the anti-pathogen system. The ability to rapidly detect appearance of the genetically altered pathogen serotypes is particularly relevant to developing rational therapies and can the remedied, e.g., by modifying the fusion protein as described above and/or by implementing a "cocktail" therapy approach as described below.

The term "cloning site" is intended to encompass at least one restriction endonuclease site. Typically, multiple different restriction endonuclease sites (e.g., a polylinker) are contained within the nucleic acid. It optimal positioning of cloning sites in a DNA vector facilitate the cassette format.

The fusion proteins of the present invention can be separated and purified by appropriate combination of known techniques. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electrical charge such as ion-exchange column chromatography, methods utilizing specific affinity such as affinity chromatograph, methods utilizing a difference in hydrophobicity such as reverse-phase high performance liquid chromatograph and methods utilizing a difference in isoelectric point, such as isoelectric focusing electrorhoresis, metal affinity columns such as Ni-NTA. See generally Sambrook et al. and Ausubel et al. supra for disclosure relating to these methods.

It is preferred that the fusion proteins of the present invention be substantially pure. That is, the fusion proteins have been isolated from cell substituents that naturally accompany it so that the fusion proteins are present preferably in at least 80% or 90% to 95% homogeneity (w/w). Fusion proteins having at least 98 to 99% homogeneity (w/w) are most preferred for many pharmaceutical, clinical and research applications. Once substantially purified the fusion protein should be substantially free of contaminants for therapeutic applications. Once purified partially or to substantial purity, the soluble fusion proteins can be used therapeutically, or in performing in vitro or in vivo assays as disclosed herein. Substantial purity can be determined by a variety of standard techniques such as chromatography and gel electrophoresis.

As discussed above, fusion proteins of the invention can be expressed in insoluble forms. That can avoid proteolytic degradation of the fusion protein, significantly increase protein yields and increase delivery of fusion protein into target cells. The insoluble protein can be purified by known procedures such as affinity chromatography or other methods as detailed above.

As mentioned generally above, a host cell can be used for preparative purposes to propagate nucleic acid encoding a desired fusion protein. Thus a host cell can include a prokaryotic or eukaryotic cell in which production of the fusion protein is specifically intended. Thus host cells specifically include yeast, fly, worm, plant, frog, mammalian cells and organs that are capable of propagating nucleic acid encoding the fusion. Non-limiting examples of mammalian cell lines which can be used include CHO dhfr- cells (Urlaub and Chasm, *Proc. Natl. Acad. Sci. USA*, 77:4216 (1980)), 293 cells (Graham et al., *J. Gen. Virol.*, 36:59 (1977)) or myeloma cells like SP2 or NSO (Galfre and Milstein, *Meth. Enzymol.*, 73(B):3 (1981)).

Host cells capable of propagating nucleic acid encoding a desired fusion protein encompass non-mammalian eukaryotic cells as well, including insect (e.g., *Sp. frugiperda*), yeast (e.g., *S. cerevisiae, S. pombe, P. pastoris., K. lactis, H. polymorpha*; as generally reviewed by Fleer, R., *Current Opinion in Biotechnology*, 3(5):486496 (1992)), fungal and plant cells. Also contemplated are certain prokaryotes such as *E. coli* amd Bacillus.

Nucleic acid encoding a desired fusion protein can be introduced into a host cell by standard techniques for transfecting cells. The term "transfecting" or "transfection" is intended to encompass all conventional techniques for introducing nucleic acid into host cells, including calcium phosphate co-precipitation, DEAE-dextran-mediated transfection, lipofection, electroporation, microinjection, viral transduction and/or integration. Suitable methods for transfecting host cells can be found in Sambrook et al. supra, and other laboratory textbooks.

The present invention further provides a production process for isolating a fusion protein of interest. In the process, a host cell (e.g., a yeast, fungus, insect, bacterial or animal cell), into which has been introduced a nucleic acid encoding the protein of the interest operatively linked to a regulatory sequence, is grown at production scale in a culture medium in the presence of the fusion protein to stimulate transcription of the nucleotilies sequence encoding the fusion protein of interest. Subsequently, the fusion protein of interest is isolated from harvested host cells or from the culture medium. Standard protein purification techniques can be used to isolate the protein of interest from the medium or from the harvested cells. In particular, the purification techniques can be used to express and purify a desired fusion protein on a large-scale (i.e. in at least milligram quantities) from a variety of implementations including roller bottles, spinner flasks, tissue culture plates, bioreactor, or a fermentor.

More particularly, misfolded fusion protein for use in accordance with the invention can be produced by a variety of methods. For example, in a preferred method, a desired fusion protein is expressed in suitable bacterial cells and then isolated from those cells as inclusion bodies. The fusion protein is subsequently denatured in a strong chaotropic agent such as about 6 to 8 M urea followed by chromatography on a first column to separate the fusion protein from other bacterial cell components which accompany it. The bound fusion protein is then eluted from the column by standard means followed by dialysis in a suitable buffer or additional chromatography on a second column to remove the urea. Such dialysis or chromatography will provide the fusion protein in a mixture of conformations, with only a minor portion in a lowest energy correctly refolded conformation, e.g. about 25 percent of the protein may be in the low energy folded state. As referred to herein, a fusion protein that is at least partially denatured means that at least a portion of the protein sample, e.g. at least about 10, 15, 20, 30, 40, 50, 60, 70 or 75 percent of the total number of amino acid residues in a substantially pure fusion protein sample, is in a conformation other than lowest energy refolded conformation.

A fusion protein misfolded into a mixture of conformations can then be transduced into desired cells. For example, the fusion protein can be directly added to cultured cells or to media in which those cells are being propagated.

While not wishing to be bound by theory, it is believed that the higher energy denatured forms of a fusion protein of the invention are able to adopt lower energy conformations that can be more easily transduced into a cell of interest. In contrast, the protein in its favored folded conformation will necessarily exist in a low energy state, and will be unable to adopt the relatively higher energy and hence unstable conformations that will be more easily introduced into a cell.

As mentioned previously, the invention thus provides methods of treatment against pathogen infections such as virus infections and diseases associated with viruses, which methods in general will comprise administration of a therapeutically effective amount of one or more of the fusion proteins discussed above to a mammal, particularly a human, suffering from or susceptible to the pathogen infection.

For example, the fusion proteins of the invention be useful to treat cells infected with a virus capable of causing an immunodeficiency disease, particularly in a human. The fusion proteins will be particularly useful to treat retroviral infection in cells and in a human, particularly HIV infected human cells. Specific examples of retroviral infections which may be treated in accordance with the invention include human retroviral infections such as HIV-1, HIV-2, and Human T-cell Lymphotropic Virus (HTLV) e.g. HTLV-I or HTLV-II infections.

The invention also provides methods of treatment of other diseases caused by or otherwise associated with a virus such as influenza including influenza A and B as well as diseases associated with viruses of the herpes family, e.g., herpes simplex viruses (HSV) including herpes simplex 1 and 2 viruses (HSV 1, HSV 2), varicella zoster virus (VZV; shingles), human herpes virus 6, cytomegalovirus (CMV), Epstein-Barr virus (EBV), and other herpes virus infections such as feline herpes virus infections, and diseases associated with hepatitis viruses including hepatitis C viruses (HCV). Examples of clinical conditions which are caused by such viruses include herpetic keratitis, herpetic encephalitis, cold sores and genital infections (caused by herpes simplex), chicken pox and shingles (caused by varicella zoster) and CMV-pneumonia and retinitis, particularly in immunocompromised patients including renal and bone marrow transplant patients and patients with Acquired Immune Deficiency Syndrome (AIDS). Epstein-Barr virus can cause infectious mononucleosis, and is also suggested as the causative agent of nasopharyngeal cancer, immunoblastic lymphoma and Burkitt's lymphoma.

It is contemplated that the pathogen may be present in a virulent, latent, or attenuated form. Also contemplated is a population of pathogens including a mixture of those forms. Examples of particular pathogens of interest are viruses, e.g., CMV, HSV-1, HCV, particularly HCV type-C, HIV-1, HIV-2, KSH, yellow fever virus, certain flaviviruses and rhinoviruses. In addition, the pathogen can be any one of those capable of causing malaria or a medical condition relating to same such as *P. falciparum, P. vivax, P. ovale*, or *P. malariae*. Typically, the plasmodia cause malaria or various medical complications relating to malaria. The invention can be used to treat an existing condition or it can be used prophylactically to prevent infection by one or more pathogens.

The anti-pathogen system and especially the fusion proteins of the invention can be administered to cells in vivo or in vitro by one or a combination of strategies.

For example, as mentioned above, the fusion proteins can be administered to primary or immortalized cells growing in culture in vitro by conventional cell culture techniques that generally include contacting the cells with the fusion protein and allowing the fusion protein to transduce through the cells for a specified period of time. Typically, cell media will be removed from the cells prior to the contact to increase fusion protein concentration.

In addition, the fusion proteins can be administered to cells in vivo, for example, by using a specified delivery mechanism suitable for introduction of fusion proteins into those cells. In general, the type of delivery mechanism selected will be guided by several considerations including the location of the cells, the degree of transduction needed to kill or injure cells infected by the pathogen, and the general health of the cells.

In particular, the fusion proteins of the invention may be administered to a normal, particularly a promoter such as a human, a variety of suitable routes including oral, topical (including transdermal, buccal or sublingual), nasal and parenteral (including intraperitoneal, subcutaneous, intravenous, intradermal or intramuscular injection. See generally *Reminington's Pharmaceutical Sciences*, Mack Pub. Co., Easton, Pa., 1980. Nasal or oral routes leading significant contact believe one or more of the fusion proteins and with airway epithelia, lung tissue being generally preferred.

The fusion proteins of the present invention can be administered as a sole active agent, in combination with one or more other fusion proteins as provided herein or in combination with other medicaments such as reverse transcriptase inhibitors such as a dideoxynucleoside including AZT, ddI, ddC, d4T, 3TO, FTC, DAPD, 1592U89 or CS92; TAT antagonists such as Ro 3-3335 and Ro 24-7429; and other agents such as 9-(2-hydroxyethoxymethyl) guanine (acyclovir), ganciclovir or penciclovir, interferon, e.g., alpha-interon or interleukin II, or in conjunction with other immune modulation agents including bone marrow or lymphocyte transplants or other medications such as levamisol or thymosin which would increase lymphocyte numbers and/or function as is appropriate.

Additional medicaments that can be co-administered with one or more fusion proteins of the invention include standard anti-malarial such as those disclosed in Goodman, G. et al. (1993), *The Pharmacological Basis of Therapeutics*, $8^{th}$ ed. McGraw-Hill Inc. pp. 978–198. Preferred anti-malarial drugs include chloroquine, chloroguanidine, pyrimethamine, mefloquine, primaquaine and quinine.

Administration of two or more of the above-referenced agents including the fusion proteins of the invention is illustrative of a "cocktail" or "cocktail" therapy.

While one or more fusion proteins of the invention may be administered alone, they also may be present as part of a pharmaceutical composition in mixture with conventional excipient, preferably a pharmaceutically acceptable organic or inorganic carrier substances that is generally suitable for oral or nasal delivery as mentioned previously. However, in some cases, other modes of administration may be indicated in which case the fusion protein can be combined with a vehicle suitable for parenteral, oral or other desired administration and which do not deleteriously react with the fusion proteins and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the fusion proteins.

For parenteral application, particularly suitable are solutions, preferably oily or aqueous solutions as well as, suspensions, emulsions, or implants, including suppositories. Ampules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle, is employed. Sustained release compositions can be formulated including those wherein the active component is protected with differentially degradable coatings, e.g., by microencapsulation, multiple coatings, etc.

Therapeutic fusion proteins of the invention also may be incorporated into liposomes. The incorporation can be carried out according to known liposome preparation procedures, e.g. sonication and extrusion.

It will be appreciated that the actual preferred amounts of active fusion proteins used in a given therapy will vary according to the specific fusion protein being utilized, the particular anti-pathogen system formulated, the mode of application, the particular site of administration, etc. Optimal administration rates for a given protocol of administration can be readily ascertained by those skilled in the art using conventional dosage determination tests conducted with regard to the foregoing guidelines.

In general, for treatment of a pathogen infection, e.g., a viral infections such as an HIV infection, a suitable effective dose of one or more fusion proteins will be in the range of from 0.01 to 100 milligrams per kilogram of bodyweight of recipient per day, preferably in the range of from 0.1 to 50 milligrams per kilogram bodyweight of recipient per day, more preferably in the range of 1 to 20 milligrams per kilogram bodyweight of recipient per day. The desired dose is suitably administered once daily, or several sub-doses, e.g. 2 to 5 sub-doses, are administered at appropriate intervals through the day, or other appropriate schedule.

As noted previously, a preferred mode of administration is in an aerosol format and particularly by nasal or oral routes.

Another aspect of the invention pertains to kits which include the components of the anti-pathogen system of the invention. Such a kit can be used to kill or injure cells infected by one or more pre-determined pathogens. In one embodiment, the kit includes a carrier means having in close confinement therein at least two container means: a first container means which contains one or more fusion proteins of the invention, and an optional second container means which contains a recombinant vector that encodes the fusion proteins.

To use the anti-pathogen system provided using components of the kit, the fusion protein is administered to cells, in vitro or in vivo in accordance with methods described above.

The invention is widely applicable to a variety of situations where it is desirable to kill or injure cells infected by one or a combination of pathogens. In addition to specified uses described above, the invention is also applicable to studying mechanisms of pathogen infection of eukaryotic cells such as those cells of plant, insect, or animal origin, e.g., as in cells from primates and other mammals such as domesticated animals including certain birds, dogs, cats, horses, sheep, cows and the like. Additionally, the present invention can be used for protection of crops or foodstuffs against pathogen attack.

In another aspect of the present invention, the anti-pathogen system can be used to screen candidate compounds for therapeutic capacity to inhibit certain proteins and particularly pathogen-specific proteases in infected cells. In particular, a preferred screening method includes transducing the anti-pathogen into desired cells, preferably cultured cells including immortalized or primary cells; infecting the cells with a pathogen, adding a candidate compound with potential therapeutic capacity to inhibit a pathogen-specific protease, and testing the cells for resistance to the pathogen, e.g., by performing a conventional cell viability assay.

The assay is usually compared to a baseline control to determine the effect of the compound of interest on the cell, e.g. the resulting phenotype. In addition, the candidate compound can be added before, during or after transducing the cells with the anti-pathogen system.

The baseline control may be the cell before introduction of the fusion protein, the cell in which the fusion protein has not been introduced, or the cell in which the fusion protein is non-functional, e.g. has a non-functional transcription activator region. One or more pre-determined pathogens can be added to the cell either before, after or during administration of the compound.

The candidate compound of interest can be one of several molecules, including cytokines, tumor suppressors, antibodies, receptors, muteins, fragments or portions of such proteins, and active RNA molecules, e.g., an antisense RNA molecule or ribozyme, or a drug. For example, a combinatorial library of derivatives of a known HIV RT inhibitors such as AZT can be readily tested by the present methods. Preferred compounds according to the invention are capable of reducing cell killing by at least about 40%, 50%, 60%, 70%, preferably at least about 80%, and more preferably at least about 90% or greater as assayed by standard cell viability tests such as by a Trypan blue exclusion test.

A preferred method of screening a candidate compound for therapeutic capacity to inhibit a pathogen-specific protease comprises:

a) transducing a fusion protein of the invention into a population of cells, infecting the cells with a pathogen capable of expressing or inducing pathogen-specific protease and expressing the protease, b) contacting the, fusion protein with the pathogen-specific protease sufficient to produce a cytotoxin; and c) correlating any cytotoxic effects to the therapeutic capacity of the candidate compound to modulate the pathogen-specific protease.

The protein transduction domain can be selected from TAT, Antennapedia homeodomain, HSV VP22; a suitable fragment thereof; or any non-naturally occurring sequences that are capable of transduction. The cytotoxic domain can include a caspase and one or more protease cleavage sites.

DNA and protein sequences described herein can be obtained from a variety of public sources including those specifically mentioned. A preferred source is the National Center for Biotechnology Information (NCBI)-Genetic Sequence Data Bank (Genbank) at the National Library of Medicine, 38A, 8N05, Rockville Pike, Bethesda, Md. 20894. Genbank is also available on the internet at http://www.ncbi.nlm.nih.gov. See generally Benson, D. A. et al., *Nucl. Acids. Res.*, 25:1 (1997) for a description of Genbank.

Other reagents used in the examples such as antibodies, cells and viruses can be obtained from recognized commercial or public sources such as *Linscott's Directory* (40 Glen Drive, Mill Valley Calif. 94941), and the American Type Culture Collection (ATCC) 12301 Parklawn Drive, Rockville, Md. 20852.

All documents mentioned herein are incorporated herein by reference.

The present invention is further illustrated by the following Examples. These Examples are provided to aid in the understanding of the invention and are not construed as a limitation thereof.

EXAMPLE 1

Production of a TAT Fusion Protein Expression Vector

A preferred plasmid for TAT fusion protein expression was prepared as follows. A map of that plasmid is depicted in FIG. 1 of the drawings. FIG. 2 shows a nucleotide sequence (SEQ ID NO: 12) and amino acid sequence (SEQ ID NO: 13) of the pTAT linker as well as a nucleotide sequence (SEQ ID NO: 14) and amino acid sequence (SEQ ID NO: 15) of the pTAT-HA linker.

pTAT and pTAT-HA (tag) bacterial expression vectors were generated by inserting an oligonucleotide corresponding to the 11 amino acid TAT domain flanked by glycine residues to allow for free-bound rotation of the TAT domain (G-RKKRRQRRR-G) (SEQ ID NO: 16) into the BamHi site of pREST-A (Invitrogen). A polylinker was added C' terminal to the TAT domain (see FIG. 1) by inserting a second oligonucleotide into the NcoI site (5' or N') and Eco RI site that contained NcoI-KpnI-AgeI-XhoI-SphI-EcoRI cloning sites. This is followed by the remaining original polylinker of the pREST-A plasmid that includes BstBI-Hind III sites.

The pTAT-HA plasmid was made by inserting an oligonucleotide encoding the HA tag (YPYDVPDYA; SEQ ID NO: 17; see FIG. 2) where sequence is bold) flanked by glycines into the, NcoI site of pTAT. The 5' or N' NcoI site was inactivated leaving only the 3' or C' to the HA tag followed by the above polylinker. The HA tag allows the detection of the fusion protein by immunoblot, immunoprecipitation or immunohistostaining by using 12CA5 anti-HA antibodies.

The nucleotide and amino acid sequences of each linker are set forth in FIG. 2. The pRSET-A backbone encodes ampicillin resistance, fl, ori, ColE1 ori (plasmid replication) and the transcript is driven by a T7 RNA polymerase promoter.

EXAMPLE 2

Preparation of Misfolded TAT Fusion Proteins

The TAT fusion proteins described below were purified from host cells and purposefully misfolded to enhance transduction. More specifically, the fusion proteins were purified by sonication of transfected BL21(DE3) pLysS cells (Novagen) obtained from a 5 hr 1 L culture. That culture was inoculated with 100 ml from an overnight culture in 10 ml of buffer A (8M urea/20 mM HEPES (pH 7.2 (100 mM NaCl)). Cell lysates were resolved by centrifugation, loaded onto an Ni-NTA column (Qiagen) in buffer A plus 20 mM imidazole. The column was then washed in 10× column volume, eluted by increasing imidazole concentration in buffer A (stepwise) and then applied to a Mono-Q column on an FPLC (Pharmacia) in 4 M urea/20 mM HEPES (pH 7.2, (50 mM NaCl)). TAT fusion protein were eluted with a 1 M NaCl step, desalted on a PD-10 desalting column (Pharmacia) into PBS or 20 mM HEPES [pH 7.2]/137 mM NaCl and frozen in 10% glycerol at −80° C.

FITC-labeled TAT fusion proteins were generated by fluorescein labeling (Pierce), followed by gel purification in PBS on an S-12 column attached to an FPLC (Pharmacia) and added directly to culture media.

EXAMPLE 3

Production of TAT p16 Fusion Proteins

TAT p16 fusion proteins including HIV protease cleavage sites (P17-p24 or p7-p1) were made according to the following method.

A. Preparation of pTAT-(HIV cleavage sites) constructs:

This plasmid was made by inserting double stranded oligomers encoding the p17-p14 and p7-p1 HIV cleavage sites into the NcoI site of pTAT and pTAT-HA. The cleavage consist 14 amino acids, 7 on each side of the HIV cleavage site.

p17-p24 site (57 mer), positive strand: 5' CAT GTC AGG CTC CCA GGT GTC ACA GAA CTA TCC AAT CGT GCA GAA CCT GCA GGG CGC 3' (SEQ ID NO. 18)

p7-p1 HIV cleavage site (60 mer), positive strand: 5' CAT GCA TTC AGG CTG CAC CGA ACG CCA GGC TAA CTT CCT GGG CAA AAT CTG GCC AGG CGC 3' (SEQ ID NO. 19)

An oligonucleotide corresponding to the HIV cleavage site p17-p24 (SEQ ID No.18) or p7-p1 (SEQ ID NO. 19) was fused to the pTAT vector described in Example 1 (3' to the PTD silues) to produce a pTAT-HIV$_1$ or pTAT-HIV$_2$ vector, respectively. The pTAT-HIV$_{1,2}$ vectors served as a parental vectors for the constructs shown for example in FIGS. 3A–C. A p16 protein cDNA sequence was fused to the p17-p24 HIV cleavage site to produce an in-frame TAT-p16 fusion protein cDNA (FIG. 3C). A second p16 fusion protein was made by fusing the p16 cDNA to the pTAT-HIV$_2$ vector. The order of components in each vector construct (N' terminus to C'-terminus) was: HIS-TAT-PTD-CLEAVAGE SITE-p16-PROTEIN, whereby "cleavage site" denotes the p17-p24 or p7-p1 cleavage sites, respectively. The fusion proteins were each purified and misfolded according to the method described in Example 2 above. The TAT-p16 cDNA vectors were propagated in DH5-α bacteria.

Figure 3D:
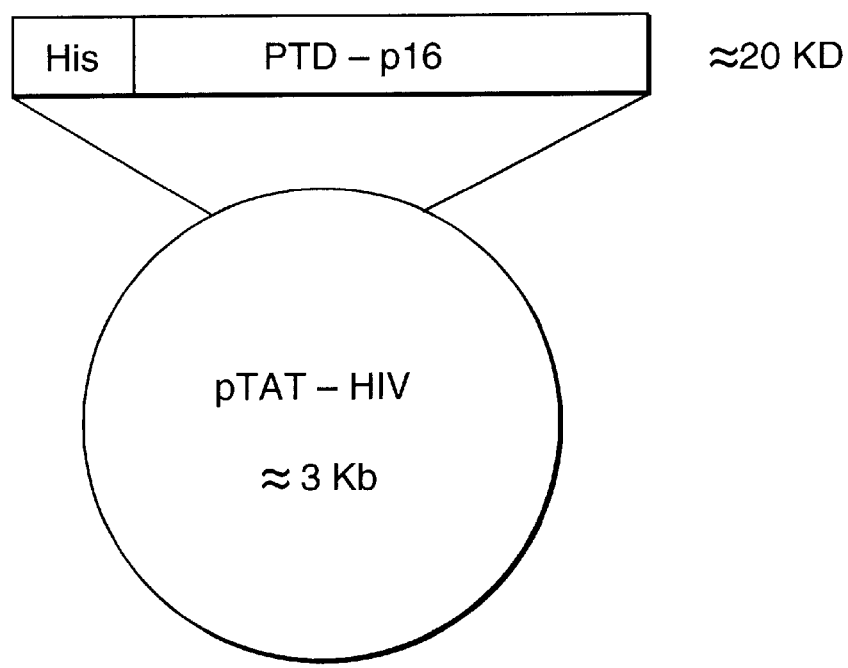

Purified p16 fusion proteins were individually transduced into Jurkat T-cells infected by HIV. Methods for infecting the Jurkat T-cells with HIV and transducing fusion proteins are described in examples, which follow. After 4, 8 and 12 hours, the cells are analyzed for cleavage of the fusion protein by Western/immunoblot analysis using a commercially available anti-P16 antibody (Santa Cruz). As a control, the p16 cDNA was fused to the pTAT vector described in Example 1 to produce the vector shown in FIG. 3D (no HIV protease cleavage site). That vector encoded a p16 fusion protein fused to TAT that was not cleaved in the infected cells. However, efficient cleavage was observed with p16 fusion proteins encoded by vectors shown in FIG. 3C Tht contained the HIV cleavage sites.

EXAMPLE 4

Detection Of the p16 Fusion Protein Inside Transduced Cells

To see if p16 fusion proteins could remain in the cell cytosol of the HIV infected cells, the TAT-HIV$_{1,2}$ p16 fusion proteins produced in Example 3 were purified and labeled with FITC as described above. About 35 to 45 nanomoler of the labeled fusion protein was then added to HIV-infected (NLHX strain) and uninfected Jurkat T-cells in accordance with Example 6 below. The transduced Jurkat T-cells were then analyzed by FACS. All (100%) of cells in a mixed population of HIV infected/uninfected cells were transduced with the p16 protein at 1, 2, 4, 8 and 16 hours post-addition of the FITC conjugated fusion protein. However, when the cells were washed in fresh media and the PTD has driven out of the cells due to the concentration gradient (now high inside and 0 outside), the infected cells retained the cleaved substrate (the p16 portion) but uninfected controls lost all of the transduced protein (it transduced out) is determined by the continued presence of FITC-labeled p16 as analyzed by FACS.

EXAMPLE 5

Production of TAT-CPP32 Fusion Protein

A human CPP32 cDNA (Alnemri et al., *J. Biol. Chem.*, 269:30761(1994); Genbank Accession No. U13737) was generated by independently PCRing (i.e. performing a Polymerase Chain Amplification (PCR) step) the CPP32 p17 and p12 domains, then adding these DNA fragments together and PCRing using the outside PCR primers. The protocol is outlined in FIG. 5. This is called a double PCR cloning approach and is a common methodological approach to link to two independent DNA fragments together, as follows:

The p17 domain of CPP32 cDNA was PCRed using the A (+strand) and B(−strand) primers (see below) and the p12 domain by using B(+strand) and C(−strand) primers. The A primer encodes the p17-p1 HIV cleavage site in-frame with the CPP32 p17 domain coding sequence and the B primer encodes the p17-p24 HIV cleavage site. After this first PCR, the two purified fragments were mixed together and PCRed using only the A(+strand) and C(−strand) primers. The two DNA fragments base pair together because the 3' end of p17 PCRed domain contains the (−) strand of the 5' end of the p12 PCRed domain. After this PCR, the resultant DNA fragment was digested with XhoI at the 5' end and EcoRI at the 3' end yielding an approximately 900 bp fragment. This fragment was cloned into the XhoI and EcoRI Sites of pTAT and pTAT-HA plasmids. The protein, TAT-CPP32 wild type, was produced in BL2I(DE3) cells as outlined above.

A(+strand) primer, (90 mer): 5' CGC CTC GAG GGC GGC TGC ACC GAA CGC CAG GCT AAC TTC CTG GGC AAA ATC TGG CCA GGC GGA ATA TCC CTG GAC AAC AGT TAT AAA ATG 3' (SEQ ID NO. 20)

B (+strand) primer, (72 mer): 5' GGC GGC TCC CAG GTG TCA CAG AAC TAT CCA ATC GTG CAG AAC CTG CAG GGC GGT GTT GAT GAT GAC ATG GCG 3' (SEQ ID NO. 21)

B (−strand) primer, (75 mer): 5' ACC GCC CTG CAG GTT CTG CAC GAT TGG ATA GTT CTG TGA CAC CTG GGA GCC GCC TGT CTC AAT GCC ACA GTC CAG 3' (SEQ ID NO. 22)

C (−strand) primer, (37 mer): 5' CGA GCT ACG CGA ATT CTT AGT GAT AAA AAT AGA GTT C 3' (SEQ ID NO. 23)

The order of components in the resulting construct (N' terminus to C'-terminus) was: HIS-TAT-PTD-HIV$_2$— subunit of CPP32-HIV$_1$—small subunit of CPP32. The vectors encoding the HIS-TAT-PTD-HIV$_2$—large subunit of CPP32-HIV—small subunit of CPP32 cDNA fusion proteins were each propagated in DH5-α bacteria. The fusion proteins were expressed and purified as described in Example 2 above. The HIS-TAT-PTD-HIV$_2$—large subunit of CPP32-HIV$_1$ small subunit of CPP32 fusion protein is referred to as "TAT-CPP32".

EXAMPLE 6

Specific Cell Killing with the TAT-CPP32 Fusion Protein

To show that the TAT-CPP32 fusion protein produced in Example 5 was capable of killing HIV-infected cells, the fusion protein was purified and detectably-labeled with FITC as described above in Example 2. The labeled TAT-CPP32 fusion protein was tested by the following method.

About 5×10$^6$ Jurkat T-cells were infected by HIV (strain NLHX; about 1×10$^5$ to 1×10$^6$ infectious virus per ml). The cells were propagated in RPMI media. Approximately 4 to 7 days after the infection, the media was removed from the plates and about 35 to 45 nanomoler of the TAT-CPP32 fusion protein was added to the cells. The cells were incubated with the fusion proteins for about 30 minutes to allow transduction into the cells. Using FACS analysis, it was found that about 100% of the cells were transduced by the fusion protein. Subsequently, media was added back to the plates and after about 18 hours post-transduction, the cells were examined for cell killing using conventional trypan blue exclusion and microscopy.

It was found that about all of the infected cells were killed by TAT-CPP32. This result is important because it indicates that the TAT-CPP32 fusion protein specifically kills HIV-infected cells but does not kill the uninfected cells in the population.

EXAMPLE 7

Inhibition of TAT CPP32 Killing Activity

1. Administration of an HIV protease inhibitor

To show that the TAT-CPP32 fusion protein killed HIV-infected Jurkat T-cells by an mechanism that requires specific induction of an HIV-protease, the protease inhibitor Ritonavir (Abbott) was added to infected cells after transduction of the fusion protein. Briefly, cells were infected and transduced as described in Example 6 above. Following the transduction, about 1 µg/ml Ritonavir was added to the cell media and allowed to incubate with the cells for about 18 hours. The cells were then assayed for cell killing by conventional trypan blue exclusion and microscopy.

It was found that administration of the Ritonavir essentially blocked the ability of the TAT-CPP32 to kill infected cells. Thus, the TAT-CPP32 fusion protein killing of HIV-infected cells requires an active HIV protease.

2. Mutation of the CPP32 fusion protein (TAT-CPP32 mutant C163M)

To demonstrate that TAT-CPP32 cell killing was due to activation of the CPP32 protein following HIV-specific cleavage, CPP32 was inactivated by mutating the catalytic cysteine at residue 163 to methionine. Briefly, the TAT-CPP32 molecule made in Example 5 was mutagenized to change the catalytically active Cys residue (#163) in the active site to Met by site directed mutagenesis. The following double stranded oligomeric nucleotide was inserted into the StuI site (in the p17 domain at the 5' end of the insert) and PstI site present in the p17-p24 HIV cleavage site between the p17 and p12 domains in TAT-CPP32. The double stranded oligomer has a blunt end at the StuI 5' end and a 3' overhang at the PstI 3' end.

positive strand oligo (85 mer): 5' CCA TGC GTG GTA CCG AAC TGG ACT GTG GCA TTG AGA CAG GCG GCT CCC AGG TGT CAC AGA ACT ATC CAA TCG TGC AGA ACC TGC A 3' (SEQ ID NO. 24) (bold indicates Cys to Met codon change).

The fusion protein was referred to as "TAT-CPP32$^{mut}$" or "TAT-CPP32 mutant" to denote the mutated catalytic Cys residue at position 163 of the CPP32 fusion protein.

The TAT-CPP32$^{mut}$ fusion protein was purified and transduced into HIV-infected Jurkat T-cells as described above in Example 6. It was found that the fusion protein was not capable of killing the HIV-infected cells. In contrast, the results of Example 6 show that the TAT-CPP32 fusion protein (with wild-type catalytic Cys residue) specifically killed the HIV infected Jurkat cells.

It is recognized that activation of caspases and particularly CPP32 triggers apoposis and is known in the field as "the point-of-no-return". The results are consistent with this recognition. The results show that the TAT-CPP32 fusion protein specifically kills HIV infected cells perhaps by undergoing apoptosis. In particular, the released CPP32 molecule is believed to start apoptosis only in the infected cells by activating endogenous caspases by cleaving and by cleavage of specific substrates such as PARP.

It is recognized in the field that HIV replication generally requires the presence and specific activity of HIV protease to cleave and process viral polyproteins, such as gag and gag-pol, for maturation as part of its infective life cycle. Transduction of anti-HIV killing molecules into HIV infected cells undergoing HIV replication, but not uninfected cells, will result in the specific recognition of the engineered HIV cleavage sites in any anti-HIV killing molecule of the invention, converting it from the inactive protein into an active killing molecule. However, uninfected cells do not contain the HIV specific protease and therefore, although present in uninfected cells it will remain in its inactive form.

Without wishing to be bound to any specific theory, it is believed that a cell transduced by the anti-HIV fusion protein such as TAT-CPP32 molecule will undergo apoptosis thereby reducing the viral burst of newly packaged virus particles. In addition, as several proteins are packaged inside the virion, including protease and RT, any escaping packaged virus particles may contain an active anti-HIV killing molecule that could 1) kill the particle prior to infection of a new cell or 2) initiate apoptosis in the newly infected cell, if so it should occur prior to replication of any virus particles.

EXAMPLE 8

Production And Specific Cell Killing With a TAT-TK Fusion Protein

Figure 4:
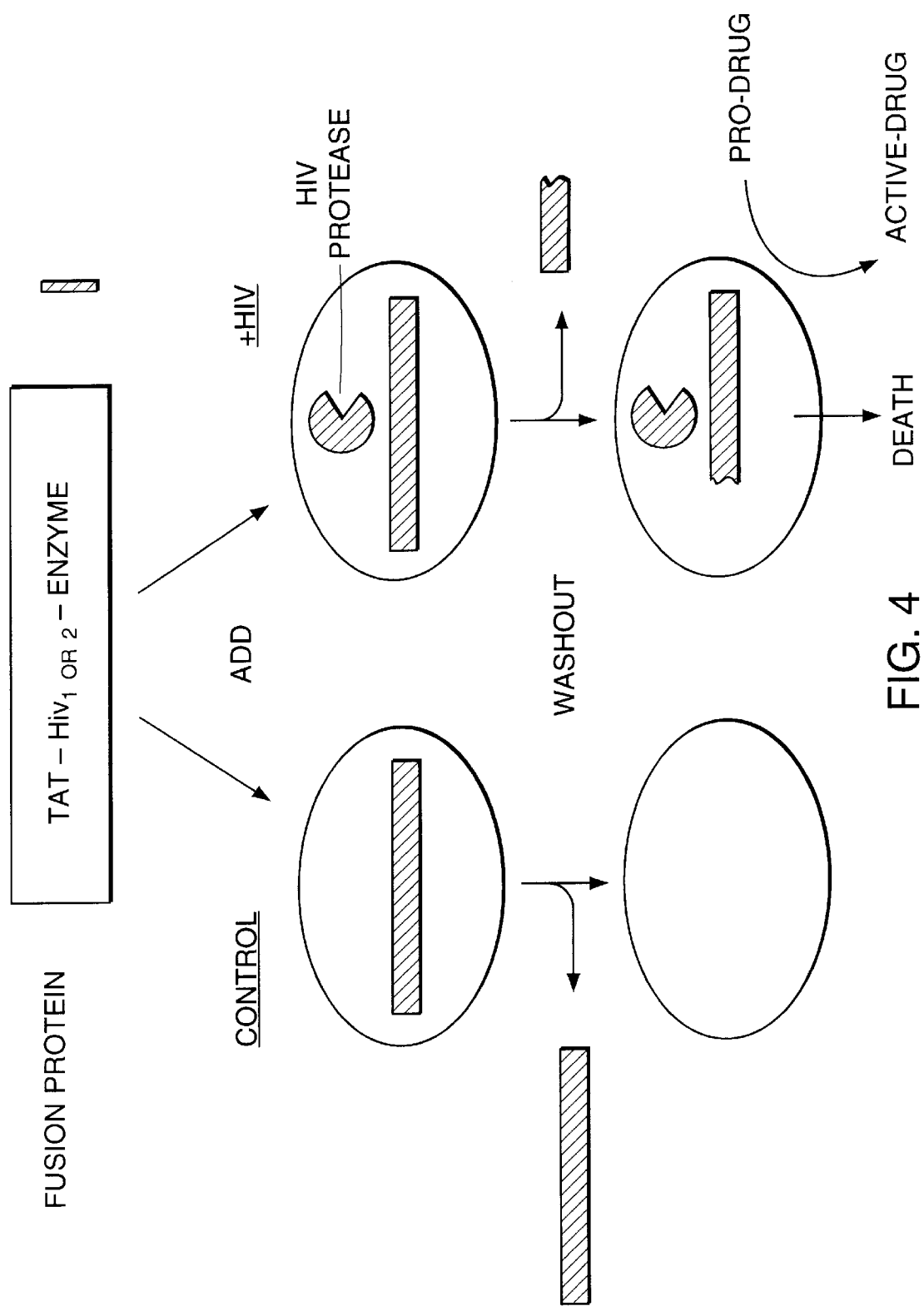
FIG. 4 is a schematic drawing outlining cell killing with a fusion protein comprising an enzyme capable of converting a prodrug into an active drug. $HIV_{1,2}$ is defined in FIGS. 3A–D above.

FIG. 4 outlines a method for killing HIV-infected Jurkat T-cells by transducing a fusion protein comprising TK into the cells and then contacting the transduced cells with a prodrug (Acyclovir (Glaxo Wellcome)). TK released from the fusion protein converts the Acyclovir into an active killing molecule, thereby killing the infected cells. However, uninfected (control) cells are not harmed by transduction of the TK fusion protein and administration of the Acyclovir.

The TAT-TK fusion protein was made by the following method. The HSV-1 TK sequence was obtained from Genbank (Accession No. J02224). PCR primers were generated that corresponded to the N' and C' of TK. After PCR, the DNA fragment was cut with NcoI and EcoRI and inserted into the NcoI and EcoRI sites of pTAT-(HIV p17-p24 cleavage site) or pTAT-(HIV p7-p1 cleavage site).

TK forward PCR primer (34 MER): 5' CGG GCC GGC CCC ATC GCT TCG TAC CCC TGC CAT C 3' (SEQ ID No. 25)

TK reverse PCR primer (39 MER): 5' GGC GGG CCG GGA ATT CTC AGT TAG CCT CCC CCA TCT CCC 3' (SEQ ID NO. 26)

The fusion proteins was each purified and misfolded as discussed above in Example 2.

About $5 \times 10^6$ Jurkat T-cells were infected by HIV (strain NLHX) as described above in Example 6. Approximately 4 to 7 days after the infection, the media was removed from the plates and about 35 to 45 nanomoler of the TAT-TK fusion protein (p17-p24 or p7-p1 cleavage site) was added to the cells. The cells were incubated with the fusion proteins for about 30 minutes to allow transduction into the cells. Using FACS analysis, it was found that about 100% of the cells were transduced by the fusion protein.

Transduced cells were allowed to incubate for about 18 hours to allow build-up of TK cleaved from the TAT-TK fusion protein. After this time period, the cells were washed in media and allowed to incubate for a further 4 hours. At this point about 1 to 100 nanomoler Acyclovir was added to the plates. After about 3 days, infected and non-infected cells were examined for cell killing by conventional trypan blue exclusion and microscopy. It was found that approximately 100% of the total number of infected cells were killed by administration of the TAT-TK fusion protein and acyclovir.

The results show that the TK enzyme was specifically concentrated in infected cells. However, in uninfected cells, the TK enzyme was not concentrated; the TAT-TK fusion was found to be transduced back out of those cells after washing. Thus, it is believed that the HSV TK processed the prodrug into an active killing drug only in the cells where it is retained, the infected cells, and not in the normal cells due to the inability of human/mammalian TK to process the prodrug. The results thus demonstrate that the TAT-TK fusion protein is an effective anti-HIV killing molecule.

In addition to TK, an HSV cytosine deaminase cDNA can be readily substituted for the TK gene to provide specific killing or injuring of HSV infected cells in combination with certain nucleoside analogs known in the field.

The TAT-TK and TAT-CPP32 fusion proteins specifically described can be administered to an HIV-infected patient either as an injectable or preferably via an inhalation device to deliver same to the lungs where it will transduce into the blood stream. The fusion proteins will transduce into all contacted cells (airway and lung tissue, blood cells, etc.) including those typically infected by HIV such as certain immune cells in the bloodstream.

Based on experimental and theoretical modeling, it has been reported that average half-life of an HIV infected T cell in vivo is approximately 1.6 days. Therefore a preferred treatment protocol for an HIV-infected will be by injection and more preferably inhalation several 7 day periods. Effectiveness of the methods can be monitored by performing well-known manipulations (e.g., PCR) to detect HIV viral particles in biological fluids such as blood. This process is sometimes known as estimating patient viral loads. The manipulations can help determine proper dosing of the fusion protein either alone or in combination with anti-HIV drugs such as those previously mentioned.

EXAMPLE 9

Transduction of Uninfected Jurkat T-Cells With TAT-HIV Protease

It is recognized that HIV infections can be difficult to monitor in vitro and can often vary with respect to the percentage of cells infected. Additionally, not all cells that can be infected by pathogens are infected by HIV virus. To help overcome these problems and to help further understand induced killing by the TAT-CPP32 fusion protein, co-transduction experiments were performed with an HIV protease fused to TAT. The goal was to co-transduce uninfected Jurkat T-cells with two fusion proteins, the first fusion protein including the cell killing molecule (TAT-CPP32) and the second fusion protein including the HIV protease (TAT-protease) for cleaving the first fusion protein.

Briefly, a transducible HIV protease was constructed by PCR cloning protease from HIV NLHX strain into the pTAT-(p7-p1 cleavage site) vector. PCR primers were synthesized corresponding to initiating ATG (methionine) of the protease and the translational termination site. The DNA fragment was inserted into pTAT-(p7-pI cleavage site) vector at the NcoI 5'/N' terminal end and the EcoRI site 3'/C' terminal end. The protein was expressed from the plasmid, pTAT-(p7-p1)-Protease, in BL2I (DE3) cells and purified as described above. The fusion protein is referred to as "TAT-Protease."

Figure 6A:
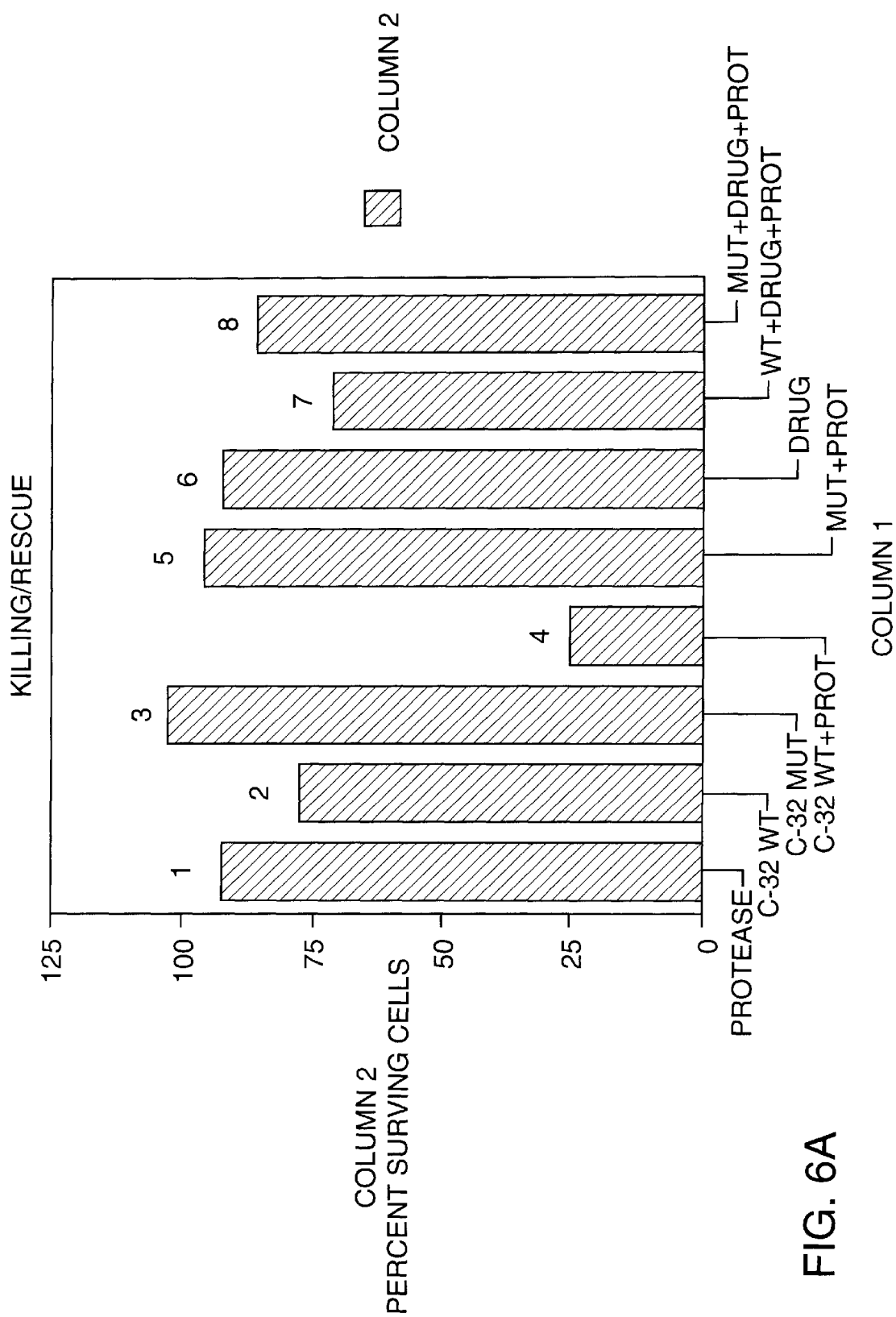
FIG. 6A is a bar graph showing percentage of viable cells after transduction of various TAT fusion proteins and treatment with anti-HIV drug.

To test for activation of the TAT-CPP32 by TAT-Protease, $2 \times 10^6$ Jurkat T cells were placed in 2 ml of culture (RPMI media). To these cells, various combinations of control and experimental transducible proteins were added in 50–100 nM ranges, as follows:

1. control
2. TAT-Protease (50–100 nM)
3. TAT-CPP32 wild type (50–100 nM)
4. TAT-CPP32 mutant (50–100 nM)
5. TAT-CPP32 wild type plus TAT-Protease
6. TAT-CPP32 mutant plus TAT-Protease
7. Ritonavir (HIV protease inhibitor)
8. TAT-CPP32 wild type plus ritnovir
9. TAT-CPP32 mutant plus ritnovir The cells were assayed for survival at 18 hr post-addition by trypan-blue exclusionary dye microscopy. TAT-Protease, TAT-CPP32 wild type and mutant proteins showed minimal cytotoxicity when added alone. See FIGS. 6A and 6B. However, the addition of TAT-CPP32 wild type, but not mutant, plus TAT-protease resulted in a substantial loses of viable cells and hence, activation of the TAT-CPP32 wild type protein. The addition of the protease inhibitor to this experiment resulted in the loss of specific TAT-CPP32 wild type killing. Thus, activation of TAT-CPP32 requires the presence of HIV protease. Taken together, these observations demonstrate the specificity of activation of the TAT-CPP32 protein only in cells expressing HIV protease.

It is believed that the co-transduction method is generally applicable for killing or injuring cells that are not usually infected by HIV virus. Examples of such cells include certain CD4$^-$ (minus) immune cells and non-immune cells such as fibroblasts. Additionally, it will be appreciated that the method is readily adapted to include other transducing fusion proteins described herein, e.g., specified TAT fusion proteins requiring administration of a prodrug (e.g., TAT-TK and Acylcovir).

EXAMPLE 10

Synthetic Transduction Domains With Enhanced Transduction Efficiency

The following artificial (i.e. synthetic) peptides were made by conventional peptide synthesis as described above. A goal of this experiment was to produce transduction domains that could transduce more effectively as judged by the intracellular concentration in transduced cells. The transduction domains were tested against a suitable control, which typically was the "natural" TAT or an Antp transduction domain. Briefly, a FITC group was synthetically attached to N-terminus of 100% of each peptide so that transduction rate and intracellular concentration of each peptide could be quantified at equilibrium. The TAT transduction domain is recognized to be alpha-helical. In each synthetic peptide sequence, an alpha-helix was modeled with varying amounts of Arg on one face. That is, a series of synthetic peptides was designed that contained varying amounts of Arg residues on one surface and substituted with Ala residues. Both Ala and Arg residues have the highest probability/energetics for maintaining an alpha-helical structure. See FIG. 7, which depicts each peptide as a helical wheel projection. The peptides are shown below in Table 2.

TABLE 2

| SEQ. ID NO. | Modified Peptide | Rate Compared to TAT | Intracellular Concentration |
|---|---|---|---|
| 2 | YGRKKRRQRRR[a] | = | 1 X |
| 52 | AGRKKRRQRRR | = | 1 X |
| 3. | YARKARRQARR | = | 10 X |
| 4. | YARAAARQARA | = | 5 X |
| 5. | YARAARRAARR | = | 10 X |
| 6. | YARAARRAARA | = | 5 X |
| 7. | YARRRRRRRRR | = | 5 X |
| 8. | YAAARRRRRRR | = | 5 X |
| 53 | YAAAAAAAAAA[b] | N.D. | N.D. |
| 54 | RQIKIWFQNRRMKWKK[c] | < | 1 X |

[a]Original TAT domain
[b]Insoluble
[c]Original ANTP sequence

The synthetic peptides were transduced into Jurkat T-cells along lines described above in Example 4. As can be seen in Table 2, all of the synthetic peptides transduced into the cells. The data show that the synthetic peptides with the most favorable rate and intracellular peptide concentration had the highest probability of having alpha helical structure (compared to naturally-occurring TAT) due to the substituted Ala residues. Further, the best synthetic peptides had Arg residues aligned on a single surface of the helix as suggested by helical wheel diagrams. See FIG. 7. In particular, the modified synthetic peptides represented by SEQ ID Nos. 3 to 8 exhibited about a 5 to 10 fold increase in intracellular concentrations when compared to naturally-occurring TAT (SEQ ID NO 1).

The data indicate that it is possible to design synthetic peptides with enhanced transduction efficiency compared with TAT. For example, the data show that it is possible to increase transduction efficiency of naturally-occurring TAT by increasing probability of alpha helical helix formation in the peptide and by aligning at least two Arg residues on a single peptide helical face. The synthetic peptide sequences shown in Table 2 can be used to increase the transduction efficiency of a variety of fused amino acids, e.g., addition of 2, 5, 10, 20, 50 and 100 amino acids to the synthetic peptide sequence. The synthetic peptide sequences can also be fused to protein sequences of about 10, 15, 20, 30, 50, or about 100, up to about 500 kD or greater. The resulting fusion proteins can be tested for an increase in transduction efficiency as described above.

The naturally-occurring Antp peptide (SEQ ID No. 10) typically exhibits a slower transduction rate than the TAT peptide. Thus, naturally-occurring TAT and the synthetic peptides described above will often be preferred for transducing amino acid sequences and particularly large proteins into cells.

Figure 7:
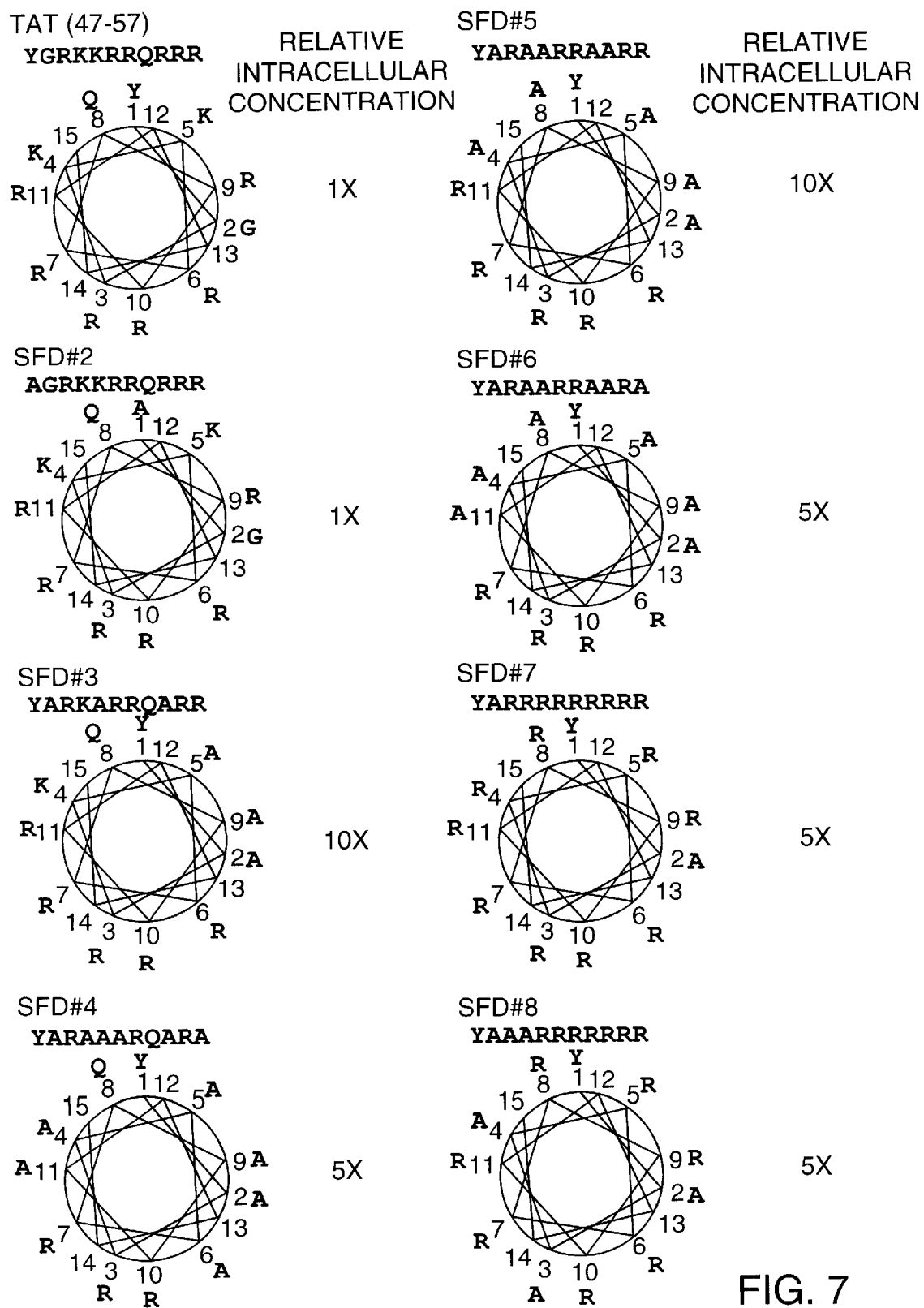
FIG. 7 is a drawing showing helical wheel projections of preferred transduction proteins of this invention (SEQ ID NOS: 2, 52, 3–8). "TAT (47-57)" refers to amino acids 47 to 57 of the TAT peptide (SEQ ID. NO. 2). "SFD" refers to specified transduction domain sequences. The term "relative intracellular concentration" in FIG. 7 refers to the intracellular amount of transduced peptide sequence relative to the TAT peptide.

Table 2 shows synthetic peptide sequences that result in the rapid transport by transduction across cellular membranes enhanced into cells. The data show that those peptides having 1) a strong; alpha helical nature and 2) at least a face/surface that is covered by Arg. residues are the best transducing domains. FIG. 7 below shows a helical wheel plot showing the placement of the residues. All of the synthetic peptides have a transduction rate close to that of TAT (47-57), but some result in an increase intracellular concentration. Particular peptide sequences have at least the face of the helix containing basic residue such as Arg.

EXAMPLE 11

Killing HIV/Pathogen Infected Cells by Transduction of a Modified TAT-Bid Protein The pro-apoptotic protein Bid a 20 kDa protein related to the the Bc12/Bax family of apoptotic regulatory proteins. Bid is present in a zymogen proform in the cytoplasm. Activation of cells to undergo apoptosis by signaling through receptors such as Fas results in activation of two separate pro-apoptotic cascades/pathways. Additionally, Caspase-8 activation results in direct cleavage of cytosolic p20 Bid at Asp59 residue (aspartic acid residue #59 in mouse and Asp60 in human). This results in loss of the 5 kDa "pro" domain of Bid and rapid translocation of p15 Bid to the mitochnodria resulting in release of cytochrome c and mitochondrial poisoning and subsequent death. Thus, Bid exists as an inactive proform/zymogen that can be specifically activated by by proteolytic cleavage resulting in apoptotic induction through a different pathway than Caspase-3 (CPP32) via the DNA degradation pathaway.

A transducible TAT-Bid protein can be made by adding TAT to the N' terminus and removing the endogenous Caspase cleavage site of Bid and replacing it with an HIV cleavage site (TAT-p5 Bid-HIV cleavage-p15 Bid). The goal was to test the effectiveness of the fusion protein in killing HIV infected cells or cells expressing HIV Protease.

A TAT-HIV clevage-p15 Bid protein can also be made to provide a comparison between the two transducible Bid proteins. The cloning strategy is outlined below and, as with the TAT-CPP32 protein, any pathogen protease cleavage site could be cloned into this killing protein. The HIV cleavage site is used in this example as a model system. In addition, killing by TAT-Bid may be more effective than TAT-CPP32 in some cell types/diseases or, more than likely, be complimentary to TAT-CPP32 such that co-transduction of both killing proteins may result in a synergistic effect to further kill the infected cells and potentially at lower concentration levels.

1. Cloning Strategy

Murine Bid was PCR amplified by utilization of the following DNA primers in which the end product results in NcoI (DNA cleavage site)—pS Bid domain—HIV proteolytic clevage site (on the encoded protein)—p 15 Bid domain by performing a double PCR. A TAT-HIV cleavage—p1S Bid is also described and under construction.

First, the p5 domain is PCR amplified with primer IF and 2R and in a separate PCR reaction p IS domain is PCRed with primer 2F and 4R. These DNA fragments are purified, mixed together and hybridize via the common regions present in 2F and 2R which are present on the 3' and 5' ends of the respective DNA fragments. The ends of this DNA fragment are extended and a final PCR reaction is performed using only primers 1F and 4R which selects for the full length DNA fragment. This is a common cloning technique. The full length fragment is then cloned/ligated into pTAT-HA by cleavage with NcoI at the 5' end and EcoRI at the 3' end. The resultant plasmid, pTAT-Bid, was transformed into DH5α *E. coli* strain and then into B121(DE3)pLysS *E. coli* strain and protein purified as outlined for the TAT-CPP32 protein. The resultant protein will contact an HIV Protease cleavage site between the TAT-p5 and p15 domains and is designated TAT-p5-HIV-p15 Bid.

TAT-HV-p15 Bid can be constructed similar to the above except only a single PCR reaction is required. The primer 3F contains an NcoI DNA cleavage site followed by the HIV proteolytic cleavage site and DNA sequence homology to the 5' end of p15 Bid domain. The DNA fragment generated from the PCR reaction with with primer 3F and primer 4R is digested with NcoI and EcoRI and cloned into the NcoI and EcoRi sites of pTAT-HA, as outlined above.

2. Primers:

Primer IF (87 mer): CgC gCC ATg ggC ggC TCC CAg gTg TCA CAg AAC TAT CCA ATC gTg CAg AAC CTg CAg ggC ggC gAC TCT gAg gTC AgC AAC ggT TCC (SEQ. ID NO. 27)

Primer 2F (52 mer): TTC CTg ggC AAA ATC Tgg CCA ggC ggC AgC CAg gCC AgC CgC TCC TTC AAC C (SEQ. ID NO. 28)

Primer 2R (46 mer): gTT AgC CTg gCg TTC ggT gCA gCC TgT CTg CAg CTC gTC TTC gAg g (SEQ. ID NO. 29)

Primer 3F (88 mer): CgC gCC ATg ggC ggC TgC ACC gAA CgC CAg gCT AAC TTC CTg ggC AAA ATC Tgg CCA ggC ggC AgC CAg gCC AgC CgC TCC TTC AAC C (SEQ. ID NO. 30)

Primer 4R (71 mer): CgC gAA TTC TCA gTC AgC ATA gTC Tgg gAg gTC ATA Tgg ATAgCC gTC CAT CTC gTT TCT AAC CAA gTT CC (SEQ ID NO. 31)

Figure 8A:
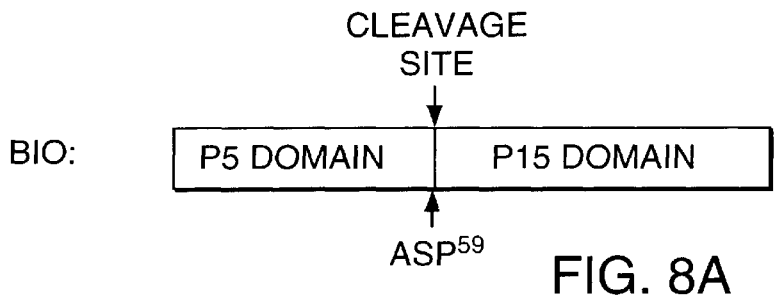
FIGS. 8A–C are drawings illustrating various protein constructs.
Figure 8B:
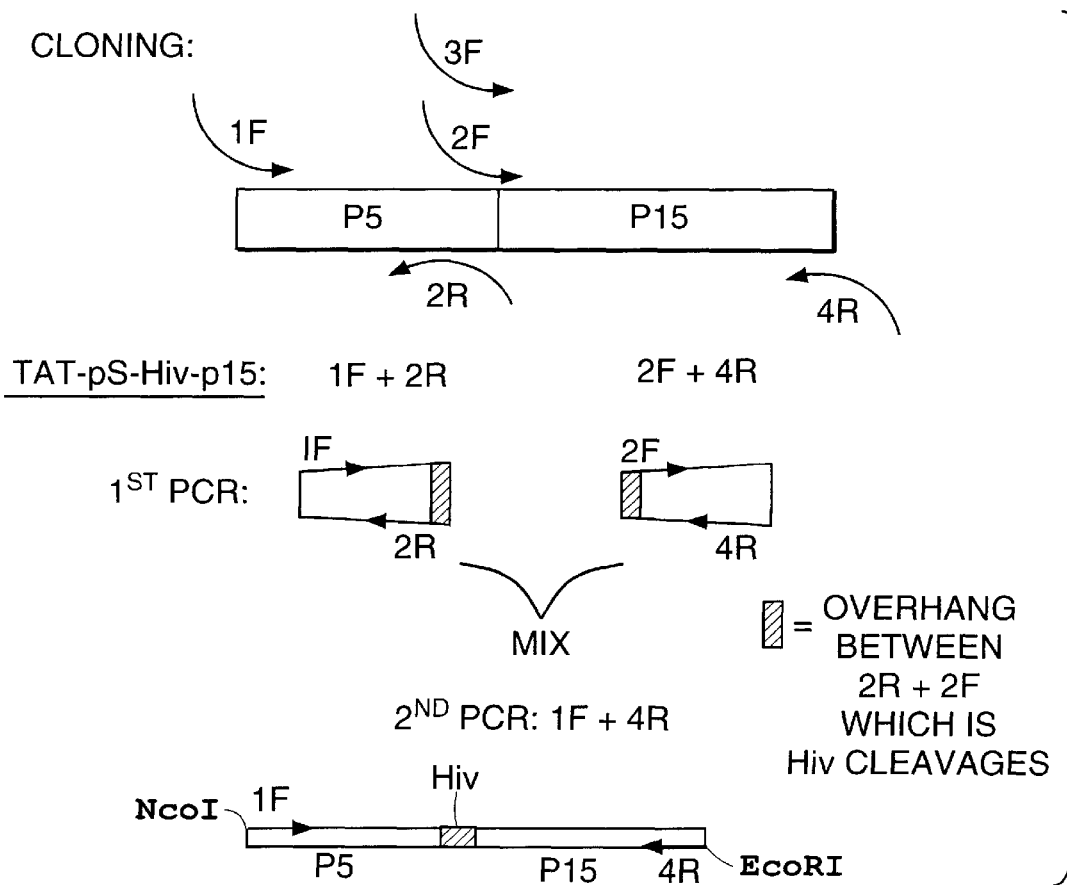
Figure 8C:
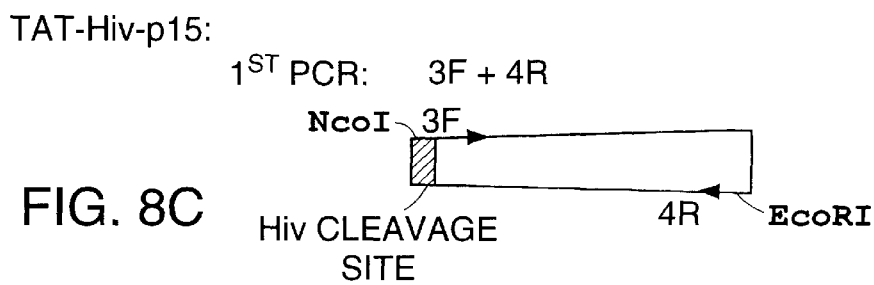

The above-described strategy to clone TAT-p5-HIV-p15 and TAT-HIV-p15 is illustrated in FIGS. 8A–C.

EXAMPLE 12

Killing HIV-Infected Cells by Transduction of an HIV Protease-activated Caspase-3 Protein The HIV Protease-activated Caspase-3 protein was generated to specifically kill cells infected by the HIV virus. The fusion protein was made as follows:

First, a modified Casp3 protein was made by deletion of two residues from the two endogenous caspase cleavage sites (Asp-Ser) on Casp3 and insertion of fourteen residues encompassing the HIV p17-p24 gag cleavage site ("A" site) and a p7-p1 cleavage site ("D" site)20 (FIG. 1A). To introduce the modified Casp3 protein into cells, a previously described method of transducing full length proteins directly into cells was used. See Barrie, K. A., et al., Natural variation in HIV-1 protease, gag p7 and p6, and protease cleavage sites within gag/pol polyproteins: amino acid substitutions in the absence of protease inhibitors in mothers and children infected by human immunodeficiency virus type 1. *Virology* 219: 407 (1996); Ezhevsky, S. A., et al., Hypo-phosphorylation of the retinoblastoma protein by cyclin D:Cdk4/6 complexes results in active, pRb. *Proc. Natl. Acad. Sci. USA* 94: 10699 (1997); Lissy, N. A., et al., TCR-antigen induced cell death (AID) occurs from a late $G_1$ phase cell cycle check point. *Immunity* 8: 57 (1998); Nagahara, H. et al., Highly efficient transduction of full length TAT fusion proteins directly into mammalian cells: p27$^{Kip1}$ mediates cell migration. *Nature Med.* (in press) (1998); Vocero-Akbani, A., et al., Transaction of full length TAT fusion proteins directly into mammalian cells:analysis of TCR-activation induced cell death (AID). In *Methods in Enzymology* (ed Reed, J. C.) (Academic Press, San Diego) (in press) (1998).

Briefly, bacterially produced, misfolded fusion proteins containing an in-frame N' terminal protein transduction domain from HIV TAT are capable of transducing in a rapid and concentration-dependent fashion into ~100% of all target cell types, including: peripheral blood lymphocytes (PBL), all cells present in whole blood, diploid fibroblasts, fibrosarcoma cells, hepatocellular carcinoma cells and leukemic T cells. See Ezhevsky, S. A. et al., Lissy, N. A. et al., Nagahara, H., et al., and Vocero-Akbani, A. et al. (supra). The Pro domain of the modified Casp3 was removed and substituted with the TAT transduction domain resulting in TAT-Casp3WT fusion protein (FIG. 9A). In addition, a catalytically inactive TAT-Casp3 mutant protein was generated by substituting a Met residue for the Casp3 active site Cys'63 residue (TAT-Casp3MUT).

To test the ability of TAT-Casp3 proteins to transduce into cells, TAT-Casp3 proteins were conjugated to fluorescein (FITC), then added directly to the media of Jurkat T cells and analyzed by Flow Cytometry (FACS) (FIGS. 9B–C). Both TAT-Casp3WT and TAT-Casp3MUT proteins rapidly transduced into ~100% of cells, achieving maximum intracellular concentration in less than 20 min. In addition, based on the narrow peak width before and after addition of FITC labeled proteins, individual cells within the population contain near identical intracellular concentrations of TAT-Casp3-FITC protein. Confocal microscopy analysis showed the presence of TAT-Casp3FITC proteins in both cytoplasmic and nuclear compartments and not merely attached to the cellular membrane. FACS analysis of transduced cells at equilibrium 1 hr post-addition of 3, 6 and 12 nM TAT-Casp3WT-FITC protein demonstrated a concentration-dependency for protein transduction (FIG. 9E). Thus, TAT-Casp3 proteins readily transduce into 100% of all cells in a rapid and concentration-dependent fashion.

To test the concept of HIV Protease cleavage of transduced heterologous substrates, a model substrate was made by inserting HIV proteolytic cleavage sites into a previously characterized TAT-p16 fusion protein. See Ezhevsky, S. A. et al., Lissy, N. A., et al., and Vocero-Akbani, A., et al. (supra). The HIV A cleavage site was inserted between the TAT and p16 domains, yielding TAT-A-p16 fusion protein (FIG. 9A). In addition, a transducible HIV Protease (TAT-HIV Pr) was made. See FIG. 9A. FITC-labeled TAT-A-p16, TAT-16 proteins. (See Ezhevsky, S. A., et al., and Vocero-Akbani, A., et al. (supra) and TAT-HIV Pr protein (FIG. 9D) were found to rapidly transduced into 100% of cells.

The generation and transduction of TAT fusion proteins shown in FIGS. 9A–E are explained in more detail as follows: FIG. 9A. Diagram depicting HIV cleavage site sequences and domains of TAT fusion proteins. FIGS. 9B–D. FACS kinetic analysis of fluorescein (FITC) labeled TAT-Casp3WT, TAT-Casp3MUT and TAT-HIV Pr proteins added to cells at 0, 20 and 30 min. FIG. 9E. FACS dose analysis of 3, 6, and 12 nM TAT-Casp3WT-FITC protein added to cells at I hr post-addition. Note rapid, concentration-dependent transduction of all FITC labeled protein into ~100% of cells and near identical intracellular concentration within the population as measured by FACS peak width of control vs. transduced cells.

Figure 10A:
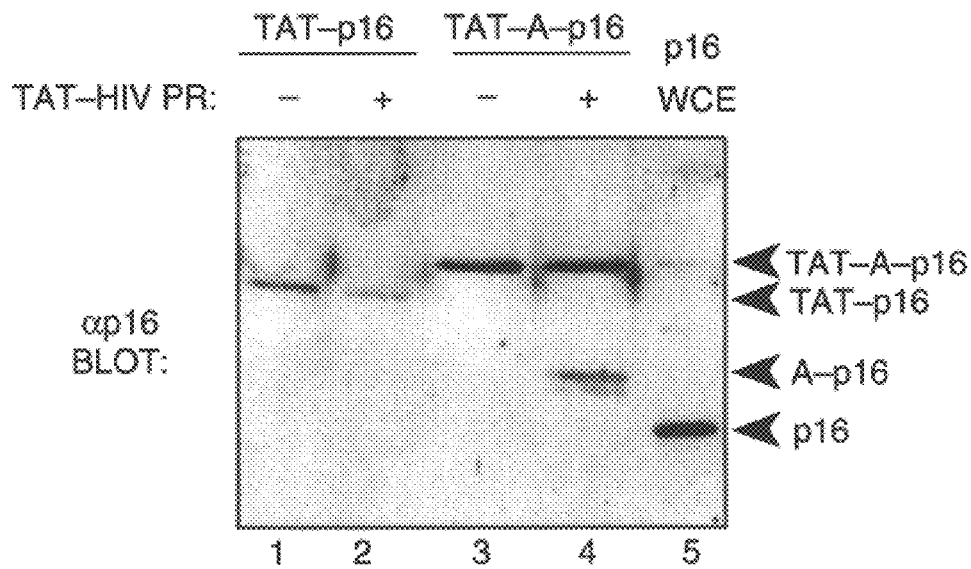
FIGS. 10A–B are representations of immunoblots showing in vivo processing of various TAT fusion proteins in Jurkat T cells. The immunoblots were probed with anti-p16 (FIG. 10A) or anti-Caspase-3 antibody (FIG. 10B).

To assay for in vivo cleavage, p 16(−) Jurkat T cells were transduced with 100 nM TAT-Ap16 or control TAT-p16 protein (no HIV cleavage site) alone or in combination with 50 nM TATHIV Pr fusion protein for 5 hr and analyzed by anti-p16 immunoblot for in vivo cleavage at the HIV A proteolytic cleavage site (FIG. 10A). Co-transduction of TAT-A-p16 protein substrate with TAT-HIV Pr resulted in specific substrate cleavage while control TAT-p 16 protein (no HIV cleavage site) was not cleaved. Size analysis of the cleaved TAT-A-p 16 protein was consistent with retention of the residual HIV half site present on the N' terminus of p 16 (FIG. 10A, see lane 4 vs. 5). It was also noted that the HIV A site was preferentially cleaved over a D site containing TAT-Dp16 protein in this assay.

Figure 10B:
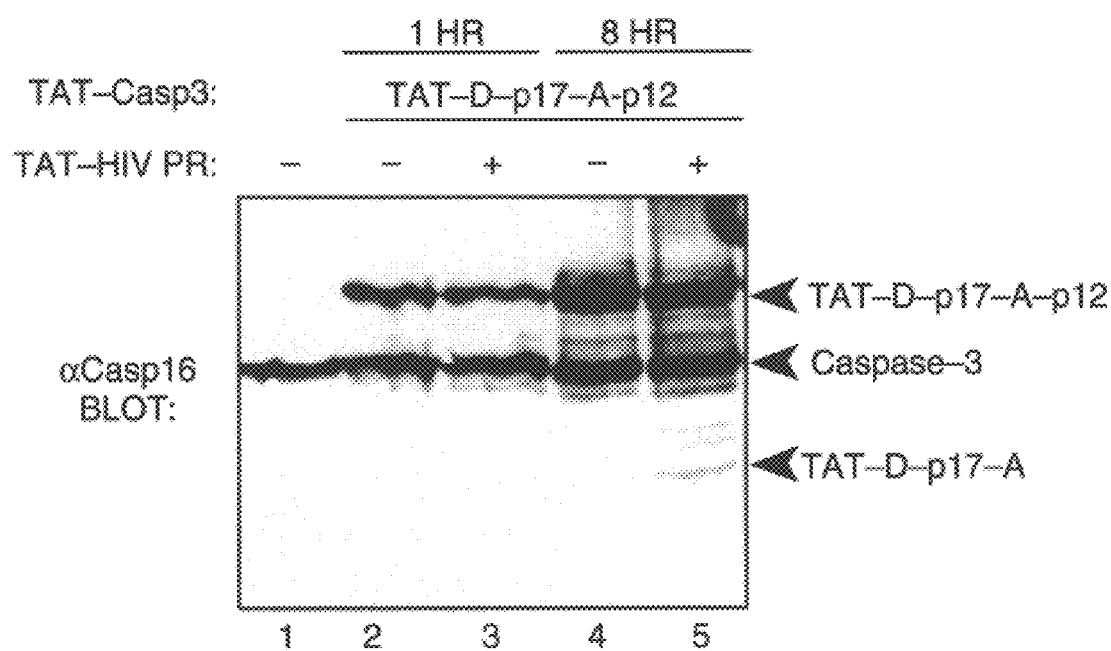

Further, the TAT-Casp3MUT protein was transduced in combination with TAT-HIV Pr protein into cells (FIG. 10B). Co-transduction of TAT-Casp3 with TAT-HIV Pr resulted in deletion of specific cleavage of TAT-Casp3 at the HIV "A" site between the p 17 and p 12 domains in an HIV Protease-dependent fashion, yielding a TAT-D sitep17-A half site protein. These observations demonstrate that transduced TAT-Ap 16 and TAT-Casp3 proteins containing heterologous HIV cleavage sites can be recognized as substrates by TAT-HIV Protease in vivo.

The in vivo processing in co-transduced cells shown in FIGS. 10A and 10B is explained in more detail as follows. FIG. 10A. Cultures of p16(−) Jurkat T cells were transduced with TAT-p 16 or TAT-A-p 16 substrate proteins in combination with TATHIV Pr proteins for 5 hr and subjected to anti-p 16 immunoblot analysis. Co-transduction of TATA-p16 protein with TAT-HIV Pr protein resulted in specific cleavage at the HIV A site. WCE, HepG2 whole cell lysate containing wild type endogenous p16; A-p16, cleaved TAT-A-16 product retaining the HIV half site on p16. FIG. 10B. Cultures of Juikat T cells were transduced with TATCasp3MUT protein (TAT-"D" site-p 17 domain-"A" site-p12 domain) alone or in combination with TAT-HIV Pr (Pr) protein as indicated and immunoblotted with anti-Caspase-3 antibodies specific for the p17 domain. TAT-D-p17-A, cleaved product of TAT-Casp3 containing the N' terminal HIV A half site.

Figure 11A:
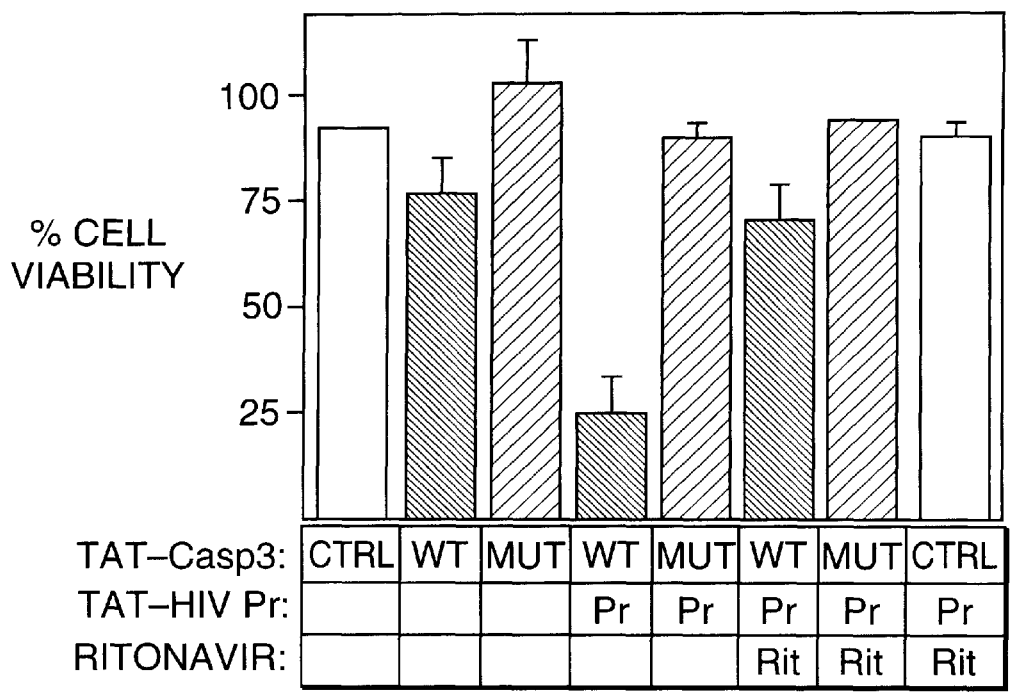
FIGS. 11A–B are graphs showing activation of TAT-Casp3 and apoptotic induction in cotransduced cells.
Figure 11B:
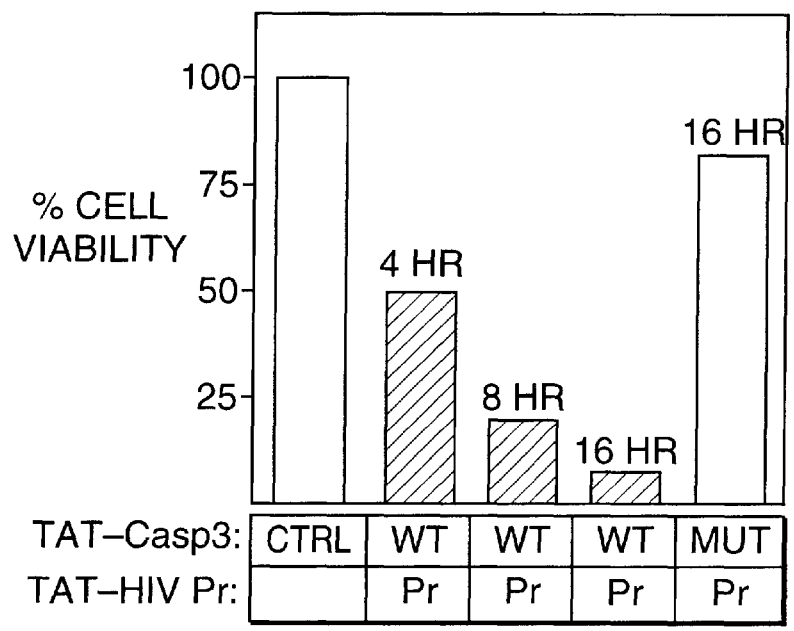

In addition, the ability of TAT-Casp3 protein to induce apoptosis in cells co-transduced with TAT-HIV Pr protein was tested. Jurkat T cells were treated with 100 nM TAT-Casp3WT or TATCasp3MUT proteins alone or in combination with 50 nM TAT-HIV Pr protein and assayed for cell viability 16 hr post-treatment (FIG. 11A). Transduction of TAT-Casp3WT protein alone into cells demonstrated a minor level of cytotoxicity. However, co-transduction of TAT-Casp3WT with TATHIV Pr protein into cells resulted in marked cytotoxicity. Co-transduction of TAT-Casp3MUT with TAT-HIV Pr protein into cells showed only marginal cytotoxicity and also demonstrated an absence of TAT-HIV Protease cytotoxic effects on cells. To further demonstrate the requirement for HIV Protease to activate TAT-Casp3 protein, cells were first pretreated with the HIV Protease inhibitor Ritonavir (1 µg/ml), then co-transduced with TAT-Casp3WT or TAT-Casp3MUT in combination with TAT-HIV Pr protein (FIG. 11A). Pretreatment of cells with Ritonavir resulted in protection from the cytotoxic effects of TAT-Casp3WT protein when co-transduced with TAT-HIV Pr protein. Kinetic analysis of TAT-Casp3-dependent cell death demonstrated a linear killing curve with cellular death detected as early as 4 hr post-transduction (FIG. 11B). These results demonstrate that cytotoxicity occurs only in the presence of catalytically active TAT-Casp3WT protein and that activation of TAT-Casp3WT specifically requires active HIV Protease, consistent with HIV Protease cleavage of TAT-Casp3 (FIG. 10B). See Salvensen, G. S., et al., Henkart, P. A., Cohen, G. M., Woo, M., et al., Enari, M. et al., Liu, X., et al. (supra).

The activation of TPT-Casp3 and apoptotic induction in co-transduced cells shown in FIGS. 11A and 11B is explained in more detail as follows. FIG. 11A Cultures of Jurkat T cells were transduced with combinations of TAT-Casp3WT (WT), TAT-Casp3MUT (MUT) and TAT-HIV Protease (Pr) proteins for 16 hr and analyzed for cell viability. Cotransduction of TAT-Casp3WT with TAT-HIV Pr protein resulted in specific cytotoxicity, whereas transduction of TAT-Casp3MUT with TAT-HIV Pr did not. Inclusion of HIV protease inhibitor Ritonavir (Rit) blocked activation TAT-Casp3WT protein and protected cells from cytotoxic effects. FIG. 11B Cultures of Jurkat T cells were co-transduced with TAT-Casp3WT (WT), TAT-Casp3MUT (MUT) proteins in combination with TAT-HIV Pr (Pr) protein and analyzed for kinetics of cell viability as indicated.

Figure 12A:
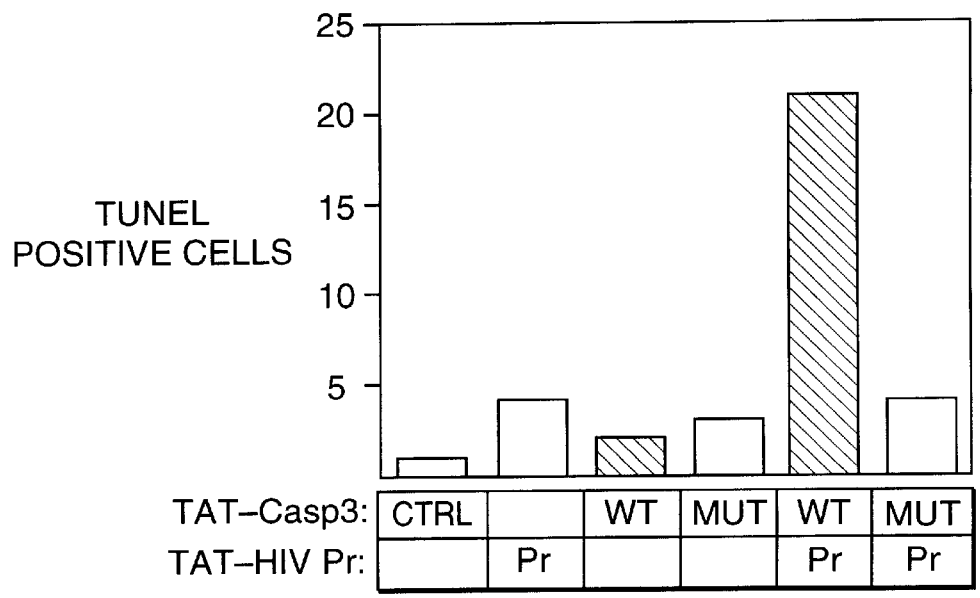
FIGS. 12A–B are graphs showing HIV protease activates TAT-Casp3$^{wt}$ protein.
Figure 12B:
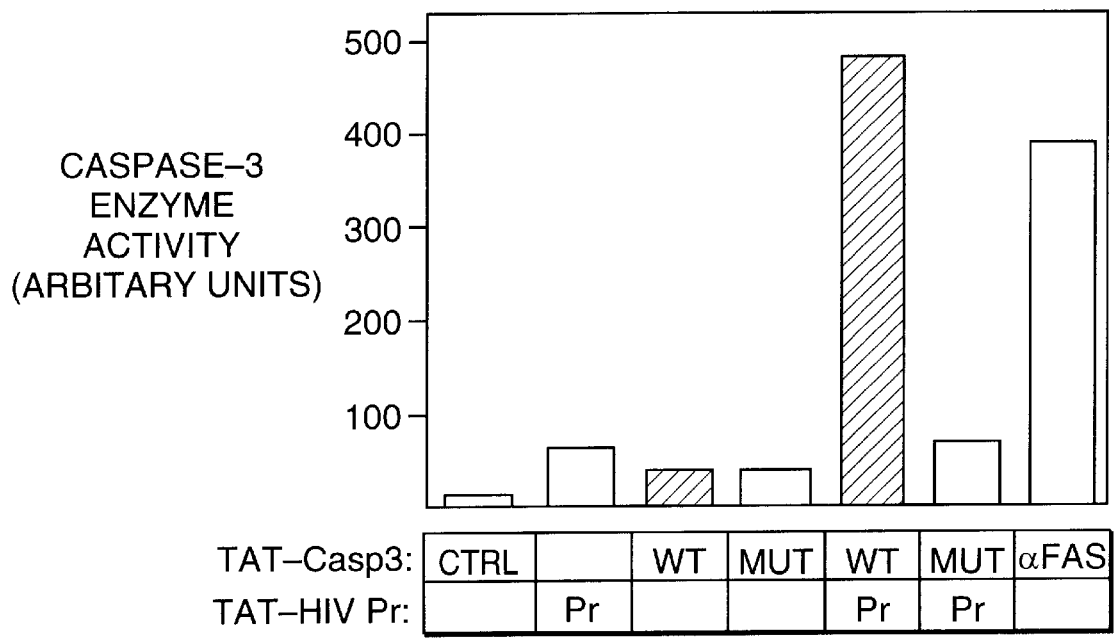

Additionally, transduced cultures were tested for degraded genomic DNA by TUNEL assay. See Coates, P. J., Molecular methods for the identification of apoptosis in tissues. *J. Histctechnology* 17: 261 (1994). Transduction of 100 nM TAT-Casp3WT, 100 nM TAT-Casp3MUT or 50 nM TAT-HIV Pr proteins alone into cells showed only background levels of TUNEL positive cells (FIG. 12A). However, co-transduction of TAT-Casp3WT with TAT-HIV Pr protein resulted in a marked increase in TUNEL positive cells. Co-transduction of TAT-Casp3MUT with TAT-HIV Pr protein showed only background TUNEL positive cells (FIG. 12A). Activation of TAT-Casp3 was also assayed by its ability to cleave an artificial Caspase-3 substrate. Jurkat T cells were treated with 100 nM TAT-Casp3WT or TAT-Casp3MUT proteins alone or in combination with 50 nM TAT-HIV Pr protein for 6 hr and then assayed for cleavage of DEVD-AFC by release of fluorescent AFC (FIG. 12B). See Xiang, J., et al., Bax-induced cell death may not require interleukin 1B-converting enzyme-like proteases. *Proc. Natl. Acad. Sci. USA* 93: 14550 (1996). Consistent with the TUNEL results from above, co-transduction of TAT-Casp3WT and TAT-HIV Pr proteins into cells resulted in a marked increase in caspase activity that was greater than αFAS treatment.

The HIV Protease activates TAT-Casp3WT protein shown in FIGS. 12A–B are explained in more detail as follows. FIG. 12A. Cultures of Jurkat T cells were cotransduced with TAT-Casp3WT (WT) and TAT-HIV Pr (Pr) protein resulted in specific TUNEL positive cells, an apoptotic end-marker. However, transduction of TAT-Casp3MUT (MUT) in combination with TAT-HIV Pr protein and singular transduction of TAT-Casp3WT, TAT-Casp3MUT or TAT-HIV Pr proteins remained at background levels of TUNEL positive cells. Abscissa: TUNEL positive cells per high-powered microscopic field; Ctrl, control addition of PBS to cultures; error bars represent SD. FIG. 12B. Transduction of TAT-Casp3WT in combination with TATHIV Protease as above results in specific activation of caspase-3 activity as measured by DEVDAFC cleavage and AFC fluorescence reported as enzyme activity. Ctrl, control PBS addition; ocFAS crosslinking, positive control.

Transduction of TAT-Casp3WT, TAT-Casp3MUT or TAT-HIV Pr alone showed only background levels of caspase activity. In addition, the appearance of cells containing <2N DNA content was detected in TAT-Casp3 and TAT-HIV Pr co-transduced cells, a classic hallmark of Caspase-3 induced apoptosis as opposed to necrosis. See Woo, M. et al. (supra). These observations demonstrate that transduced TAT-Casp3WT protein remains inactive in cells lacking HIV Protease, but becomes specifically activated in cells harboring active HIV Protease inducing hallmarks of apoptosis and ultimately death.

Due to the absence of a general animal model for HIV, it was of interest to determine if TATCasp3WT protein could kill cells infected with live HIV in culture.

Figure 13:
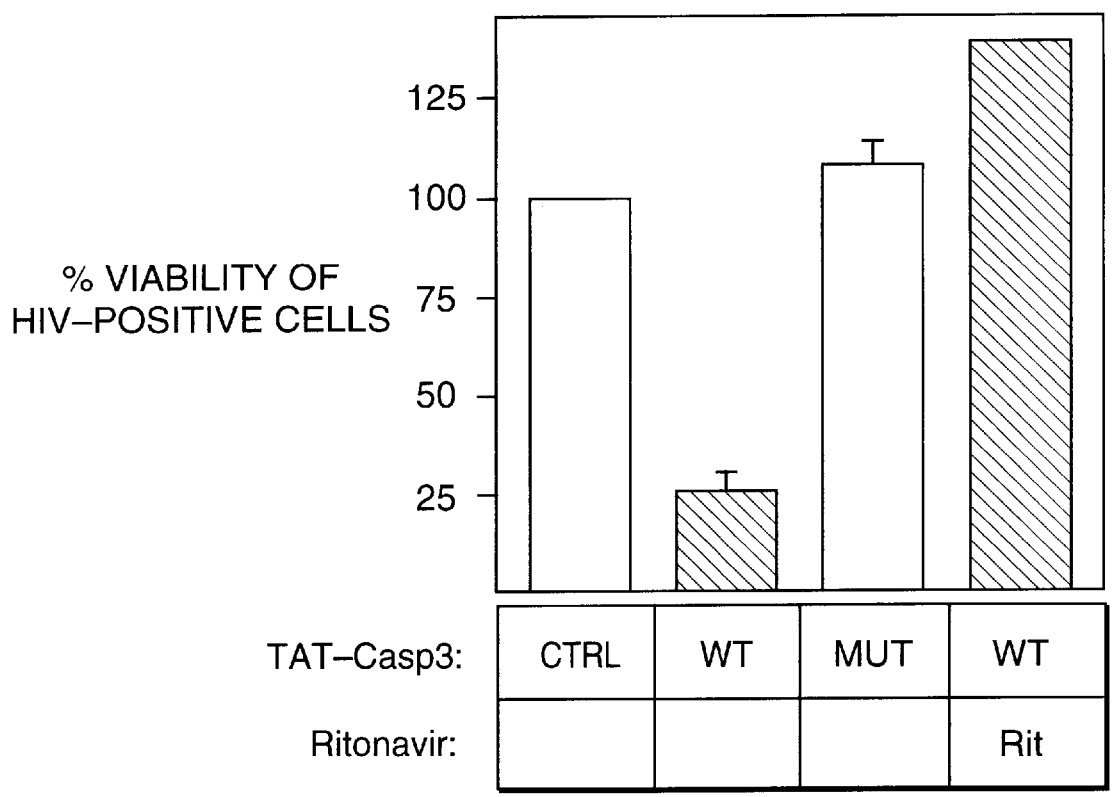
FIG. 13 is a graph illustrating specific killing of HIV infected cells.

To make this determination, Jurkat T cells were infected for 7–14 days with the NLHX strain of HIV-I and (examined microscopically for HIV cytopathic effects. See Westervelt, P., et al., Identification of a determinant within the HIV-1 surface envelope glycoprotein critical for productive infection of cultured primary monocytes. Proc. Natl. Acad. Sci USA 88: 3097 (1991). At the start of each transduction experiment approximately 50% of the culture was HIV positive. HIV infected cultures were transduced for 16 hr with 100 nM TAT-Casp3WT or TATCasp3MUT protein and then assayed for cell viability (FIG. 13). Treatment of HIV infected cells with TAT-Casp3WT protein resulted in a dramatic loss of HIV positive cells from the cultures. In addition, we detected both the appearance of cells containing <2N DNA content and cells with condensed nuclei in TAT-Casp3 treated cells. However, transduction of TATCasp3MUT protein showed negligible effects.

Figure 5:
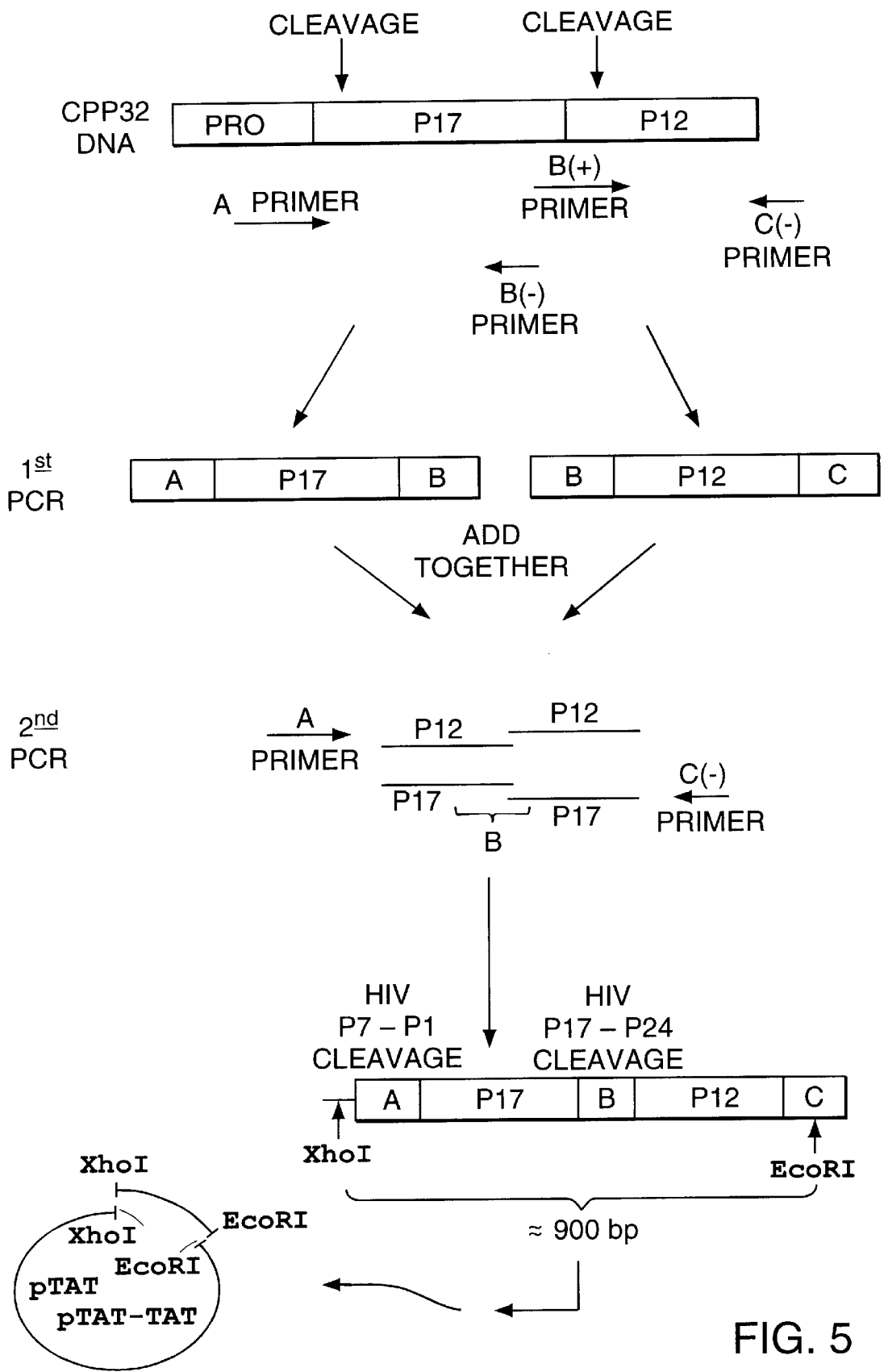
FIG. 5 is a schematic drawing showing one method of constructing a TAT-CPP32 fusion protein according to the invention.

To determine if TAT-Casp3WT induced apoptosis was dependent on active HIV Protease in the infected cultures, HIV infected cultures were pretreated with 1 µg/ml Ritonavir prior to transduction with 100 nM TAT-Casp3WT protein (FIG. 5). Consistent with the experiments above, pretreatment of HIV infected cultures with Ritonavir resulted in protection from TAT-Casp3WT induced apoptosis. In addition, the observed increased survival of Ritonavir treated cells is consistent with increased longevity of protease inhibitor treated HIV infected cells. See Coffin, J. M., et al. (supra). These observations demonstrate specific killing of HIV infected cells by TAT-Casp3WT protein containing active HIV Protease and the lack of apoptotic induction in cells devoid of HIV protease activity.

The specific killing of HIV infected cells shown in FIG. 5 is explained in more detail as follows. Jurkat T cells were infected for 7–14 days with HIV strain NLHX, then transduced with TAT-Casp3WT (WT) or TAT-Casp3MUT (MUT) proteins for 16 hr and assayed for cell viability. TAT-Casp3WT protein efficiently kills a large percentage of HIV positive cells with a single administration, whereas the catalytically inactive TAT-Casp3MUT proteins has no effect. Pretreatment of HIV infected cells with HIV Protease inhibitor Ritonavir (Rit) protects infected cells from TAT-Casp3WT protein killing. Ctrl, control addition of PBS to cultures; abscissa, % viability of HIV positive cells in the population at start of transduction; error bars represent SD.

The present example demonstrates a novel strategy to kill HIV infected cells. Importantly, this strategy harnesses the HIV encoded Protease by utilizing a modified zymogen form of an apoptoliic inducer, Casp3, combined with a protein transduction delivery system. The results show that the transduction of proteins into cells is a rapid, concentration-dependent process that targets ~100% of cells. Importantly, TAT-Casp3 protein remains inactive in uninfected cells and is specifically activated by HIV Protease-dependent cleavage in HIV infected cells. This degree of specificity suggests that killing HIV infected cells by such a strategy may result in a high therapeutic index in patients.

As discussed, current treatment of HIV infected cells with protease inhibitors results in increased longevity of infected cells. In direct contrast to treatment with protease inhibitors, TAT-Casp3 protein specifically kills HIV infected cells. In addition, selection for mutations that renders the HIV Protease resistant to a broad spectrum of inhibitors is a continuing and growing problem in combating the HIV epidemical. However, by substituting HIV cleavage sites, the approach provided in this example and elsewhere in this disclosure allows for the continual adaptability of TAT-Casp3 proteins to HIV strain proteolytic cleavage site variance and/or mutation.

The TAT-Casp3 proteins described herein can be used to combat other pathogens by manipulating the proteins to contain relevant pathogen specific protease cleavage sites.

The following methods were used in this example.

1. Cell culture-p16(−) Jurkat T cells (ATCC) were grown as described. See Lissy, N. A., et al. (supra). For in vivo substrate cleavage, $1 \times 10^6$ cells were transduced with 100 nM TAT-p16, TAT-A-p16, TAT-Casp3MUT and/or 50 nM TAT-HIV Pr proteins for 1, 5 or 8 hr as indicated and analyzed by anti-p16 (Santa Cruz) or anti-Casp3 (Pharmingen) immunoblot analysis. See Ezhevsky, S. A., et al. (supra). For cytotoxicity of TAT-Casp3 on uninfected cells, $1 \times 10^6$ cells were transduced with 100 nM TAT-Casp3WT, TAT-Casp3MUT and/or 50 nM TAT-HIV Pr proteins for 16 hr and assayed for viability by Trypan Blue exclusion and/or genomic DNA damage by TUNEL assay (Trevigen). Number of TUNEL positive cells reported as per high-powered microscopic field with four fields per experiment averaged. TAT-Casp3 activity was measured by incubation of 20 µg of whole cell lysate with 50 µM DEVD-AFC and fluorescent AFC formation measured on a FL500 microplate fluorescence reader (Bio-Tek) as described. See Xiang, J., et al., (supra). Cells were preincubated with 1 µg/ml Ritonavir (Abbott Labs) for 1 hr prior to transduction. For cytotoxicity of TAT-Casp3 on infected cells, Jurkat cultures were infected with 100 ng p24 Ag equivalent NLHX HIV-I strain for 7–14 days, assayed microscopically for cytopalhic effects, then replated at $1 \times 10^6$/ml and transduced with 100 nM of TAT-Casp3WT or TAT-Casp3MUT proteins for 16 hr followed by exclusionary dye viability analysis. Infected cells were pretreated with 1 µg/ml Ritonavir for 24 hr prior to transduction with TAT-Casp3WT protein. See Xiang, J., et al., (supra). For Flow Cyrtometry (FACS) analysis, fluorescein (FITC) conjugated TAT fusion proteins were added to Jurkat T cell culture media and $1 \times 10^4$ cells were analyzed by FACS as described. See Ezhevsky, S. A., et al. (supra).

2. TAT fusion proteins-pTAT-A/D-p16 expression vectors were constructed by inserting double stranded oligomeric nucleotides encoding 14 residues of the HIV p17-p24 ("A") cleavage site (single amino acid code: SQVSQNY-PIVQNLQ SEQ ID NO. 9) or the HIV p7-p 1 ("D") cleavage site (CTERQAN-FLGKIWP; SEQ ID NO. 10) into the Nco-I site of pTAT-p16. See Ratner, L., et al., Welch, A. R., et al., Nagahara, H., et al., and Vocero-Akbani, A., et al. (supra). pTAT-Casp3WT vector was constructed by independent PCR amplification of the p17 and p12 domains containing engineered HIV A and D cleavage sites (14 residues) into the primers (p17-forward primer: 5' -CGCCTCGAGGGCGGCTGCACCGAACGCCAG GCTAACTTCCTGGGCAAAATCTGGCCAG-GCGGAATATCCCTGGACAACAG TTATAAAATG-3' (SEQ ID NO. 32); p17-reverse primer: 5' CCGCCCTG-CAGGTTCTGC ACGATTGGATAGT TCTGTGACAC-CTGGGAGJCCGCCTGTCTCAATGCCACAGTCCAG 3' (SEQ ID NO. 33);

p12-forward primer: 5'-GGCGGCTCCCAGGTGTCACAGAA CTATC-CAATCGTGCAGAACC TGCAGGGCGGTGTTGAT-GATGACATGGCG 3' (SEQ ID NO. 34);

p12-reverse primer: 5' -CGAGCTACGCG AATTCTTAGT-GATAAAAATAGAGTTC 3'; (SEQ ID NO. 35)

followed by mixing PCR products and PCR amplification using the p 17-forward and p 12-reverse primers (p 17 reverse and p 12-forward primer sequences overlap). The resultant PCR fragment was subcloned into pTAT-HA23 24 resulting in a TAT-D-p17-A-p12 configuration (see FIG. 9A). pTAT-Casp3MUT vector was constructed by inserting a double stranded oligomeric nucleotide (positive strand:5'-CCATGCGTGGTACCGA ACTGGACT-GTGGCAT TGAGACAGGCGGCTCCCAGGTGTCA-CAGAACTATCCAATCGT GCAGAACCTGCA-3'; (SEQ ID NO. 36) containing a Met residue for the active site Cys'63 residue into the Stu-I and Pst-I sites of pTAT-Casp3WT vector.

pTAT-HIV Pr vector was constructed by PCR cloning the HIV Protease gene from HXB2R HIV strain (forward primer: 5' CGGTCCATGGGCGGCG GCCCTCAGGT-CACTCTTTGGCAACG 3' (SEQ ID NO. 37); reverse primer: 5' CGGGAATTCTCAAAAATTTAA AGTGCAACCAATCTG-3' (SEQ ID NO. 38) and cloning into pTAT23 24. Briefly, TAT fusion proteins were purified by sonication of high expressing BL21 (DE3)pLysS (Novagen) cells in 8 M urea, purified over a Ni-NTA column and misfolded on a Mono S column as described23 24. FITC conjugated TAT fusion proteins were generated by fluorescein isothiocyanate labeling (Pierce), followed by gel purification in PBS on an S-12 column attached to an FPLC (Pharmacia) or PD-10 desalting column (Pharmacia), then added directly to cells in culture media and analyzed by FACS or microscopy.

EXAMPLE 13

Production and Testing of Class II Synthetic Transduction Domains

In the course of further investigation of synthetic transduction domains that require a strong alpha helical structure with a face of Arginine residues down the helical cylinder, now referred to as Class I type of synthetic transduction domains, an apparent second class of transduction domains, termed Class II type was discovered. Class II synthetic transduction domains also require basic residues, such as Arginine or Lysine, but preferably Arginine; however, the introduction of kinks in the secondary structure due to the inclusion of Proline residues distinguishes them from Class I domains.

Below are listed six examples of Class II type of synthetic transduction domains and their relative transduction potential compared to HIV TAT 47-57, using single letter amino acid code:

TABLE 3

| SEQ ID #: | | Relative Transduction Potential to TAT: |
|---|---|---|
| 55 | YARAARRPRRR | 5x |
| 56 | YARAPRRARRR | 3x |
| 57 | YARAPRRPRRR | 3x |
| 40 | YARAAARPARA | unknown |
| 40 | YARAPARQARA | unknown |
| 41 | YARAPARPARA | unknown |

The invention has been described in detail with reference to preferred embodiments thereof. However, it will be appreciated that those skilled in the art, upon consideration of this disclosure, may make modifications and improvements within the spirit and scope of the invention.

---

What is claimed is:

1. An anti-pathogen system comprising a fusion protein comprising a covalently linked protein transduction domain and a cytotoxic domain, wherein the cytotoxic domain further comprises at least one pathogen-specific protease cleavage site.

2. The anti-pathogen system of claim 1, wherein the fusion protein comprises covalently linked in sequence: 1) the transduction domain, 2) a first pathogen-specific protease cleavage site, and 3) a zymogen.

3. The anti-pathogen system of claim 1, wherein the fusion protein comprises covalently linked in sequence: 1) the transduction domain, 2) a first pathogen-specific protease cleavage site, 3) a catalytic zymogen fragment, and 4) a first zymogen subunit.

4. The anti-pathogen system of claim 3, wherein the fusion protein further comprises covalently linked to the C-terminal end of the first zymogen subunit, 5) a second pathogen-specific protease cleavage site, and 6) a second zymogen subunit.

5. The anti-pathogen system of claim 2, wherein the zymogen is a caspase, thrombin, bacterial exotoxin, granzyme B or an invertebrate toxin.

6. The anti-pathogen system of claim 5, wherein the caspase is selected from the group consisting of caspase-3 (CPP32 apopain, Yama), caspase-5 ($ICE_{rel}$-III, TY), caspase-4($ICE_{rel}$-II TX, ICH-2), caspase-1 (ICE), caspase-7 (Mch3, ICE-LAP3, CMH-1), caspase-6 (Mch2), caspase-8 (MACH, FLICE, Mch5), caspase-10 (Mch4), caspase-2 (ICH-1), caspase-9 (ICH-LAP6, Mch6),) and a catalytically active zymogen.

7. The anti-pathogen system of claim 6, wherein the caspase is caspase-3 (CPP32 apopain, Yama) or a catalytically active fragment thereof.

8. The anti-pathogen system of claim 1, wherein the fusion protein further comprises covalently linked in sequence: 1) the transduction domain, 2) a pathogen-specific protease cleavage site, and 3) an enzyme.

9. The anti-pathogen system of claim 8, wherein the enzyme is thymidine kinase, cytosine deaminase, or a catalytically active enzymatic fragment thereof.

10. The anti-pathogen system of claim 9, wherein the enzyme is thymidine kinase.

11. The anti-pathogen system of claim 1, wherein the pathogen-specific protease cleavage sites are selected from the group consisting of cytomegalovirus (CMV), herpes simplex virus type-1 (HSV-1); hepatitis virus type C (HCV); *P. falciparum*, HIV-1, HIV-2 and Kaposi's sarcoma-associated herpes virus (KSHV) protease cleavage sites.

12. The anti-pathogen system of claim 1, wherein the fusion protein comprises covalently linked in sequence: 1) TAT or a protein transducing fragment thereof, 2) a caspase-3 prodomain, 3) a first HSV-1 protease cleavage site, 4) a caspase-3 large subunit, 5) a second HSV-1 protease cleavage site, and 5) a caspase-3 small subunit, wherein the large and small subunits dimerize to form a cytotoxin.

13. The anti-pathogen system of claim 1, wherein the protein transduction domain is TAT, Antennapedia homeodomain, HSV VP22 or a transducing fragment thereof.

14. A substantially pure fusion protein comprising a covalently linked protein transduction domain and a cytotoxic domain.

15. A kit comprising:

an anti-pathogen system comprising a fusion protein which comprises a protein transduction domain for entry of the fusion protein into a cell and a cytotoxic domain that specifically produces a cytotoxin in response to infection by one or more pathogens.

16. The anti-pathogen system of claim 1, wherein the protein transduction domain is a synthetic peptide or other transducing protein.

17. The anti-pathogen system of claim 1, wherein the fusion protein comprises covalently linked in sequence: 1) a transduction domain, 2) a first zymogen subunit, 3) a protease cleavage site, and 4) a second zymogen subunit.

18. The anti-pathogen system of claim 17, wherein the transduction domain is TAT, the first zymogen subunit is p5 Bid, the protease cleavage site is an HIV protease cleavage site and the second zymogen subunit is p15 Bid.

19. The anti-pathogen system of claim 1, wherein the fusion protein comprises covalently linked in sequence: 1) a transduction domain, 2) a first protease cleavage site, 3) first zymogen subunit, 4) a second protease cleavage site, and 5) a second zymogen subunit.

20. The anti-pathogen system of claim 19, wherein the transduction domain is TAT, the first protease cleavage site is an HIV p7-p1 protease cleavage site, the first zymogen subunit is p17 caspase-3, the second protease cleavage site is an HIV p17-p24 protease cleavage site, and the second zymogen subunit is p12 caspase-3.

21. The anti-pathogen system of claim 20, wherein the p17 caspase-3 comprises a $Cys^{163}$ to $Met^{163}$ mutation.

* * * * *